(12) United States Patent
Mogelsvang et al.

(10) Patent No.: US 10,899,797 B2
(45) Date of Patent: *Jan. 26, 2021

(54) PEPTIDES AND METHODS OF USING SAME

(71) Applicant: Serpin Pharma, LLC, Nokesville, VA (US)

(72) Inventors: Soren Mogelsvang, Boulder, CO (US); Cohava Gelber, Nokesville, VA (US)

(73) Assignee: SERPIN PHARMA, LLC, Manassas, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/286,298

(22) Filed: Feb. 26, 2019

(65) Prior Publication Data

US 2020/0017550 A1 Jan. 16, 2020

Related U.S. Application Data

(60) Continuation of application No. 14/609,069, filed on Jan. 29, 2015, now Pat. No. 10,214,562, which is a division of application No. 13/925,067, filed on Jun. 24, 2013, now Pat. No. 8,975,224, which is a continuation-in-part of application No. PCT/US2013/020498, filed on Jan. 7, 2013.

(60) Provisional application No. 61/699,571, filed on Sep. 11, 2012, provisional application No. 61/584,517, filed on Jan. 9, 2012.

(51) Int. Cl.
*C07K 7/08* (2006.01)
*C07K 14/81* (2006.01)
*A61K 38/00* (2006.01)

(52) U.S. Cl.
CPC ............ *C07K 7/08* (2013.01); *C07K 14/8125* (2013.01); *A61K 38/00* (2013.01)

(58) Field of Classification Search
None
See application file for complete search history.

(56) References Cited

U.S. PATENT DOCUMENTS

| | | | |
|---|---|---|---|
| 4,897,355 A | 1/1990 | Eppstein et al. |
| 4,946,787 A | 8/1990 | Eppstein et al. |
| 4,968,317 A | 11/1990 | Toermaelae et al. |
| 5,049,386 A | 9/1991 | Eppstein et al. |
| 5,399,346 A | 3/1995 | Anderson et al. |
| 5,436,146 A | 7/1995 | Shenk et al. |
| 5,459,127 A | 10/1995 | Felgner et al. |
| 5,580,561 A | 12/1996 | Cercek et al. |
| 5,580,859 A | 12/1996 | Felgner et al. |
| 5,589,466 A | 12/1996 | Felgner et al. |
| 5,618,563 A | 4/1997 | Berde et al. |
| 5,665,557 A | 9/1997 | Murray et al. |
| 5,676,954 A | 10/1997 | Brigham |
| 5,693,622 A | 12/1997 | Wolff et al. |
| 5,703,055 A | 12/1997 | Felgner et al. |
| 5,817,307 A | 10/1998 | Cummins |
| 5,824,300 A | 10/1998 | Cummins |
| 5,830,456 A | 11/1998 | Cummins |
| 5,846,526 A | 12/1998 | Cummins |
| 5,882,640 A | 3/1999 | Cummins |
| 5,910,304 A | 6/1999 | Cummins |
| 5,981,276 A | 11/1999 | Sodroski et al. |
| 6,036,949 A | 3/2000 | Richards et al. |
| 6,143,520 A | 11/2000 | Marasco et al. |
| 6,261,569 B1 | 7/2001 | Comis et al. |
| 6,372,218 B1 | 4/2002 | Cummins |
| 2005/0106151 A1 | 5/2005 | Shapiro |
| 2009/0111766 A1 | 4/2009 | Atkinson et al. |
| 2009/0117578 A1 | 5/2009 | Metz et al. |
| 2009/0186002 A1 | 7/2009 | Flotte et al. |
| 2009/0203580 A1 | 8/2009 | Dinarello et al. |
| 2010/0111940 A1 | 5/2010 | Flier et al. |
| 2010/0267052 A1 | 10/2010 | Gelber et al. |
| 2010/0322894 A1 | 12/2010 | Atkinson et al. |

FOREIGN PATENT DOCUMENTS

| | | |
|---|---|---|
| EP | 97994 A2 | 1/1984 |
| KR | 20160146242 A | 12/2016 |
| WO | WO 9409469 A1 | 4/1994 |
| WO | WO 9412649 A2 | 6/1994 |
| WO | WO 9607425 A1 | 3/1996 |
| WO | WO 2005114221 A2 | 12/2005 |
| WO | WO 2009029847 A1 | 3/2009 |
| WO | WO 2011002834 A2 | 1/2011 |
| WO | WO2011-126882 * | 3/2011 |
| WO | WO 2011041325 A2 | 4/2011 |
| WO | WO 2011126882 A2 | 10/2011 |

OTHER PUBLICATIONS

Chipp ("Sepsis in Burns" Annals of Plastic Surgery vol. 65, No. 2, 2010).*
Bergin et al. (2012) "Alpha1-Antitrypsin: A Potent Anti-Inflammatory and Potential Novel Therapeutic Agent," Arch. Immunol. Ther. Exp. 60(2):81-97.
Churg et al. (2001) "Alpha1-Antitrypsin and a Broad Spectrum Metalloprotease Inhibitor, RS113456, Have Similar Acute Anti-Inflammatory Effects," Laboratory Investigation. 81(8):1119-1131.
Dhami et al. (2000) "Acute Cigarette Smoke-Induced Connective Tissue Breakdown Is Mediated by Neutrophils and Prevented by a1-Antitrypsin," Am. J. Respir. Cell Mol. Biol. 22:244-252.
Ding et al. (2004) "The influence of dipeptide composition on protein thermostability," FEBS Letters. 569:284-288.
Galati et al. (2003) "Increased resistance of peptides to serum proteases by modification of their amino groups," Zeitschrift fur Naturforschung. 58(7-8):558-561.

(Continued)

*Primary Examiner* — James H Alstrum-Acevedo
*Assistant Examiner* — Tara L Martinez
(74) *Attorney, Agent, or Firm* — Perkins Coie LLP

(57) ABSTRACT

We describe peptides and their uses for the treatment of autoimmune, inflammatory and metabolic diseases.

15 Claims, 23 Drawing Sheets

Specification includes a Sequence Listing.

(56) References Cited

OTHER PUBLICATIONS

Griese et al. (2007) "a1-Antitrypsin inhalation reduces airway inflammation in cystic fibrosis patients," Eur Respir J. 29:240-250.
Grimstein et al. (2010) "Combination of alpha-1 antitrypsin and doxycycline suppresses collagen-induced arthritis," J Gene Med. 12:35-44.
Grimstein et al. (2011) "Alpha-1 antitrypsin protein and gene therapies decrease autoimmunity and delay arthritis development in mouse model," Journal of Translational Medicine. 9(21):1-13.
Janciauskiene et al. (2004) "Divergent effects of a1-antitrypsin on neutrophil activation, in vitro," Biochemical and biophysical research communications. 315(2):288-296.
Janciauskiene et al. (2004) "Inhibition of lipopolysaccharide-mediated human monocyte activation, in vitro, by α1-antitrypsin," Biochemical and biophysical research communications. 321(3):592-600.
Kalis et al. (2010) "Alpha 1-antitrypsin enhances insulin secretion and prevents cytokinemediated apoptosis in pancreatic (3-cells," Islets. 2(3):185-189.
Kinexus (Peptide array synthesis, posted online Jan. 2010.
Koulmanda et al. (2008) "Curative and p. cell regenerative effects of a1-antitrypsin treatment in autoimmune diabetic NOD mice," Proceedings of the National Academy of Sciences. 105(42):16242-16247.
Lange et al. (Jun. 1, 2009) "Suppression of protein aggregation by L-arginine," Current Pharmaceutical Biotechno. 10(4):408-414.
Lewis et al. (2005) "a1-Antitrypsin monotherapy prolongs islet allograft survival in mice," Proceedings of the National Academy of Sciences. 102(34):12153-12158.
Lewis et al. (2008) "a1-Antitrypsin monotherapy induces immune tolerance during islet allograft transplantation in mice," Proceedings of the National Academy of Sciences. 105(42):16236-16241.
Libert et al. (1994) "Protection by a1-acid Glycoprotein against Tumor Necrosis Factor-induced Lethality," J. Exp. Med. 180:1571-1575.
Libert et al. (1996) "a1-Antitrypsin Inhibits the Lethal Response to TNF in Mice," The Journal of Immunology. 157:5126-5129.
Lu et al. (2006) "a1-Antitrypsin Gene Therapy Modulates Cellular Immunity and Efficiently Prevents Type 1 Diabetes in Nonobese Diabetic Mice," Human Gene Therapy. 17:625-634.
Ma et al. (2010) "Intradermal a1-anfitrypsin therapy avoids fatal anaphylaxis, prevents type 1 diabetes and reverses hyperglycaemia in the NOD mouse model of the disease," Diabetologia. 53:2198-2204.
Martin et al. (2006) "Safety and Efficacy of Recombinant Alpha1-Antitrypsin Therapy in Cystic Fibrosis," Pediatric Pulmonology. 41:177-183.
Mimotopes (Overcoming peptide problems by Design, published online, Feb. 2001).
National Center for Biotechnology Information (Jul. 28, 2016) "alpha-1 antitrypsin, partial [Homo sapiens]," GenBank Accession No. AAB59371.1, 1 page.
Nita et al. (2005) "Prolastin, a pharmaceutical preparation of purified human a1-antitrypsin, blocks endotoxin-mediated cytokine release," Respiratory Research. 6(12):1-11.
Song et al. (2004) "Recombinant associated virus-mediated alpha1-antitrypsin gene therapy prevents type I diabetes in NOD mice," Gene Therapy. 11:181-186.
Strohl (2015) "Fusion proteins for half-life extension of biologics as a strategy to make biobetters," BioDrugs. 29(4):215-239.
Subramaniyam et al. (2006) "C-36 peptide, a degradation product of a1-antitrypsin, modulates human monocyte activation through LPS signaling pathways," The International Journal of Biochemistry & Cell Biology. 38:563-575.
Subramaniyam et al. (2008) "TNF-a-induced self expression in human lung endothelial cells is inhibited by native and oxidized a1-antitrypsin," The International Journal of Biochemistry & Cell Biology. 40:258-271.
Tawara et al. (2011) "Alpha-1-antitrypsin monotherapy reduces graft-versus host disease after experimental allogenic bone marrow transplantation," PNAS. 109(2):564-569.
Verdini et al. (1985) "Synthesis, resolution, and assignment of configuration of potent hypotensive retro-inverso bradykinin potentiating peptide 5a (BPP 5a) analogues," Journal of the Chemical Society, Perkin Transactions. 1:697-701.
Zhang et al. (2007) "a1-Anfitrypsin Protects (β-Cells From Apoptosis," Diabetes. 56:1316-1323.

\* cited by examiner

| Serpin C-terminal Peptides | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| Human AAT C36 | 1 | S | I | P | P | E | | | | | V | K | F | N | K | P | F | V | F | L | M | I | E | Q | N | T | K | S | P | L | F | M | G | K | V | N | T Q K |
| Human KALLISTATIN (C39) | 2 | S | A | Q | T | N | | | R | H | L | R | F | N | R | P | F | L | V | V | F | S | T | S | T | Q | S | V | L | F | L | G | K | V | V | D | P T K P |
| Human Antichymotrypsin (C40) | 3 | A | L | V | E | T | R | T | | | V | R | F | N | R | P | F | L | M | I | I | V | P | T | D | T | Q | N | I | F | F | M | S | K | V | T | N P K Q A |
| Rat Serpina3M (C38) | 4 | S | G | R | P | P | M | | | | Y | W | F | N | R | P | F | L | L | I | A | I | S | H | T | H | G | T | I | L | F | M | A | K | V | I | N P V G A |
| Rat Serpina3K (C38) | 5 | K | S | L | P | Q | T | I | P | L | L | N | F | N | R | P | F | L | M | L | V | T | D | D | N | G | O | S | V | F | F | M | G | K | V | T | N P M |
| Human Hybrid 1 | 6 | S | A | Q | V | E | T | | | | V | R | F | N | R | P | F | L | V | I | V | S | T | N | T | Q | | | | | | | | | | | |
| Human-Rat Hybrid 1 | 7 | S | I | P | P | Q | M | | | | Y | W | F | N | R | P | F | L | I | A | I | S | H | T | H | T | Q | | | | | | | | | | |

FIG. 1

Peptides derived by truncation

| Source | # | Sequence |
|---|---|---|
| Human AAT C36 | 8 | S I P P E V K F N K P F V F L M I E Q N T K |
| Human KALLISTATIN (C39) | 9 | S A Q T N R H I R F N R P F L V V F S T S T Q |
| Human Antichymotrypsin (C40) | 10 | S A L V E T R T I V R F N R P F L M I V P T D T Q |
| Rat Serpina3K (C38) | 11 | K S L P Q T I P L N F N R P F M L V I T D D N Q |
| Human AAT C36 | 12 | I P P E V K F N K P F V F L M I E Q N T K |
| Human KALLISTATIN (C39) | 13 | N R H I R F N R P F L V V F S T S T Q |
| Human Antichymotrypsin (C40) | 14 | T R T I V R F N R P F L M I V P T D T Q |
| Rat Serpina3K (C38) | 15 | T I P L N F N R P F M L V I T D D N Q |
| C36 Core sequence, long | 16 | V K F N K P F V F L M I E Q N T K |
| C36 Core sequence, short | 17 | V K F N K P F V F L M |
| Human AAT C36 | 18 | S I P P E V K A A A A A F L M I E Q N T K |
| Human AAT C36 | 19 | V K F N K P F V F L M I E Q N T K |
| Human AAT C36 | 20 | V K F N K P F V F L M |
| Human AAT C36 | 21 | K K K V K F N K P F V F L M I E Q N T K K K |
| Human AAT C36 | 22 | K K K V K F N K P F V F L M K K K |
| Human KALLISTATIN (C39) | 23 | I R F N R P F L V V F S T S T Q |
| Human KALLISTATIN (C39) | 24 | I R F N R P F L V V |
| Human KALLISTATIN (C39) | 25 | K K K I R F N R P F L V V F S T S T Q K K K |
| Human KALLISTATIN (C39) | 26 | K K K I R F N R P F L V V K K K |
| Human Antichymotrypsin (C40) | 27 | V R F N R P F L M I V P T D T Q |
| Human Antichymotrypsin (C40) | 28 | V R F N R P F L M I |
| Human Antichymotrypsin (C40) | 29 | K K K V R F N R P F L M I V P T D T Q K K K |
| Human Antichymotrypsin (C40) | 30 | K K K V R F N R P F L M I K K K |
| Human Antichymotrypsin (C40) | 31 | V R F N R P F L |
| Human Antichymotrypsin (C40) | 32 | K K K V R F N R P F L K K K |
| Human AAT C36 | 33 | I P P E V K A A A A A F L M I E Q N T K |
| Scrambled | 34 | F P K M V P Q F N T E L K I F P E V N I K |
| Core | 35 | F N R P F L |
| Core | 36 | K K K F N R P F L K K K |

*FIG. 2*

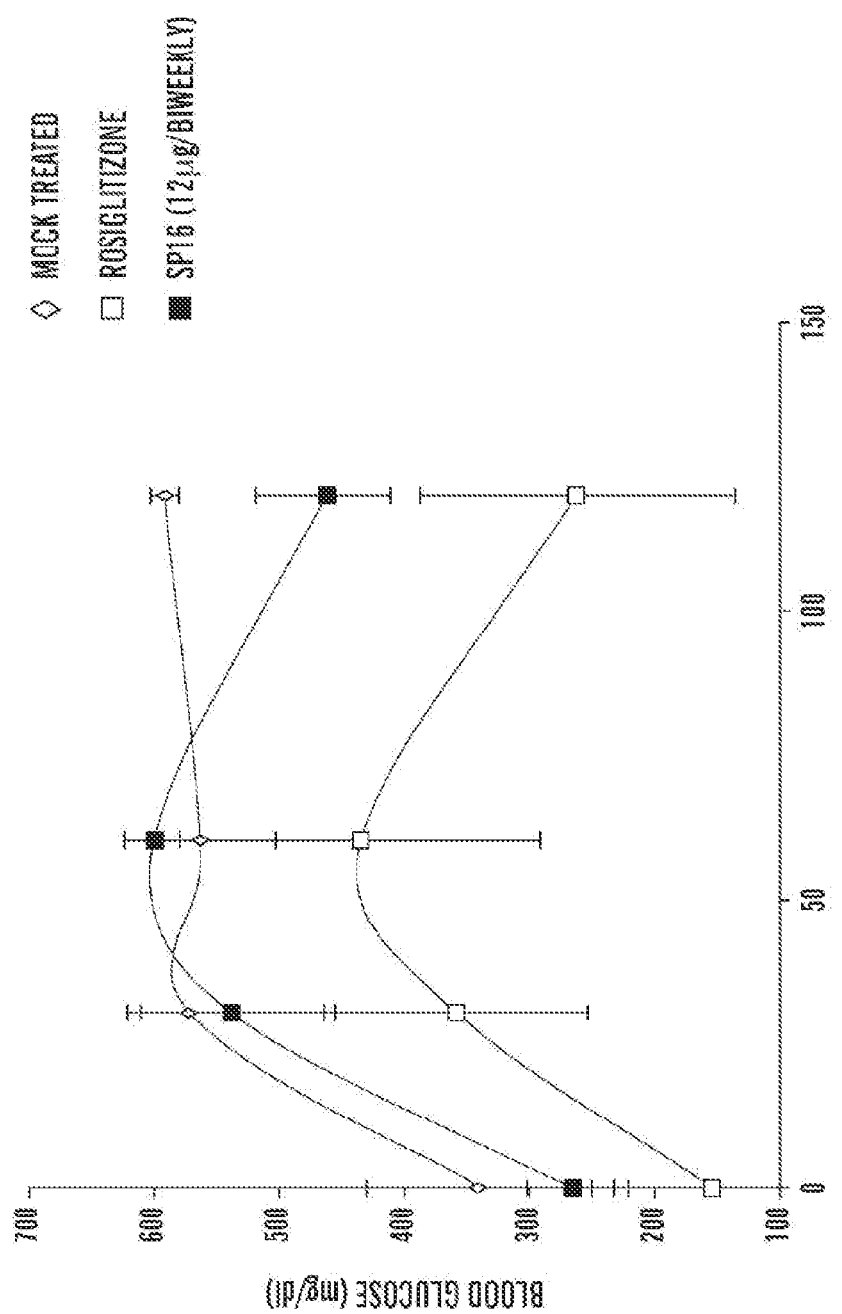

Table C (SEQ ID NOS 18-32, 1, and 33-34, respectively, in order of appearance)

| | | | |
|---|---|---|---|
| SP1 | Human AAT C36 | S I P P E | V K F N K P F V F L M I E Q N T K S P L F M G K V V N P T Q K |
| SP2 | Human KALLISTATIN (C39) | S A Q T N R H I L R F N R P F L V V I F S T S T Q S V L F L G K V V D P T K P |
| SP3 | Human Antichymotrypsin (C40) | S A L V E T R T I V R F N R P F L M I I V P T D T Q N I F F M S K V T N P K Q A |
| SP4 | Rat Serpina3M (C38) | S G R P P M I V W F N R P F L I A V S H T H G Q T I L F M A K V I N P V G A |
| SP5 | Rat Serpina3K (C38) | K S L P Q T I P L L N F N R P F M L V I T D D N G Q S V F F M G K V T N P M |
| SP6 | Human Hybrid 1 | S A Q V E T I V R F N R P F L V I I V S T N T Q |
| SP7 | Human-Rat Hybrid 1 | S I P P Q M I V W F N R P F L I A I S H T H T Q |
| SP8 | Human AAT C36 | S I P P E V K F N K P F V F L M I E Q N T K |
| SP9 | Human KALLISTATIN (C39) | S A Q T N R H I L R F N R P F L V V I F S T S T Q |
| SP10 | Human Antichymotrypsin (C40) | S A L V E T R T I V R F N R P F L M I I V P T D T Q |
| SP11 | Rat Serpina3K (C38) | K S L P Q T I P L L N F N R P F M L V I T D D N G Q |
| SP12 | Human AAT C36 | I P P E V K F N K P F V F L M I E Q N T K |
| SP13 | Human KALLISTATIN (C39) | N R H I L R F N R P F L V V I F S T S T Q |
| SP14 | Human Antichymotrypsin (C40) | T R T I V R F N R P F L M I I V P T D T Q |
| SP15 | Rat Serpina3K (C38) | T I P L L N F N R P F M L V I T D D N G Q |
| SP16 | C36 Core sequence, long | V K F N K P F V F L M I E Q N T K |
| SP17 | C36 Core sequence, short | V K F N K P F V F L M |
| SP18 | Human AAT C36 | S I P P E V K A A A A A F L M I E Q N T K |

FIG. 10A

| | | | | | | | | | | | | | | | | | | | | | TLR2 activation: |
|---|---|---|---|---|---|---|---|---|---|---|---|---|---|---|---|---|---|---|---|---|---|
| SP16 | | | | | | | | V | K | F | N | K | F | L | M | I | E | Q | N | T | K | *** |
| C36 | S | I | P | P | E | V | K | F | N | K | F | L | M | I | E | Q | N | T | K | | N/A |
| SP37 | | | | | | | A | A | A | F | N | K | F | L | M | I | E | Q | N | T | K | N/A |
| SP40 | | | | | | | V | K | A | A | A | F | L | M | I | E | Q | N | T | K | | **** |
| SP43 | | | | | | | V | K | F | N | A | A | A | M | I | E | Q | N | T | K | | * |
| SP46 | | | | | | | V | K | F | N | K | F | A | A | A | I | E | Q | N | T | K | * |
| SP49 | | | | | | | V | K | F | N | K | F | L | M | A | A | A | Q | N | T | K | ** |
| SP51 | | | | | | | V | K | F | N | K | F | L | M | I | E | A | A | A | T | K | ** |
| SP52 | | | | | | | V | K | F | N | K | F | L | M | I | E | Q | N | T | K | | *** |
| SP53 | | | | | | | A | K | F | N | K | F | L | M | I | E | Q | N | T | K | | ***** |
| SP54 | | | | | | | V | K | F | N | K | F | L | M | I | E | Q | N | T | K | | |
| SP55 | | | | | | | V | K | F | N | K | F | L | M | I | E | Q | N | A | K | | ** |
| SP56 | | | | | | | V | K | F | N | K | F | L | M | I | E | Q | N | T | A | | *** |
| SP34 | F | P | K | M | P | Q | F | N | T | E | L | K | I | F | P | E | V | N | I | K | | N/A |

FIG. 13

SEQUENCE LISTING

```
<160> NUMBER OF SEQ ID NOS: 57

<210> SEQ ID NO 1
<211> LENGTH: 17
<212> TYPE: PRT
<213> ORGANISM: Homo sapiens

<400> SEQUENCE: 1

Val Lys Phe Asn Lys Pro Phe Val Phe Leu Met Ile Glu Gln Asn Thr
1               5                   10                  15

Lys

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Val, Leu or Met
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Met, Ile or Val
<220> FEATURE:
<221> NAME/KEY: MOD_RES
<222> LOCATION: (12)..(16)
<223> OTHER INFORMATION: Any amino acid
```

-continued

<400> SEQUENCE: 2

Xaa Xaa Phe Asn Lys Pro Phe Xaa Xaa Xaa Xaa Xaa Xaa Xaa Xaa Xaa
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (5)..(5)
<223> OTHER INFORMATION: Lys or Arg
<220> FEATURE:
<221> NAME/KEY: MOD_RES
<222> LOCATION: (8)..(8)
<223> OTHER INFORMATION: Val, Leu or Met
<220> FEATURE:
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Met, Ile or Val
<220> FEATURE:
<221> NAME/KEY: MOD_RES
<222> LOCATION: (12)..(16)
<223> OTHER INFORMATION: Any amino acid
<220> FEATURE:
<221> NAME/KEY: MOD_RES
<222> LOCATION: (17)..(17)
<223> OTHER INFORMATION: Lys or Gln

<400> SEQUENCE: 3

Xaa Xaa Phe Asn Xaa Pro Phe Xaa Xaa Xaa Xaa Xaa Xaa Xaa Xaa Xaa
1               5                   10                  15

Xaa

<210> SEQ ID NO 4
<211> LENGTH: 8
<212> TYPE: PRT
<213> ORGANISM: Homo sapiens

<400> SEQUENCE: 4

Arg Phe Asn Arg Pro Phe Leu Arg
1               5

<210> SEQ ID NO 5
<211> LENGTH: 8
<212> TYPE: PRT
<213> ORGANISM: Homo sapiens

<400> SEQUENCE: 5

Arg Phe Asn Lys Pro Phe Leu Arg
1               5

<210> SEQ ID NO 6
<211> LENGTH: 28

```
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Any basic amino acid
<220> FEATURE:
<221> NAME/KEY: misc_feature
<222> LOCATION: (1)..(10)
<223> OTHER INFORMATION: This region may encompass 1, 2, 3, 4, 5, 6, 6,
      7, 8, 9, 10 or between 1 and 3, between 1 and 5, between 1 and 6,
      between 1 and 7, between 1 and 8, between 1 and 9, or between 1
      and 10 basic amino acids
<220> FEATURE:
<221> NAME/KEY: MOD_RES
<222> LOCATION: (19)..(28)
<223> OTHER INFORMATION: Any basic amino acid
<220> FEATURE:
<221> NAME/KEY: misc_feature
<222> LOCATION: (19)..(28)
<223> OTHER INFORMATION: This region may encompass 1, 2, 3, 4, 5, 6, 6,
      7, 8, 9, 10 or between 1 and 3, between 1 and 5, between 1 and 6,
      between 1 and 7, between 1 and 8, between 1 and 9, or between 1
      and 10 basic amino acids
<220> FEATURE:
<223> OTHER INFORMATION: See specification as filed for detailed
      description of substitutions and preferred embodiments

<400> SEQUENCE: 6

Xaa Xaa Xaa Xaa Xaa Xaa Xaa Xaa Xaa Xaa Arg Phe Asn Arg Pro Phe
1               5                   10                  15

Leu Arg Xaa Xaa Xaa Xaa Xaa Xaa Xaa Xaa Xaa Xaa
            20                  25

<210> SEQ ID NO 7
<211> LENGTH: 28
<212> TYPE: PRT
<213> ORGANISM: Homo sapiens
<220> FEATURE:
<221> NAME/KEY: MOD_RES
<222> LOCATION: (1)..(10)
<223> OTHER INFORMATION: Any basic amino acid
<220> FEATURE:
<221> NAME/KEY: misc_feature
<222> LOCATION: (1)..(10)
<223> OTHER INFORMATION: This region may encompass 1, 2, 3, 4, 5, 6, 6,
      7, 8, 9, 10 or between 1 and 3, between 1 and 5, between 1 and 6,
      between 1 and 7, between 1 and 8, between 1 and 9, or between 1
      and 10 basic amino acids
<220> FEATURE:
<221> NAME/KEY: MOD_RES
<222> LOCATION: (19)..(28)
<223> OTHER INFORMATION: Any basic amino acid
<220> FEATURE:
<221> NAME/KEY: misc_feature
<222> LOCATION: (19)..(28)
<223> OTHER INFORMATION: This region may encompass 1, 2, 3, 4, 5, 6, 6,
      7, 8, 9, 10 or between 1 and 3, between 1 and 5, between 1 and 6,
      between 1 and 7, between 1 and 8, between 1 and 9, or between 1
      and 10 basic amino acids
<220> FEATURE:
<223> OTHER INFORMATION: See specification as filed for detailed
      description of substitutions and preferred embodiments

<400> SEQUENCE: 7

Xaa Xaa Xaa Xaa Xaa Xaa Xaa Xaa Xaa Xaa Arg Phe Asn Lys Pro Phe
1               5                   10                  15

Leu Arg Xaa Xaa Xaa Xaa Xaa Xaa Xaa Xaa Xaa Xaa
            20                  25

<210> SEQ ID NO 8
<211> LENGTH: 12
<212> TYPE: PRT
```

-continued

<213> ORGANISM: Homo sapiens

<400> SEQUENCE: 8

Arg Arg Arg Phe Asn Arg Pro Phe Leu Arg Arg Arg
1               5                   10

<210> SEQ ID NO 9
<211> LENGTH: 12
<212> TYPE: PRT
<213> ORGANISM: Homo sapiens

<400> SEQUENCE: 9

Arg Arg Arg Phe Asn Lys Pro Phe Leu Arg Arg Arg
1               5                   10

<210> SEQ ID NO 10
<211> LENGTH: 6
<212> TYPE: PRT
<213> ORGANISM: Homo sapiens

<400> SEQUENCE: 10

Phe Asn Arg Pro Phe Leu
1               5

<210> SEQ ID NO 11
<211> LENGTH: 6
<212> TYPE: PRT
<213> ORGANISM: Homo sapiens

<400> SEQUENCE: 11

Phe Asn Lys Pro Phe Leu
1               5

<210> SEQ ID NO 12
<211> LENGTH: 17
<212> TYPE: PRT
<213> ORGANISM: Homo sapiens

<400> SEQUENCE: 12

Ala Ala Ala Asn Lys Pro Phe Val Phe Leu Met Ile Glu Gln Asn Thr
1               5                   10                  15
Lys

<210> SEQ ID NO 13
<211> LENGTH: 17
<212> TYPE: PRT
<213> ORGANISM: Homo sapiens

<400> SEQUENCE: 13

Val Lys Phe Ala Ala Ala Phe Val Phe Leu Met Ile Glu Gln Asn Thr
1               5                   10                  15
Lys

<210> SEQ ID NO 14
<211> LENGTH: 17
<212> TYPE: PRT
<213> ORGANISM: Homo sapiens

<400> SEQUENCE: 14

Val Lys Phe Asn Lys Pro Ala Ala Ala Leu Met Ile Glu Gln Asn Thr
1               5                   10                  15
Lys

<210> SEQ ID NO 15
<211> LENGTH: 17
<212> TYPE: PRT
<213> ORGANISM: Homo sapiens

<400> SEQUENCE: 15

Val Lys Phe Asn Lys Pro Phe Val Phe Ala Ala Ala Glu Gln Asn Thr
1               5                   10                  15

Lys

<210> SEQ ID NO 16
<211> LENGTH: 17
<212> TYPE: PRT
<213> ORGANISM: Homo sapiens

<400> SEQUENCE: 16

Val Lys Phe Asn Lys Pro Phe Val Phe Leu Met Ile Ala Ala Ala Thr
1               5                   10                  15

Lys

<210> SEQ ID NO 17
<211> LENGTH: 17
<212> TYPE: PRT
<213> ORGANISM: Homo sapiens

<400> SEQUENCE: 17

Val Lys Phe Asn Lys Pro Phe Val Phe Leu Met Ile Glu Gln Ala Ala
1               5                   10                  15

Ala

<210> SEQ ID NO 18
<211> LENGTH: 36
<212> TYPE: PRT
<213> ORGANISM: Homo sapiens

<400> SEQUENCE: 18

Ser Ile Pro Pro Glu Val Lys Phe Asn Lys Pro Phe Val Phe Leu Met
1               5                   10                  15

Ile Glu Gln Asn Thr Lys Ser Pro Leu Phe Met Gly Lys Val Val Asn
            20                  25                  30

Pro Thr Gln Lys
        35

<210> SEQ ID NO 19
<211> LENGTH: 39
<212> TYPE: PRT
<213> ORGANISM: Homo sapiens

<400> SEQUENCE: 19

Ser Ala Gln Thr Asn Arg His Ile Leu Arg Phe Asn Arg Pro Phe Leu
1               5                   10                  15

Val Val Ile Phe Ser Thr Ser Thr Gln Ser Val Leu Phe Leu Gly Lys
            20                  25                  30

Val Val Asp Pro Thr Lys Pro
        35

<210> SEQ ID NO 20
<211> LENGTH: 40
<212> TYPE: PRT
<213> ORGANISM: Homo sapiens

<400> SEQUENCE: 20

Ser Ala Leu Val Glu Thr Arg Thr Ile Val Arg Phe Asn Arg Pro Phe
1               5                   10                  15

Leu Met Ile Ile Val Pro Thr Asp Thr Gln Asn Ile Phe Phe Met Ser
            20                  25                  30

Lys Val Thr Asn Pro Lys Gln Ala
        35                  40

<210> SEQ ID NO 21
<211> LENGTH: 38
<212> TYPE: PRT
<213> ORGANISM: Rattus sp.

<400> SEQUENCE: 21

Ser Gly Arg Pro Pro Met Ile Val Trp Phe Asn Arg Pro Phe Leu Ile
1               5                   10                  15

Ala Val Ser His Thr His Gly Gln Thr Ile Leu Phe Met Ala Lys Val
            20                  25                  30

Ile Asn Pro Val Gly Ala
        35

<210> SEQ ID NO 22
<211> LENGTH: 38
<212> TYPE: PRT
<213> ORGANISM: Rattus sp.

<400> SEQUENCE: 22

Lys Ser Leu Pro Gln Thr Ile Pro Leu Leu Asn Phe Asn Arg Pro Phe
1               5                   10                  15

Met Leu Val Ile Thr Asp Asp Asn Gly Gln Ser Val Phe Phe Met Gly
            20                  25                  30

Lys Val Thr Asn Pro Met
        35

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Gln Val Glu Thr Ile Val Arg Phe Asn Arg Pro Phe Leu Val
1               5                   10                  15

Ile Ile Val Ser Thr Asn Thr Gln
            20

<210> SEQ ID NO 24
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ile Pro Pro Gln Met Ile Val Trp Phe Asn Arg Pro Phe Leu Ile
1               5                   10                  15

Ala Ile Ser His Thr His Thr Gln
            20

<210> SEQ ID NO 25
<211> LENGTH: 22
<212> TYPE: PRT
<213> ORGANISM: Homo sapiens

<400> SEQUENCE: 25

Ser Ile Pro Pro Glu Val Lys Phe Asn Lys Pro Phe Val Phe Leu Met
1               5                   10                  15

Ile Glu Gln Asn Thr Lys
            20

<210> SEQ ID NO 26
<211> LENGTH: 25
<212> TYPE: PRT
<213> ORGANISM: Homo sapiens

<400> SEQUENCE: 26

Ser Ala Gln Thr Asn Arg His Ile Leu Arg Phe Asn Arg Pro Phe Leu
1               5                   10                  15

Val Val Ile Phe Ser Thr Ser Thr Gln
            20                  25

<210> SEQ ID NO 27
<211> LENGTH: 26
<212> TYPE: PRT
<213> ORGANISM: Homo sapiens

<400> SEQUENCE: 27

Ser Ala Leu Val Glu Thr Arg Thr Ile Val Arg Phe Asn Arg Pro Phe
1               5                   10                  15

Leu Met Ile Ile Val Pro Thr Asp Thr Gln
            20                  25

<210> SEQ ID NO 28
<211> LENGTH: 26
<212> TYPE: PRT
<213> ORGANISM: Rattus sp.

<400> SEQUENCE: 28

Lys Ser Leu Pro Gln Thr Ile Pro Leu Leu Asn Phe Asn Arg Pro Phe
1               5                   10                  15

Met Leu Val Ile Thr Asp Asp Asn Gly Gln
            20                  25

<210> SEQ ID NO 29
<211> LENGTH: 21
<212> TYPE: PRT
<213> ORGANISM: Homo sapiens

<400> SEQUENCE: 29

Ile Pro Pro Glu Val Lys Phe Asn Lys Pro Phe Val Phe Leu Met Ile
1               5                   10                  15

Glu Gln Asn Thr Lys
            20

<210> SEQ ID NO 30
<211> LENGTH: 21
<212> TYPE: PRT
<213> ORGANISM: Homo sapiens

<400> SEQUENCE: 30

Asn Arg His Ile Leu Arg Phe Asn Arg Pro Phe Leu Val Val Ile Phe

```
                1               5                  10                 15
Ser Thr Ser Thr Gln
                20

<210> SEQ ID NO 31
<211> LENGTH: 21
<212> TYPE: PRT
<213> ORGANISM: Homo sapiens

<400> SEQUENCE: 31

Thr Arg Thr Ile Val Arg Phe Asn Arg Pro Phe Leu Met Ile Ile Val
1               5                   10                  15

Pro Thr Asp Thr Gln
                20

<210> SEQ ID NO 32
<211> LENGTH: 21
<212> TYPE: PRT
<213> ORGANISM: Rattus sp.

<400> SEQUENCE: 32

Thr Ile Pro Leu Leu Asn Phe Asn Arg Pro Phe Met Leu Val Ile Thr
1               5                   10                  15

Asp Asp Asn Gly Gln
                20

<210> SEQ ID NO 33
<211> LENGTH: 11
<212> TYPE: PRT
<213> ORGANISM: Homo sapiens

<400> SEQUENCE: 33

Val Lys Phe Asn Lys Pro Phe Val Phe Leu Met
1               5                   10

<210> SEQ ID NO 34
<211> LENGTH: 22
<212> TYPE: PRT
<213> ORGANISM: Homo sapiens

<400> SEQUENCE: 34

Ser Ile Pro Pro Glu Val Lys Ala Ala Ala Ala Ala Phe Leu Met
1               5                   10                  15

Ile Glu Gln Asn Thr Lys
                20

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Val, Leu or Met
<220> FEATURE:
```

-continued

```
<221> NAME/KEY: MOD_RES
<222> LOCATION: (9)..(10)
<223> OTHER INFORMATION: Any amino acid
<220> FEATURE:
<221> NAME/KEY: MOD_RES
<222> LOCATION: (11)..(11)
<223> OTHER INFORMATION: Met, Ile or Val
<220> FEATURE:
<221> NAME/KEY: MOD_RES
<222> LOCATION: (12)..(16)
<223> OTHER INFORMATION: Any amino acid

<400> SEQUENCE: 35

Xaa Xaa Phe Asn Arg Pro Phe Xaa Xaa Xaa Xaa Xaa Xaa Xaa Xaa
1               5                   10                  15

Gln

<210> SEQ ID NO 36
<211> LENGTH: 9
<212> TYPE: PRT
<213> ORGANISM: Homo sapiens

<400> SEQUENCE: 36

Phe Leu Met Ile Glu Gln Asn Thr Lys
1               5

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 37

His His His His His His
1               5

<210> SEQ ID NO 38
<211> LENGTH: 23
<212> TYPE: PRT
<213> ORGANISM: Homo sapiens

<400> SEQUENCE: 38

Arg Arg Arg Val Lys Phe Asn Lys Pro Phe Val Phe Leu Met Ile Glu
1               5                   10                  15

Gln Asn Thr Lys Arg Arg Arg
            20

<210> SEQ ID NO 39
<211> LENGTH: 17
<212> TYPE: PRT
<213> ORGANISM: Homo sapiens

<400> SEQUENCE: 39

Arg Arg Arg Val Lys Phe Asn Lys Pro Phe Val Phe Leu Met Arg Arg
1               5                   10                  15

Arg

<210> SEQ ID NO 40
<211> LENGTH: 17
<212> TYPE: PRT
<213> ORGANISM: Homo sapiens

<400> SEQUENCE: 40
```

Leu Arg Phe Asn Arg Pro Phe Leu Val Val Ile Phe Ser Thr Ser Thr
1               5                   10                  15

Gln

<210> SEQ ID NO 41
<211> LENGTH: 11
<212> TYPE: PRT
<213> ORGANISM: Homo sapiens

<400> SEQUENCE: 41

Leu Arg Phe Asn Arg Pro Phe Leu Val Val Ile
1               5                   10

<210> SEQ ID NO 42
<211> LENGTH: 23
<212> TYPE: PRT
<213> ORGANISM: Homo sapiens

<400> SEQUENCE: 42

Arg Arg Arg Leu Arg Phe Asn Arg Pro Phe Leu Val Val Ile Phe Ser
1               5                   10                  15

Thr Ser Thr Gln Arg Arg Arg
            20

<210> SEQ ID NO 43
<211> LENGTH: 17
<212> TYPE: PRT
<213> ORGANISM: Homo sapiens

<400> SEQUENCE: 43

Arg Arg Arg Leu Arg Phe Asn Arg Pro Phe Leu Val Val Ile Arg Arg
1               5                   10                  15

Arg

<210> SEQ ID NO 44
<211> LENGTH: 17
<212> TYPE: PRT
<213> ORGANISM: Homo sapiens

<400> SEQUENCE: 44

Val Arg Phe Asn Arg Pro Phe Leu Met Ile Ile Val Pro Thr Asp Thr
1               5                   10                  15

Gln

<210> SEQ ID NO 45
<211> LENGTH: 11
<212> TYPE: PRT
<213> ORGANISM: Homo sapiens

<400> SEQUENCE: 45

Val Arg Phe Asn Arg Pro Phe Leu Met Ile Ile
1               5                   10

<210> SEQ ID NO 46
<211> LENGTH: 23
<212> TYPE: PRT
<213> ORGANISM: Homo sapiens

<400> SEQUENCE: 46

Arg Arg Arg Val Arg Phe Asn Arg Pro Phe Leu Met Ile Ile Val Pro
1               5                   10                  15

Thr Asp Thr Gln Arg Arg Arg

```
<210> SEQ ID NO 47
<211> LENGTH: 17
<212> TYPE: PRT
<213> ORGANISM: Homo sapiens

<400> SEQUENCE: 47

Arg Arg Arg Val Arg Phe Asn Arg Pro Phe Leu Met Ile Ile Arg Arg
1               5                   10                  15

Arg

<210> SEQ ID NO 48
<211> LENGTH: 8
<212> TYPE: PRT
<213> ORGANISM: Homo sapiens

<400> SEQUENCE: 48

Val Arg Phe Asn Arg Pro Phe Leu
1               5

<210> SEQ ID NO 49
<211> LENGTH: 14
<212> TYPE: PRT
<213> ORGANISM: Homo sapiens

<400> SEQUENCE: 49

Arg Arg Arg Val Arg Phe Asn Arg Pro Phe Leu Arg Arg Arg
1               5                   10

<210> SEQ ID NO 50
<211> LENGTH: 21
<212> TYPE: PRT
<213> ORGANISM: Homo sapiens

<400> SEQUENCE: 50

Ile Pro Pro Glu Val Lys Ala Ala Ala Ala Ala Phe Leu Met Ile
1               5                   10                  15

Glu Gln Asn Thr Lys
            20

<210> SEQ ID NO 51
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Phe Pro Lys Met Val Pro Gln Phe Asn Thr Glu Leu Lys Ile Phe Pro
1               5                   10                  15

Glu Val Asn Ile Lys
            20

<210> SEQ ID NO 52
<211> LENGTH: 17
<212> TYPE: PRT
<213> ORGANISM: Homo sapiens

<400> SEQUENCE: 52

Ala Lys Phe Asn Lys Pro Phe Val Phe Leu Met Ile Glu Gln Asn Thr
1               5                   10                  15
```

Lys

<210> SEQ ID NO 53
<211> LENGTH: 17
<212> TYPE: PRT
<213> ORGANISM: Homo sapiens

<400> SEQUENCE: 53

Val Ala Phe Asn Lys Pro Phe Val Phe Leu Met Ile Glu Gln Asn Thr
1               5                   10                  15

Lys

<210> SEQ ID NO 54
<211> LENGTH: 17
<212> TYPE: PRT
<213> ORGANISM: Homo sapiens

<400> SEQUENCE: 54

Val Lys Ala Asn Lys Pro Phe Val Phe Leu Met Ile Glu Gln Asn Thr
1               5                   10                  15

Lys

<210> SEQ ID NO 55
<211> LENGTH: 17
<212> TYPE: PRT
<213> ORGANISM: Homo sapiens

<400> SEQUENCE: 55

Val Lys Phe Asn Lys Pro Phe Val Phe Leu Met Ile Glu Gln Asn Ala
1               5                   10                  15

Lys

<210> SEQ ID NO 56
<211> LENGTH: 17
<212> TYPE: PRT
<213> ORGANISM: Homo sapiens

<400> SEQUENCE: 56

Val Lys Phe Asn Lys Pro Phe Val Phe Leu Met Ile Glu Gln Asn Thr
1               5                   10                  15

Ala

<210> SEQ ID NO 57
<211> LENGTH: 17
<212> TYPE: PRT
<213> ORGANISM: Artificial Sequence
<220> FEATURE:
<223> OTHER INFORMATION: Description of Artificial Sequence: Synthetic
      consensus sequence
<220> FEATURE:
<221> NAME/KEY: MOD_RES
<222> LOCATION: (1)..(1)
<223> OTHER INFORMATION: Val or Leu
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Val, Leu or Met
<220> FEATURE:
<221> NAME/KEY: MOD_RES
<222> LOCATION: (9)..(10)
<223> OTHER INFORMATION: Any amino acid
<220> FEATURE:

```
<221> NAME/KEY: MOD_RES
<222> LOCATION: (11)..(11)
<223> OTHER INFORMATION: Met, Ile or Val
<220> FEATURE:
<221> NAME/KEY: MOD_RES
<222> LOCATION: (12)..(16)
<223> OTHER INFORMATION: Any amino acid

<400> SEQUENCE: 57

Xaa Xaa Phe Asn Lys Pro Phe Xaa Xaa Xaa Xaa Xaa Xaa Xaa Xaa
1               5                   10                  15

Gln
```

PEPTIDES AND METHODS OF USING SAME

CROSS-REFERENCE TO RELATED APPLICATIONS

This application is a divisional application under 35 U.S.C. § 121 of a co-pending U.S. application Ser. No. 13/925,067, which is a continuation-in-part application of an International Application No. PCT/US13/20498 filed Jan. 7, 2013, which claims benefit under 35 U.S.C. § 119(e) of provisional application No. 61/584,517 filed Jan. 9, 2012 and provisional application No. 61/699,571 filed Sep. 11, 2012, the contents of which are incorporated herein by reference in their entirety.

SEQUENCE LISTING

The instant application contains a Sequence Listing, which has been submitted in ASCII format via EFS-Web and is hereby incorporated by reference in its entirety. Said ASCII copy, created on Dec. 31, 2012, is named 65292741.txt and is 18,884 bytes in size.

FIELD OF THE INVENTION

The present disclosure presents isolated and/or synthesized peptides. Specifically, the present invention is a class of isolated and/or synthesized peptide fragments, and synthetic analogs based on the peptide fragments. The peptides can have preventative and therapeutic effects in human disease and can be used in treatment of human disease.

BACKGROUND

Serine protease inhibitors (Serpins) represent a large (>1000) family of protease inhibitors, present in all branches of life and involved in a multitude of physiological processes. In mammals, such as humans, Serpins are important for homeostasis and although a certain level of promiscuity exists, each Serpin has a cognate serine protease(s). For example, alpha-1-antitrypsin (AAT) and alpha-1-antichymotrypsin (ACT) inhibit inflammatory proteases such as elastase, whereas antithrombin inhibits thrombin and plays a role in coagulation.

A number of specific AAT mutations are manifested in human disease, including COPD, thrombosis and Serpinopathies (cirrhosis and dementia). Currently, a small number of human serum-derived AAT formulations are approved by the FDA for treatment of COPD. In this therapeutic approach, AAT functions as a protease inhibitor similar to endogenous AAT.

AAT is the archetypical Serpin and shares tertiary structure with other Serpins. Serpins have a ~20 amino acid (aa) exposed loop, called the reactive center loop (RCL), which serves as bait for the cognate proteases. Once the protease binds the RCL, it becomes trapped, partially unfolded and destined for degradation. The cleavage of the RCL at its P1-P1' site drives the process of protease inactivation and results in the release of a small C-terminal peptide from the Serpin molecule.

SUMMARY

We have unexpectedly found that many of the C-terminal peptides from the Serpin molecule and variants and derivatives thereof function as potent anti-inflammatory agents. Accordingly, we provide peptide compositions, pharmaceutical compositions comprising the C-terminal Serpin peptides and methods of using the peptides to treat inflammatory and autoimmune conditions including type II diabetes, lupus and graft versus host disease, uveitis, eczema and psoriasis, cystic fibrosis, rheumatoid arthritis (RA), acute radiation syndrome and burn patients, inflammatory bowel disease (IBD) and new onset type I diabetes.

The invention is based on our finding that a short peptide, SP16 (SEQ ID NO: 1) derived from human alpha-1-antitrypsin shows anti-inflammatory and immune-modulatory properties similar to the much larger parent protein, alpha-1-antitrypsin. Without wishing to be bound by a theory, SP16 appears to be a first-in-class peptide master switch for treatment of autoimmune, inflammatory and metabolic diseases.

Specifically, we have shown the function of the SP16 peptide consisting of an amino acid sequence VKFNKPFVFLMIEQNTK (SEQ ID NO: 1) in well-established animal models for at least type II diabetes, rheumatoid arthritis, and lethal endotoxemia.

Accordingly, we provide a composition comprising an isolated peptide comprising, consisting essentially of, or consisting of the amino acid sequence X1-Z1-F-N-K-P-F-X2-Z2-X3-Z3-Q (SEQ ID NO: 2), wherein
X1 is V or L;
X2 is V, L or M;
X3 is M, I or V;
Z1 is any amino acid;
Z2 is a sequence of any two amino acids; and
Z3 is a sequence any five amino acids, and wherein the isolated peptide consists of 37 or fewer amino acids.

The peptide can be modified to extend the shelf life and/or bioavailability using one or more non-natural peptide bonds or amino acids or by attaching to the peptide functional groups such as, e.g., polyethylene glycol (PEG).

The composition may further comprise a carrier, such as a pharmaceutically acceptable carrier.

The peptides of the invention can be used to reduce the serum TNF-α levels in human individuals who have pathologically increased TNF-α levels. Thus the invention provides a method or use for reducing TNF-α levels in a human in need thereof comprising administering to the human individual the peptide of the invention in a pharmaceutically acceptable carrier. In certain embodiments, the isolated peptide results in a 50% or 75% decrease in serum TNF-α levels when administered in an effective amount to a human subject compared to the levels before administration of the isolated polypeptide. In other embodiments, the isolated peptide further comprises at least one other protein. The combination of the at least two proteins can be referred to as a fusion protein. The other protein can be selected from an epitope tag and a half-life extender. The peptide can comprise both an epitope tag and a half-life extender.

We also provides a composition comprising an isolated peptide consisting essentially of or consisting of the amino acid sequence X1-Z1-F-N-X2-P-F-X3-Z2-X4-Z3-X5 (SEQ ID NO: 3), wherein
X1 is V or L;
X2 is K or R;
X3 is V, L or M;
X4 is M, I or V;
X5 is K or Q;
Z1 is any amino acid;
Z2 is a sequence of any two amino acids;
Z3 is a sequence any five amino acids; and
wherein the isolated peptide causes a 75% decrease in serum TNF-α levels when administered in an effective amount to a human subject compared to the amount of TNF-α levels before administering the peptide.

In certain embodiments, the isolated peptide comprises the amino acid sequence X1-Z1-F-N-X2-P-F-X3-Z2-X4-Z3-X5 (SEQ ID NO: 3), wherein X1, X2, X3, X4, X5, Z1, Z2, and Z3 are defined as above and wherein the peptide consists of, at most, 35, 22 or 21 amino acid residues.

In certain aspects, the peptides of any of the embodiments described herein and throughout the specification, also comprise at least one other protein. The combination of these at least two proteins can be referred to as a fusion protein. Specifically the other protein can be selected from an epitope tag and a half-life extender. In some aspects of all the embodiments of the invention, the isolated peptide can comprise both an epitope tag and a half-life extender.

The disclosure also provides an isolated peptide consisting essentially of or consisting of the amino acid sequence RFNRPFLR (SEQ ID NO: 4) and RFNKPFLR (SEQ ID NO: 5). In certain embodiments, the isolated peptide causes a 50% or 75% decrease in serum TNF-α levels compared to the amount of TNF-α levels before administering the peptide when administered in an effective amount to a human subject.

In other aspects of all the embodiments of the invention, the isolated peptide is linked another protein. The combination of these proteins can be referred to as a fusion protein. Specifically the other protein can be selected an epitope tag and a half-life extender.

In some aspects of all the embodiments of the invention, the isolated peptide consists of, at most, 100, 35, 22, 21 or 9 additional amino acids.

In other embodiments, the isolated peptide consists essentially of, or consists of the amino acid sequence of Z1-RFNRPFLR-Z2 (SEQ ID NO: 6) and Z1-RFNKPFLR-Z2 (SEQ ID NO: 7), wherein Z1 and Z2 are independently 1, 2, 3, 4, 5, 6, 6, 7, 8, 9, 10 or between 1 and 3, between 1 and 5, between 1 and 6, between 1 and 7, between 1 and 8, between 1 and 9, or between 1 and 10 basic amino acids.

In some embodiments, the isolated peptide consists essentially of or consists of the amino acid sequence of RRRFNRPFLRRR (SEQ ID NO: 8) and RRRFNKPFLRRR (SEQ ID NO: 9).

The disclosure also provides a composition comprising an isolated peptide consisting essentially of or consisting of the amino acid sequence of FNRPFL (SEQ ID NO: 10) and FNKPFL (SEQ ID NO: 11).

The disclosure also provide a composition comprising an isolated or synthesized peptide consisting essentially of or consisting of any one or a combination of the following peptides: SP40; SP43; SP46; and SP49 as set forth in Table B, and their use in methods for treating inflammation, rheumatoid arthritis, COPD, cystic fibrosis, improving glycemic control in diabetic subjects and preventing and treating endotoxemia, for example, in burn victims and subjects exposed to acute radiation.

In one embodiment, the disclosure also provides a method of decreasing serum TNF-α compared to the amount of TNF-α levels before administering the peptide to a subject comprising administering to the subject an effective amount of any one of the isolated peptides as defined above to decrease the serum TNF-α levels by at least 50%. In one embodiment, serum TNF-α levels are decreased by 75% compared to the amount of TNF-α levels before administering the peptide. In other embodiments, the subject is a mammal. In some aspects of all the embodiments of the invention, the mammal is a human.

In some embodiments, the disclosure provides methods of improving glycemic control or reducing hyperglycemia in a subject in need thereof comprising administering to the subject with hyperglycemia any of the peptides described herein in a pharmaceutically acceptable carrier.

In some aspects of all the embodiments of the invention, the human has been diagnosed with type II diabetes, new onset type I diabetes, rheumatoid arthritis, COPD, cystic fibrosis, uveitis, eczema, psoriasis, lupus, graft versus host disease, inflammatory bowel disease (IBD), or endotoxemia following acute radiation exposure or burn prior to administering the peptide.

In some aspects, the human has not been subjected to prior treatment with alpha antitrypsin, such as alpha-1-antitrypsin treatment before the treatment with the peptides of the invention.

BRIEF DESCRIPTION OF THE DRAWINGS

FIG. 1 is a table showing the sequences and homology of Serpin C-terminal peptides (SEQ ID NOs: 18-24, respectively, in order of appearance).

FIG. 2 is a table showing peptides derived from truncations (SEQ ID NOs: 25-32, 1, 33-34, 1, 33, 38-51, 10, and 8, respectively, in order of appearance).

FIGS. 8A-8F show graphs summarizing data from a study in the db/db T2DM model. Five-week old db/db mice were assigned to groups of 10 animals, and IP injected with 0.6 mg/kg SP16 (biweekly), 15 mg/kg Rosiglitazone (biweekly), or vehicle control for 5 weeks. HbA1c (FIG. 8A) and C-peptide (FIG. 8B) levels were determined at the end of the study. During the last week of the study, a glucose tolerance test was administered (FIG. 8C). Non-fasted blood glucose was measured twice a week throughout the study and was significantly lowered in the SP16 (SEQ ID NO: 1) and Rosiglitazone groups. Values represent averages, with standard errors indicated. (*) indicates P<0.05 and (**) p<0.01, compared to the Mock group by a T-test. FIG. 8D summarizes the extent of islet hyperplasia in the db/db study as assessed by morphometry. FIGS. 8E and 8F summarize serum CRP and TGF-beta levels in the db/db mouse model of type II diabetes. Decreased serum CRP levels are consistent with peptide treatment promoting an anti-inflammatory cytokine profile. Eight week old diabetic db/db mice were assigned to groups of 8. Group received Saline (Mock) or 0.6 mg/kg SP16 biweekly for 12 weeks. Pooled serum CRP and TGF-beta levels were determined for each group. (*) indicates $p<0.05$ and (**) $p<0.01$ compared to the Vehicle control group.

FIGS. 10A and B. FIG. 10A presents exemplary peptides that were used to reduce TNF-alpha levels in mice subjected to an LPS challenge.

FIG. 13 shows Structure activity relationship analysis for SP16. Table showing the amino acid sequences (SEQ ID NOS 1, 18, 12-17, 52-56, and 51, respectively, in order of appearance) of peptides that were tested using a TLR-2 indicator cell line (See data in previous figure). The right side of the table summarizes the peptides' impact on TLR-2 signaling (* indicates low, ***** indicates high, N/A had no impact on signaling) The data suggest the first three residues contribute to inducing TLR-2 signaling. If residues 1-3 are substituted with alanines (SP37), the mutant peptide has no impact on TLR2. However, when substituted individually (SP52-SP54), the peptides retain the ability to stimulate TLR-2. Surprisingly, substitution of the phenyl alanine residue at position 3 with a smaller alanine residue enhances the ability to stimulate TLR-2 signaling compared to SP16.

DETAILED DESCRIPTION

Figure 3:
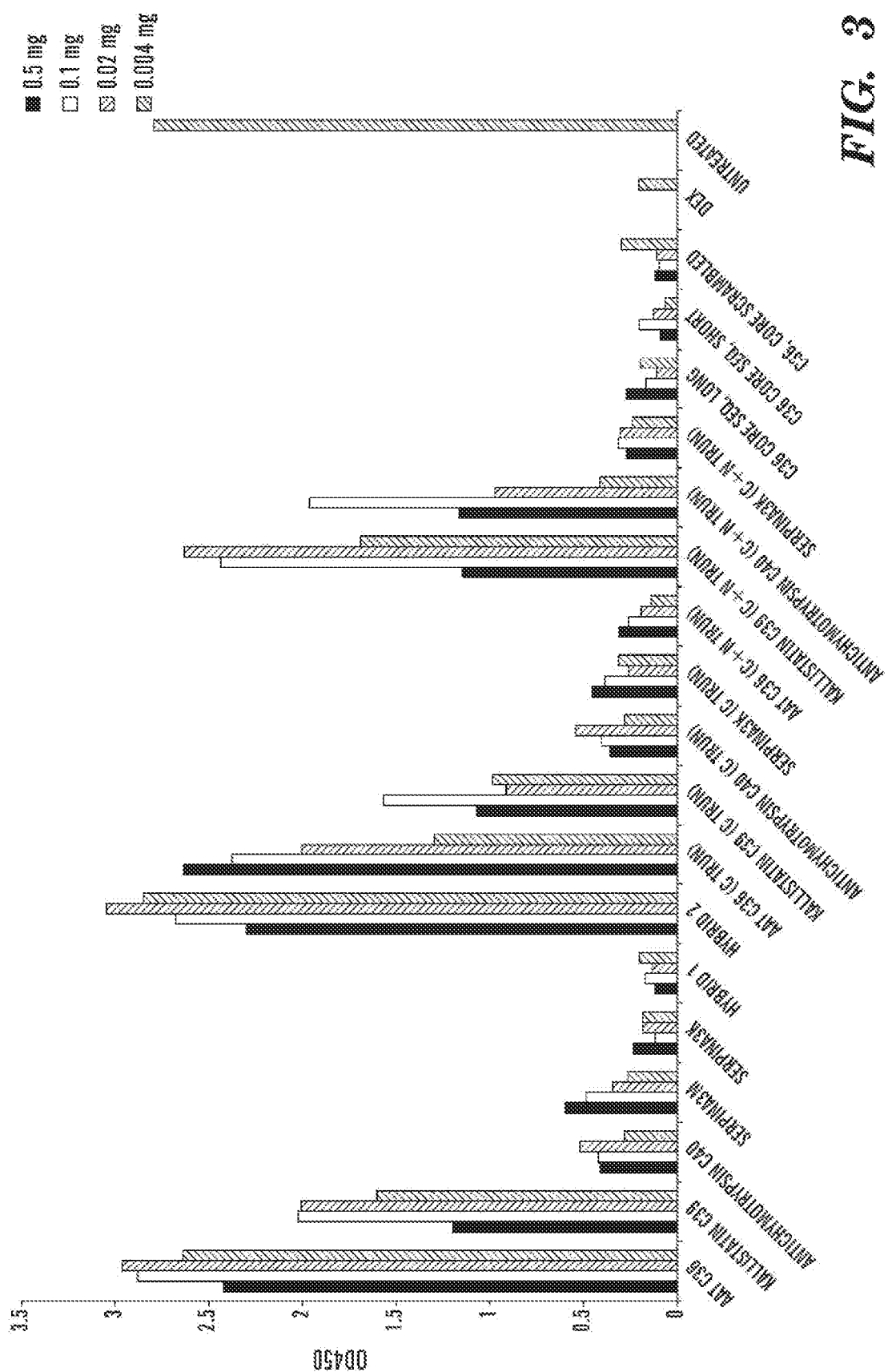
FIG. 3 is a bar graph showing TNF-α levels in blood of mice injected with 0.5, 0.1, 0.02 or 0.004 mg of various peptides (SP1-SP18 from left to right on the x-axis). Each peptide was administered in four different concentrations. The four bars for each of the peptide from left to right represent the concentrations from highest (0.5 mg) to the lowest (0.004 mg).

The present disclosure describes isolated peptides used and useful in the field of disease treatment and prevention. Specifically, the present invention provides isolated and/or synthesized peptides, and synthetic analogs based on these peptides, with preventative and therapeutic effects in human disease. For example, the peptides may be used to treat or prevent inflammation, auto-immune tissue destruction, e.g., in lupus and host versus graft disease, rheumatoid arthritis, cystic fibrosis, eczema, psoriasis and to treat type II and type I diabetes, for example to stimulate expansion of beta cell mass in an individual with diabetes, to treat inflammatory bowel disease as well as to treat or prevent endotoxemia following acute radiation exposure and in burn patients.

The peptides described herein are specifically defined short isolated or synthesized C-terminal peptides based on Serpins and variants and derivatives thereof with surprisingly effective anti-inflammatory properties and with much more useful size for therapeutic applications compared to the native Serpin proteins. The isolated peptides are shown in FIGS. 1-2. FIG. 1 shows the amino acid sequences of the C-terminal fragments of a variety of Serpins. Each peptide is marked with a SEQ ID NO: in column 2, immediately to the left of the peptide. FIG. 2 shows truncations of the C-terminal fragments shown in FIG. 1, as well as variants and derivatives thereof. Again, each peptide is marked with a SEQ ID NO: in column 2, immediately next to the peptide.

We have discovered that SP16 (SEQ ID NO: 1), which is derived from human alpha-antitrypsin exhibits anti-inflammatory and immune-modulatory properties similar to those of the parent protein, alpha-1-antitrypsin. SP16 appears to be a first-in-class peptide master switch for treatment of auto-immune, inflammatory and metabolic diseases. Without wishing to be bound by a theory, the peptides of the invention can provide a good safety profile, based on the good safety profile of the parent protein, alpha-1-antitrypsin. However, the peptides of the invention are far easier and thus less expensive to produce as they are much smaller than the parent protein.

We have discovered that C-terminal peptides that result from a Serpin molecule's cleavage by one of its cognate serine proteases have intrinsic biologic function that is distinct from that of the protease inhibitor function of the parent, complete Serpin molecule. For example, the C-terminal peptides from AAT, antichymotrypsin and Kallistatin have varying degrees of anti-inflammatory effects. Based on our research, we submit that these anti-inflammatory and/or immune modulating peptides, that are a byproduct from the lifecycle of a Serpin molecule, represent a type of an immunological and inflammatory (homeostatic) "master switch."

Moreover, our data from engineered cell lines show that SP16 activates the TLR-2 signaling pathway. This is interesting because another immune modulating peptide, Dia-Pep277, which shares no sequence similarity with SP16, has a similar TLR activation profile. Without wishing to be bound by a theory, based on these observations, we suggest that SP16 acts through the TLR2 receptor, and possible the T-cell receptor, to drive cytokine secretion to a Th2 anti-inflammatory cytokine profile (IL-4 and IL-10). In autoimmune diseases, SP16 is predicted to induce expansion of regulatory T-cell populations and thereby shift the inflammatory response towards a regulatory response.

We therefore provide novel anti-inflammatory molecules from the C-terminal peptides of Serpin molecules, and novel ways of developing additional anti-inflammatory molecules by modifying the C-terminal fragments of Serpins.

The previously known functions of Serpins are related to inhibiting the function of serine protease enzymes. A few Serpins inhibit other types of proteins, and several do not have an inhibitory function.

Serpins are a large family (>1000) of Serine Protease Inhibitors that are structurally similar but functionally diverse. They are involved in a multitude of physiological processes and are critical for homeostasis in mammals. Genetic mutations in individual Serpins are manifested in different human diseases, including COPD, thrombosis and emphysema.

Each serpin with an inhibitory role is responsible for blocking the activity of one or more proteins. Serpins bind to their target proteins to prevent them from completing any further reactions. Upon binding to a target, an irreversible change in the structure of a serpin protein occurs. Certain cells recognize when a Serpin is bound to its target and clear these attached proteins from the bloodstream.

Alpha-1-antitrypsin (AAT) is the prototypical Serpin. PROLASTIN® (Talecris), ZEMAIRA® (Aventis Behring) and ARALAST® (Baxter) are human serum-derived AAT formulations approved by the FDA for treatment of COPD. AAT is currently in clinical trials for treatment of new onset type I diabetes, graft vs. host disease and cystic fibrosis.

Researchers have identified at least 37 different serpin genes in humans. Based on our research, we submit that isolated and synthesized C-terminal fragments of the serpins proteins provide a novel source of anti-inflammatory molecules. Thus, we submit that the C-terminal fragments of at least the Serpins listed in Table A are useful as anti-inflammatory molecules.

TABLE A

| Approved Symbol | Approved Name | Synonyms |
| --- | --- | --- |
| SERPINA1 | serpin peptidase inhibitor, clade A (alpha-1 antiproteinase, antitrypsin), member 1 | AAT, A1A, PI1, alpha-1-antitrypsin, A1AT, alpha1AT |
| SERPINA2 | serpin peptidase inhibitor, clade A (alpha-1 antiproteinase, antitrypsin), member 2 | ATR, ARGS |
| SERPINA3 | serpin peptidase inhibitor, clade A (alpha-1 antiproteinase, antitrypsin), member 3 | ACT, alpha-1-antichymotrypsin |
| SERPINA4 | serpin peptidase inhibitor, clade A (alpha-1 antiproteinase, antitrypsin), member 4 | KST, KAL, KLST, kallistatin |
| SERPINA5 | serpin peptidase inhibitor, clade A (alpha-1 antiproteinase, antitrypsin), member 5 | PAI3, PROCI |
| SERPINA6 | serpin peptidase inhibitor, clade A (alpha-1 antiproteinase, antitrypsin), member 6 | |
| SERPINA7 | serpin peptidase inhibitor, clade A (alpha-1 antiproteinase, antitrypsin), member 7 | |
| AGT | angiotensinogen (serpin peptidase inhibitor, clade A, member 8) | |
| SERPINA9 | serpin peptidase inhibitor, clade A (alpha-1 antiproteinase, antitrypsin), member 9 | CENTERIN, SERPINA11b, GCET1 |
| SERPINA10 | serpin peptidase inhibitor, clade A (alpha-1 antiproteinase, antitrypsin), member 10 | PZI, ZPI |
| SERPINA11 | serpin peptidase inhibitor, clade A (alpha-1 antiproteinase, antitrypsin), member 11 | |
| SERPINA12 | serpin peptidase inhibitor, clade A (alpha-1 antiproteinase, antitrypsin), member 12 | OL-64, Vaspin |

TABLE A-continued

| Approved Symbol | Approved Name | Synonyms |
|---|---|---|
| SERPINA13 | serpin peptidase inhibitor, clade A (alpha-1 antiproteinase, antitrypsin), member 13 (pseudogene) | UNQ6121 |
| SERPINB1 | serpin peptidase inhibitor, clade B (ovalbumin), member 1 | EI, PI2, anti-elastase |
| SERPINB2 | serpin peptidase inhibitor, clade B (ovalbumin), member 2 | HsT1201 |
| SERPINB3 | serpin peptidase inhibitor, clade B (ovalbumin), member 3 | T4-A, HsT1196 |
| SERPINB4 | serpin peptidase inhibitor, clade B (ovalbumin), member 4 | PI11, LEUPIN, SCCA-2, SCCA1 |
| SERPINB5 | serpin peptidase inhibitor, clade B (ovalbumin), member 5 | maspin |
| SERPINB6 | serpin peptidase inhibitor, clade B (ovalbumin), member 6 | PTI, CAP |
| SERPINB7 | serpin peptidase inhibitor, clade B (ovalbumin), member 7 | MEGSIN |
| SERPINB8 | serpin peptidase inhibitor, clade B (ovalbumin), member 8 | CAP2 |
| SERPINB9 | serpin peptidase inhibitor, clade B (ovalbumin), member 9 | CAP3 |
| SERPINB10 | serpin peptidase inhibitor, clade B (ovalbumin), member 10 | bomapin |
| SERPINB11 | serpin peptidase inhibitor, clade B (ovalbumin), member 11 (gene/pseudogene) | EPIPIN |
| SERPINB12 | serpin peptidase inhibitor, clade B (ovalbumin), member 12 | YUKOPIN |
| SERPINB13 | serpin peptidase inhibitor, clade B (ovalbumin), member 13 | HUR7, hurpin, headpin |
| SERPINC1 | serpin peptidase inhibitor, clade C (antithrombin), member 1 | ATIII, MGC22579 |
| SERPIND1 | serpin peptidase inhibitor, clade D (heparin cofactor), member 1 | HC-II, HLS2, HC2, D22S673 |
| SERPINE1 | serpin peptidase inhibitor, clade E (nexin, plasminogen activator inhibitor type 1), member 1 | PAI |
| SERPINE2 | serpin peptidase inhibitor, clade E (nexin, plasminogen activator inhibitor type 1), member 2 | PN1, GDN, PNI, nexin |
| SERPINE3 | serpin peptidase inhibitor, clade E (nexin, plasminogen activator inhibitor type 1), member 3 | |
| SERPINF1 | serpin peptidase inhibitor, clade F (alpha-2 antiplasmin, pigment epithelium derived factor), member 1 | EPC-1, PIG35 |
| SERPINF2 | serpin peptidase inhibitor, clade F (alpha-2 antiplasmin, pigment epithelium derived factor), member 2 | API, ALPHA-2-PI, A2AP, AAP |
| SERPING1 | serpin peptidase inhibitor, clade G (C1 inhibitor), member 1 | C1IN, C1-INH, HAE1, HAE2 |
| SERPINH1 | serpin peptidase inhibitor, clade H (heat shock protein 47), member 1, (collagen binding protein 1) | HSP47, colligen |
| SERPINI1 | serpin peptidase inhibitor, clade I (neuroserpin), member 1 | neuroserpin |
| SERPINI2 | serpin peptidase inhibitor, clade I (pancpin), member 2 | PANCPIN, TSA2004, MEPI, pancpin |

We further performed an alanine screen that showed that isolated or synthesized or modified SP16 peptides shown in Table B below are particularly effective in reducing TNF-alpha levels in a mouse model for inflammation. Specifically, we discovered that in these particular fragments, the three most N-terminal and the two most C-terminal amino acids appear to play a role in the anti-inflammatory properties of the peptides as replacement of them appeared to reduce the capacity of the peptides to reduce TNF-alpha levels in a LPS challenged mouse model of sepsis (FIG. 10). Accordingly, in some aspects of all embodiments of the invention the peptides are selected from SP40, SP43, SP46, and SP49 the peptide sequences of which are set forth in Table B.

Table B shows peptides named SP16; SP40; SP43; SP46; and SP49 provided particularly good anti-inflammatory effect when administered to a mouse model of sepsis (See FIG. 10).

TABLE B

| Peptide | Amino Acid Sequence |
|---|---|
| SP16 | V K F N K P F V F L M I E Q N T K (SEQ ID NO: 1) |
| SP37 | A A A N K P F V F L M I E Q N T K (SEQ ID NO: 12) |

TABLE B-continued

| | Peptide Amino Acid Sequence |
|---|---|
| SP40 | V K F A A A F V F L M I E Q N T K (SEQ ID NO: 13) |
| SP43 | V K F N K P A A A L M I E Q N T K (SEQ ID NO: 14) |
| SP46 | V K F N K P F V F A A A E Q N T K (SEQ ID NO: 15) |
| SP49 | V K F N K P F V F L M I A A A T K (SEQ ID NO: 16) |
| SP51 | V K F N K P F V F L M I E Q A A A (SEQ ID NO: 17) |

According to some embodiments and aspects of the invention, any of isolated peptides consisting of or consisting essentially of sequences set forth in SEQ ID NOs: 8, 10, 19-34, and 38-49 can be used to reduce inflammation. Any of peptides consisting of or consisting essentially of sequences set forth SEQ ID NOs: 8, 10, 19-34, and 38-49 can also be used to reduce TNF-α in a subject. In certain embodiments, the amount of TNF-α in the serum is reduced by up to 50% or more or 75% or more compared to the amount of the same in the serum prior to administering the peptide.

Figure 10B:
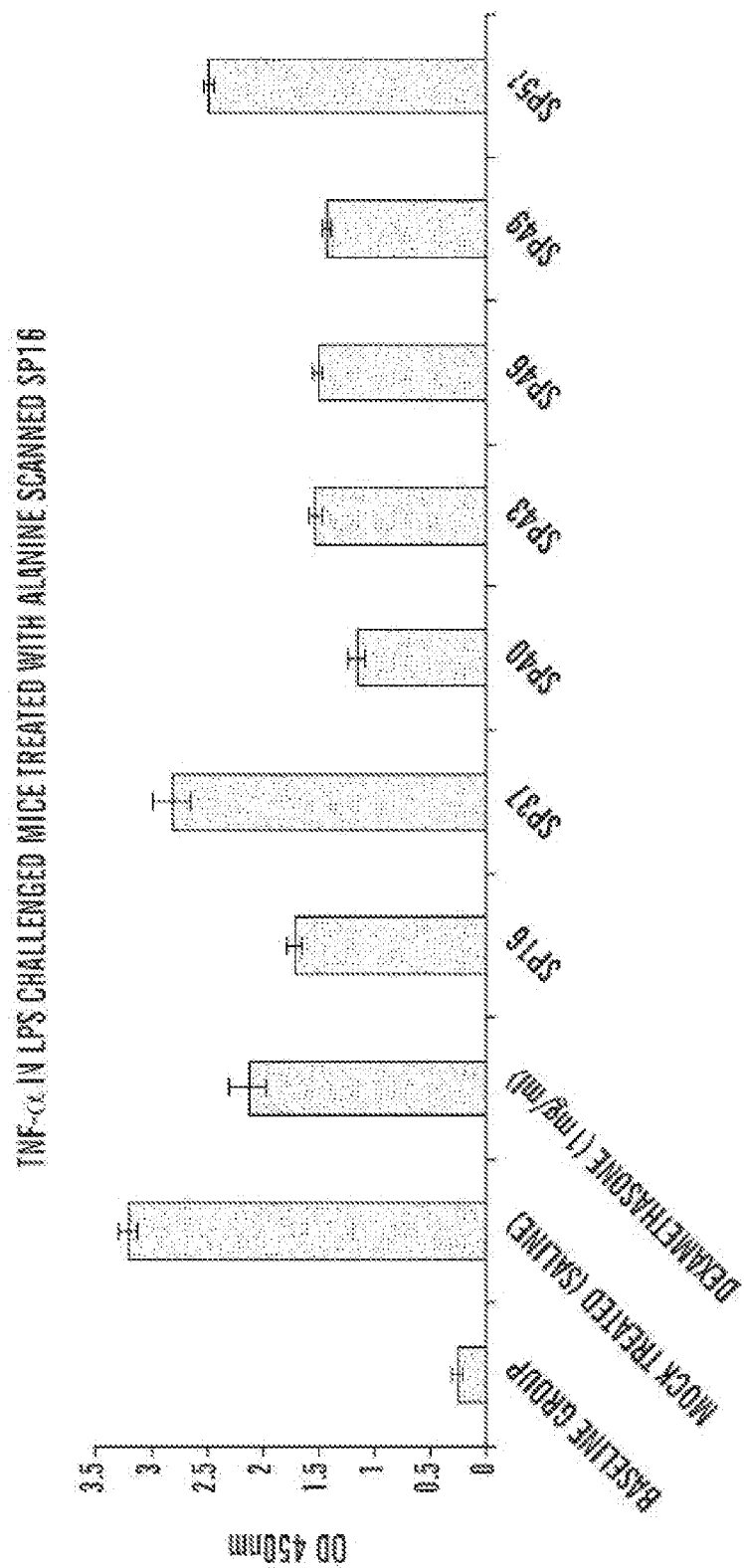
FIG. 10B shows TNF-alpha levels in LPS challenged mice. The mice were treated with alanine scanned SP16 peptide. Dexamethasone served as positive control of "effective treatment" and the peptides SP16, SP40, SP43, SP46 and SP49 all reduce TNF-alpha levels more than Dexamethasone. Based on this alanine screen, and without wishing to be bound by a theory, it appears that the C- and N-terminal amino acids contribute to the anti-inflammatory effect of the SP16 peptide. Compare to FIG. 4 which shows a graph summarizing serum TNF-alpha levels in a mouse inflammation model, LPS challenge, treated with different human Serpin derived peptides. Groups of 3 animals were injected with 0.2 mg/kg peptide and subjected to LPS challenge. Serum TNF-alpha levels were determined by ELISA. Several peptides provided the same level of protection as 1 mg/kg Dexamethasone.

Table C, provided at FIG. 10A, presents additional exemplary peptides that were used to reduce TNF-alpha levels in mice subjected to an LPS challenge. See also FIG. 10B. The peptides with capacity to reduce TNF-alpha levels as shown in FIG. 10B are contemplated for the compositions, pharmaceutical compositions and methods of use and treatment of inflammatory conditions in the present invention.

SP1 (SEQ ID NO: 18); SP2 (SEQ ID NO: 19); SP3 (SEQ ID NO: 20); SP4 (SEQ ID NO: 21); SP5 (SEQ ID NO: 22); SP6 (SEQ ID NO: 23); SP7 (SEQ ID NO: 24); SP8 (SEQ ID NO: 25); SP9 (SEQ ID NO: 26); SP10 (SEQ ID NO: 27); SP11 (SEQ ID NO: 28); SP12 (SEQ ID NO: 29); SP13 (SEQ ID NO: 30); SP14 (SEQ ID NO: 31); SP15 (SEQ ID NO: 32); SP16 (SEQ ID NO: 1); SP17 (SEQ ID NO: 33); SP18 (SEQ ID NO: 34).

The phrase "consisting essentially of" is herein meant to define the scope of the peptides to the specified material amino acids, and to only include additional amino acids or changes that do not materially affect the claimed invention's basic and novel characteristics, namely, the anti-inflammatory capacity of the short isolated or synthesized peptides. The definition specifically excludes peptides that have a sequence of a complete Serpin protein, and the definition also specifically excludes peptide sequences that are equal to or longer than 37 amino acids of any naturally occurring Serpin protein.

Without wishing to be bound by a theory, we have also identified the important amino acids that provide the core, and the possible modifications, for anti-inflammatory peptides as manufactured herein. Therefore, the isolated peptides encompassed by the formulae set forth below are also provided and they can be used to reduce inflammation.

Human AAT, antichymotrypsin, and kallistatin have been known to contain elements with anti-inflammatory properties. However, these elements have not been previously identified. We have now established a new family of human Serpin-derived peptides with potent anti-inflammatory effect using, e.g., a mouse endotoxemia model (LPS induced endotoxemia). Based on the efficacy of the peptides in the mouse inflammation model, the peptide size, and the safety profile of the parent protein, the AAT-based peptides, the peptides, such as SP16, and fragments and derivatives thereof provide a novel and improved molecule to treat inflammation in humans.

Formula I provides a composition comprising a peptide comprising, consisting essentially of or consisting of the amino acid sequence X1-Z1-F-N-R-P-F-X2-Z2-X3-Z3-Q (SEQ ID NO:35) and X1-Z1-F-N-K-P-F-X2-Z2-X3-Z3 (SEQ ID NO: 2) wherein
X1 is V or L;
X2 is V, L or M;
X3 is M, I or V;
Z1 is any amino acid;
Z2 is a sequence of any two amino acids; and
Z3 is a sequence any five amino acids, wherein the peptide comprises 37 or fewer amino acids.

In certain aspects of all the embodiments, the isolated peptide causes a 50% or 75% decrease in serum TNF-α levels compared to the serum level as measured prior to administering the isolated peptide, when administered in an effective amount to a human subject. In some aspects of all the embodiments of the invention, the peptide further comprises a fusion protein. The fusion protein can be selected from an epitope tag and a half-life extender or a combination thereof.

In certain aspects of all the embodiments, the isolated peptide causes improvement in glycemic control in diabetic subjects, as measured using, e.g., A1C test, fasting plasma glucose test (FPG), and/or the oral glucose tolerance test (OGTT). Pre-diabetic individuals typically score at or above 5.7% to under 6.5% on the A1C test, whereas diabetics score over 6.5% on this test. Pre-diabetic individuals also typically score at or over 100 mg/dl to under 126 mg/dl using the FPG test whereas diabetics score over 126 mg/dl. Pre-diabetic individuals typically score at or over 140 to under 200 mg/dl using the OGTT test whereas diabetic individuals score over 200 mg/dl.

Formula II provides a composition comprising an isolated peptide comprising, consisting essentially of or consisting of the amino acid sequence X1-Z1-F-N-X2-P-F-X3-Z2-X4-Z3-X5 (SEQ ID NO: 3), wherein
X1 is V or L;
X2 is K or R;
X3 is V, L or M;
X4 is M, I or V;
X5 is K or Q;
Z1 is any amino acid;
Z2 is a sequence of any two amino acids;
Z3 is a sequence any five amino acids; and wherein the isolated peptide causes a 75% decrease in serum TNF-α levels compared to the serum levels prior to administering the isolated peptide when administered in an effective amount to a human subject.

In certain embodiments, the peptide comprising the amino acid sequence of X1-Z1-F-N-X2-P-F-X3-Z2-X4-Z3-X5 (SEQ ID NO: 3) as defined above, includes, at most, 35, 22 or 21 amino acid residues. In certain aspects of all the embodiments of the invention, the peptide further comprises a fusion protein. Specifically the fusion protein can be selected from an epitope tag and a half-life extender or a combination thereof.

In some aspects of all the methods and uses of the invention, the peptide is SP16.

Therefore, the invention also provides an isolated peptide consisting of or consisting essentially of the amino acid sequence RFNRPFLR (SEQ ID NO: 4) and RFNKPFLR (SEQ ID NO: 5), which can also be used for the treatment of inflammation. In certain embodiments, the peptide causes a 50% or 75% decrease in serum TNF-α levels compared to the serum TNF-α levels prior to administering the isolated peptide when administered in an effective amount to a human subject. In some aspects of all the embodiments of the invention, the isolated peptide further comprises a fusion protein. Specifically the fusion protein can be selected from an epitope tag and a half-life extender. In other embodiments, the isolated peptide comprises, at most, 100, 35, 22, 21, 16 or 9 amino. In other embodiments, the isolated peptide comprises the amino acid sequence of Z1-RFNRP-FLR-Z2 (SEQ ID NO: 6), and Z1-RFNKPFLR-Z2 (SEQ ID NO: 7) wherein Z1 and Z2 are independently between 1, 2, 3, 4, 5, 6, 6, 7, 8, 9, 10 or between 1 and 3, between 1 and 5, between 1 and 6, between 1 and 7, between 1 and 8, between 1 and 9, or between 1 and 10 basic amino acids.

In some aspects of all the embodiments of the invention, the isolated peptide consists essentially of or consists of the amino acid sequence of RRRFNRPFLRRR (SEQ ID NO: 8) and RRRFNKPFLRRR (SEQ ID NO: 9). The disclosure also provides a composition comprising a peptide consisting essentially of or consisting of the amino acid sequence of FNRPFL (SEQ ID NO: 10) and FNKPFL (SEQ ID NO: 11).

In certain embodiments the isolated peptide comprises 5 or more sequential amino acids from the amino acid sequence of FLMIEQNTK (SEQ ID NO: 36). These peptides can be used to reduce inflammation or reduce TNF-α level in a subject. In certain embodiments, the amount of TNF-α level in the serum is reduced compared to the amount of TNF-α in the serum prior to administering the isolated peptide. In certain embodiments, the glycemic control is improved as measured using tests such as A1C test, fasting plasma glucose test (FPG), and the oral glucose tolerance test (OGTT). Also, both TNF-α level and glycemic control can be used when measuring improvement in a diabetic individual.

In some aspects, the method of treatment of inflammation further comprises analysis of TNF-α serum levels prior to administering the isolated peptide and after administering the isolated peptide. If the TNF-α serum level is decreased less than 30%, the step of administering can be repeated with the same dose or with a larger dose of the peptide compared to the first dose.

Fragments of any of the peptides described above can vary in size. For example, these fragments can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, or 37, amino acids in length.

The peptides described above are generally used to reduce inflammation. The peptides exert anti-inflammatory and immune-modulating effects, and additionally, directly or indirectly stimulate beta cell regeneration. In certain embodiments, these peptides reduce inflammation by reducing the activity or expression of TNF-α. The activity of TNF-α can be reduced by 10, 15, 20, 25, 30, 35, 40, 45, 50, 55, 60, 65, 70, 75, 80, 85, 90, 95, 99 or 100%. The expression of TNF-α can be reduced 10, 15, 20, 25, 30, 35, 40, 45, 50, 55, 60, 65, 70, 75, 80, 85, 90, 95, 99 or 100%. When administered therapeutically, the peptide composition typically further comprises a pharmaceutically acceptable solution or carrier.

The peptides described above can also be used to treat, prevent or improve the symptoms of several pathologies. These pathologies include inflammation, auto-immune tissue destruction and hyperglycemia. The peptides described above can also be used to stimulate expansion of beta cell mass in an individual with diabetes, treatment of cystic fibrosis, and in treatment or prevention of endotoxemia following acute radiation exposure and in burn patients.

Accordingly, the disclosure further provides methods of treating inflammation comprising the step of administering any one of the peptides described herein or a combination thereof to a subject in need of treatment of inflammation. In some aspects, the subject has not been treated with alpha-antitrypsin prior to the treatment. In some aspects, the method comprises a step of assaying whether the individual has increased serum TNF-α levels and if the subject has increased serum TNF-α levels then administering the peptide to the subject, and if not, then not administering the peptide to the subject.

The disclosure also enables methods of preventing development of inflammation comprising the step of administering any one of the peptides or a combination thereof to a subject in need of prevention of inflammation. In some aspects, the subject has not been treated with alpha-antitrypsin prior to the treatment. In some aspects, the method comprises a step of assaying whether the individual has increased serum TNF-α levels and if the subject has increased serum TNF-α levels then administering the peptide to the subject, and if not, then not administering the peptide to the subject.

The disclosure also enables methods of preventing autoimmune tissue destruction comprising the step of administering any one of the peptides or a combination thereof to a subject in need of prevention of autoimmune tissue destruction. In some aspects, the subject has not been treated with alpha-antitrypsin prior to the treatment. In some aspects, the method comprises a step of assaying whether the individual has increased serum TNF-α levels and if the subject has increased serum TNF-α levels then administering the peptide to the subject, and if not, then not administering the peptide to the subject.

The disclosure also enables methods of improving glycemic control in individuals having diabetes comprising the step of administering any one of the peptides or a combination thereof to a subject in need of prevention of autoimmune tissue destruction. In some aspects, the subject has not been treated with alpha-antitrypsin prior to the treatment. In some aspects, the method comprises a step of assaying whether the individual has improved glycemic control by e.g., A1C test, fasting plasma glucose test, and/or the oral glucose tolerance test or any other known test for measuring the functioning of glycemic control.

In one embodiment, the disclosure provides use of any one or a combination of the isolated or synthesized peptides for the treatment of inflammation, and inflammation wherein the TNF-α level is increased.

In certain aspects of all the embodiments, inflammation is related to diabetes type 1 or 2, rheumatoid arthritis or COPD.

For example, the Examples provided herein, demonstrate that the peptides disclosed herein are efficacious in treating both type I and type II diabetes. For example, when SP16 is administered to db/db mice, a recognized type II diabetes model animal, non-fasted blood glucose and HbA1c levels were lowered, while serum c-peptide levels increased, and glucose tolerance was improved in response to the peptides (see, e.g., FIG. 8A-8F). This demonstrates that the peptide described herein improves glycemic control in type II diabetes. As a further example, when NOD mice, a recognized model of type I diabetes were administered with peptides as described herein, the development of type I diabetes was delayed and/or prevented as demonstrated in FIG. 18. The Examples include peptide administration by intraperitoneal injection as well as by oral gavage, demonstrating that oral administration is suitable for delivering the peptides of the invention. Without wishing to be bound by a theory, we suggest that, the peptides, such as SP16, work by oral administration via the gut associated lymphoid tissue (GALT).

Again, without wishing to the bound by a theory, we suggest that TLR2 agonism or TLR4 signaling by the peptides disclosed herein, such as SP16, can be used to induce expansion of gut Tregs, enabling oral immunotherapy using the peptides of the invention.

The invention also provides methods for treatment and prevention of cystic fibrosis and endotoxemia following acute radiation exposure and in burn patients using any one or a combination of the peptides of the invention.

For convenience, certain terms employed in the entire application (including the specification, examples, and appended claims) are defined throughout the specification. Unless defined otherwise, all technical and scientific terms used herein have the same meaning as commonly understood by one of ordinary skill in the art to which this invention belongs.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild-type polynucleotide sequence or any change in a wild-type protein sequence. Although it is often assumed that a change in the genetic material results in a change of the function of the protein, the term—"mutant" refers to a change in the sequence of a wild-type protein regardless of whether that change alters the function of the protein (e.g., increases, decreases, imparts a new function), or whether that change has no effect on the function of the protein (e.g., the mutation or variation is silent). The term mutation is used interchangeably herein with polymorphism in this application.

The terms "polypeptide" and "protein" are used interchangeably to refer to an isolated polymer of amino acid residues, and are not limited to a minimum length unless otherwise defined. Peptides, oligopeptides, dimers, multimers, and the like, are also composed of linearly arranged amino acids linked by peptide bonds, and whether produced biologically and isolated from the natural environment, produced using recombinant technology, or produced synthetically typically using naturally occurring amino acids.

In some aspects, the polypeptide or protein is a "modified polypeptide" comprising non-naturally occurring amino acids. In some aspects, the polypeptides comprise a combination of naturally occurring and non-naturally occurring amino acids, and in some embodiments, the peptides comprise only non-naturally occurring amino acids.

In some aspects of all the embodiments of the invention, the peptides or modified peptides further comprise co-translational and post-translational (C-terminal peptide cleavage) modifications, such as, for example, disulfide-bond formation, glycosylation, acetylation, phosphorylation, proteolytic cleavage (e.g., cleavage by furins or metalloproteases), and the like to the extent that such modifications do not affect the anti-inflammatory properties of the isolated peptides or their capacity to improve glycemic control.

In some aspects of the invention, the polypeptide is altered. The term "altered polypeptide" refers to a peptide that includes alterations, such as deletions, additions, and substitutions (generally conservative in nature as would be known to a person in the art, such as alanines), to the native sequence, as long as the protein maintains the desired activity, i.e., it anti-inflammatory activity of capacity to improve glycemic control or reduce hyperglycemia. These modifications can be deliberate, as through site-directed mutagenesis, or can be accidental, such as through mutations of artificial hosts, such as genetically engineered bacteria, yeast or mammalian cells, that produce the proteins, or errors due to PCR amplification or other recombinant DNA methods. Polypeptides or proteins are composed of linearly arranged amino acids linked by peptide bonds, but in contrast to peptides, have a well-defined conformation. Proteins, as opposed to peptides, generally consist of chains of 50 or more amino acids.

The term "peptide" as used herein typically refers to a sequence of amino acids made up of a single chain of amino acids joined by peptide bonds. Generally, peptides contain at least two amino acid residues and are less than about 50 amino acids in length, unless otherwise defined.

"Modified peptide" may include the incorporation of non-natural amino acids into the peptides of the invention, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. Therefore, in some embodiments the peptides as disclosed comprise L and D amino acids, wherein no more than 1, 2, 3, 4, 5, 6, 7, 8, 9, or 10 D-amino acids are included. In certain aspects, the peptides comprise more than 10 D-amino acids, and in certain aspects all the amino acids of the peptides are D-amino acids.

In yet a further aspect, the peptides or fragments or derivatives thereof can be "retro-inverso peptides." A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous α-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., Int J Pept Protein Res. 24(6):553-6 (1984); Verdini, A and Viscomi, G. C, J. Chem. Soc. Perkin Trans. 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

The term "substantial identity" as used herein denotes a characteristic of a polynucleotide or amino acid sequence, wherein the polynucleotide or amino acid comprises a sequence that has at least 85% sequence identity, preferably at least 90% to 95% sequence identity, more usually at least 99% sequence identity as compared to a reference sequence over a comparison window of at least 18 nucleotide (6 amino acid) positions, frequently over a window of at least 24-48 nucleotide (8-16 amino acid positions, wherein the percentage of sequence identity is calculated by comparing the reference sequence to the sequence which can include deletions or additions which total 20 percent or less of the reference sequence over the comparison window. The reference sequence can be a subset of a larger sequence. The term "similarity", when used to describe a polypeptide, is determined by comparing the amino acid sequence and the conserved amino acid substitutes of one polypeptide to the sequence of a second polypeptide.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60 at least 70%, at least 80%, at least 90%, at least 95% identical, at least 97% identical, or at least 99% identical. Determination of homologs of the genes or peptides of the present invention can be easily ascertained by the skilled artisan.

The term "substantially homologous" refers to sequences that are at least 90%, at least 95% identical, at least 96%, identical at least 97% identical, at least 98% identical or at least 99% identical. Homologous sequences can be the same functional gene in different species. Determination of homologs of the genes or peptides of the present invention can be easily ascertained by the skilled artisan.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith and Waterman (Adv. Appl. Math. 2:482 (1981), which is incorporated by reference herein), by the homology alignment algorithm of Needleman and Wunsch (J. MoI. Biol. 48:443-53 (1970), which is incorporated by reference herein), by the search for similarity method of Pearson and Lipman (Proc. Natl. Acad. Sci. USA 85:2444-48 (1988), which is incorporated by reference herein), by computerized implementations of these algorithms (e.g., GAP, BESTFIT, FASTA, and TFASTA in the Wisconsin Genetics Software Package, Genetics Computer Group, 575 Science Dr., Madison, Wis.), or by visual inspection. (See generally Ausubel et al. (eds.), Current Protocols in Molecular Biology, 4th ed., John Wiley and Sons, New York (1999)).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng and Doolittle (J. MoI. Evol. 25:351-60 (1987), which is incorporated by reference herein). The method used is similar to the method described by Higgins and Sharp (Comput. Appl. Biosci. 5:151-53 (1989), which is incorporated by reference herein). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and sequence similarity is the BLAST algorithm, which is described by Altschul et al. (J. MoI. Biol. 215:403-410 (1990), which is incorporated by reference herein). (See also Zhang et al., Nucleic Acid Res. 26:3986-90 (1998); Altschul et al., Nucleic Acid Res. 25:3389-402 (1997), which are incorporated by reference herein). Software for performing BLAST analyses is publicly available through the National Center for Biotechnology Information internet web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a word length (W) of 11, the BLOSUM62 scoring matrix (see Henikoff and Henikoff, Proc. Natl. Acad. Sci. USA 89:10915-9 (1992), which is incorporated by reference herein) alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin and Altschul, Proc. Natl. Acad. Sci. USA 90:5873-77 (1993), which is incorporated by reference herein). One measure of similarity provided by the BLAST algorithm is the smallest sum probability (P(N)), which provides an indication of the probability by which a match between two nucleotide or amino acid sequences would occur by chance. For example, an amino acid sequence is considered similar to a reference amino acid sequence if the smallest sum probability in a comparison of the test amino acid to the reference amino acid is less than about 0.1, more typically less than about 0.01, and most typically less than about 0.001.

The term "variant" as used herein refers to a peptide or nucleic acid that differs from the polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

Variants can also be synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. MoI Biol, 1999, 217, 721-739 and Taylor et al, J. Theor. Biol. 119(1986); 205-218 and S. French and B. Robson, J. MoI. Evol. 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

The term "derivative" as used herein refers to peptides which have been chemically modified, for example but not limited to by techniques such as ubiquitination, labeling, pegylation (derivatization with polyethylene glycol), lipidation, glycosylation, or addition of other molecules. A molecule also a "derivative" of another molecule when it contains additional chemical moieties not normally a part of the molecule. Such moieties can improve the molecule's solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, Pa. (1990), incorporated herein, by reference, in its entirety.

Thus, in certain aspects of all the embodiments of the invention, the peptides of the invention comprise peptide derivatives, such as pegylated peptides.

The term "functional" when used in conjunction with "derivative" or "variant" refers to a peptide of the invention which possesses a biological activity (either functional or structural) that is substantially similar to a biological activity of the entity or molecule it is a functional derivative or functional variant thereof, i.e., anti-inflammatory activity in the context of the peptides described herein. The term functional derivative is intended to include the fragments, analogues or chemical derivatives of a molecule.

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

An "analog" of a molecule such as a peptide refers to a molecule similar in function to either the entire molecule or to a fragment thereof. The term "analog" is also intended to include allelic species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond. In some aspects of all the embodiments of the invention, the fusion peptides are covalently bonded.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6 (SEQ ID NO: 37), digoxigenin, FITC, Cy3, Cy5, green fluorescent protein, V5 epitope tags, GST, β-galactosidase, AU1, AU5, and avidin. Half-life extenders include Fc domain and serum albumin.

The terms "subject" and "individual" and "patient" are used interchangeably herein, and refer to an animal, for example a human or non-human animal (e.g., a mammal), to whom treatment, including prophylactic treatment, with a pharmaceutical composition as disclosed herein, is provided. The term "subject" as used herein refers to human and non-human animals. The term "non-human animals" includes all vertebrates, e.g., mammals, such as non-human primates, (particularly higher primates), sheep, dogs, rodents (e.g. mouse or rat), guinea pigs, goats, pigs, cats, rabbits, cows, and non-mammals such as chickens, amphibians, reptiles etc. In one embodiment, the subject is human. In another embodiment, the subject is an experimental animal or animal substitute as a disease model. Non-human mammals include mammals such as non-human primates, (particularly higher primates), sheep, dogs, rodents (e.g. mouse or rat), guinea pigs, goats, pigs, cats, rabbits and cows. In some aspects, the non-human animal is a companion animal such as a dog or a cat.

"Treating" a disease or condition in a subject or "treating" a patient having a disease or condition refers to subjecting the individual to a pharmaceutical treatment, e.g., the administration of a drug, such that at least one symptom of the disease or condition is decreased or stabilized. Typically, when the peptide is administered therapeutically as a treatment, it is administered to a subject who presents with one or more symptoms of inflammation.

The term "prevention" is used in connection of prevention of symptoms or slowing down of symptom development from the time of asymptomatic state. Typically, when the peptide is administered preventively, it is administered to a subject who does not present imminent symptoms of inflammation. Typically, the subject is at risk of developing inflammation, such as diabetes or COPD, due to the family history, laboratory results, genetic testing or life-style. In some aspects, the "prevention" relates to administering the peptides to burn victims or people that have been subjected to acute radiation exposure prior to them developing endotoxemia because these subjects are at risk of developing endotoxemia as a result of tissue damage caused by a burn or radiation.

By "specifically binds" or "specific binding" is meant a compound or antibody that recognizes and binds a desired polypeptide but that does not substantially recognize and bind other molecules in a sample, for example, a biological sample, which naturally includes a polypeptide of the invention. Specific binding can be characterized by a dissociation constant of at least about $1 \times 10^{-6}$ M or smaller. In other embodiments, the dissociation constant is at least about $1 \times 10^{-7}$ M, $1 \times 10^{-8}$ M, or $1 \times 10^{-9}$ M. Methods for determining whether two molecules specifically bind are well known in the art and include, for example, equilibrium dialysis, surface plasmon resonance, and the like.

By "isolated" it is meant that the polypeptide has been separated from any natural environment, such as a body fluid, e.g., blood, and separated from the components that naturally accompany the peptide.

By isolated and "substantially pure" is meant a polypeptide that has been separated and purified to at least some degree from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

By a "decrease" or "inhibition" used in the context of the level of, for example TNF-alpha levels refers to reduction of the amount of protein in the biological sample, such as blood or tissue sample, a cell, a cell extract, or a cell supernatant. For example, such a decrease may be due to reduced RNA stability, transcription, or translation, increased protein degradation, or RNA interference. Preferably, this decrease is at least about 5%, at least about 10%, at least about 25%, at least about 50%, at least about 75%, at least about 80%, or even at least about 90% compared to a reference value.

The term "reference value" in the context of the claims and the application refers typically to an abnormally high TNF-alpha level found in an individual affected with or suffering from inflammation. The reference value is typically the amount of TNF-alpha in the individual prior to administering of the peptide of the invention. In some aspects of all the embodiments concerning glycemic control, the term "reference value" refers to the numeric values used in measuring glycemic control in a subject. There are a number of tests which can be used to determine if, e.g., a human subject is affected with pre-diabetes. Such tests include, e.g., the A1C test, fasting plasma glucose test (FPG), and the oral glucose tolerance test (OGTT). Examples of reference values using these methods follow: Pre-diabetic individuals typically score at or above 5.7% to under 6.5% on the A1C test, whereas diabetics score over 6.5% on this test. Pre-diabetic individuals also typically score at or over 100 mg/dl to under 126 mg/dl using the FPG test whereas diabetics score over 126 mg/dl. Pre-diabetic individuals typically score at or over 140 to under 200 mg/dl using the OGTT test whereas diabetic individuals score over 200 mg/dl. Thus, referring to a normoglycemic reference value, one can use the following cut-off numbers when measuring is performed using the above-mentioned tests: A1C test—under 5.7%; FPG test under 100 mg/dl; and OGTT under 140 mg/dl.

By an "increase" in the expression or activity of a gene or protein is meant a positive change in protein or nucleic acid level or activity in a cell, a cell extract, or a cell supernatant. For example, such an increase may be due to increased RNA stability, transcription, or translation, or decreased protein degradation. Preferably, this increase is at least 5%, at least about 10%, at least about 25%, at least about 50%, at least about 75%, at least about 80%, at least about 100%, at least about 200%, or even about 500% or more over the level of expression or activity under control conditions.

The term "recombinant" as used herein to describe a nucleic acid molecule, means a polynucleotide of genomic, cDNA, viral, semisynthetic, and/or synthetic origin, which, by virtue of its origin or manipulation, is not associated with all or a portion of the polynucleotide with which it is associated in nature. The term recombinant as used with respect to a protein or polypeptide, means a polypeptide produced by expression of a recombinant polynucleotide. The term recombinant as used with respect to a host cell means a host cell into which a recombinant polynucleotide has been introduced. Recombinant is also used herein to refer to, with reference to material (e.g., a cell, a nucleic acid, a protein, or a vector) that the material has been modified by the introduction of a heterologous material (e.g., a cell, a nucleic acid, a protein, or a vector).

The term "vectors" refers to a nucleic acid molecule capable of transporting another nucleic acid to which it has been linked; a plasmid is a species of the genus encompassed by "vector". The term "vector" typically refers to a nucleic acid sequence containing an origin of replication and other entities necessary for replication and/or maintenance in a host cell. Vectors capable of directing the expression of genes and/or nucleic acid sequence to which they are operatively linked are referred to herein as "expression vectors". In general, expression vectors of utility are often in the form of "plasmids" which refer to circular double stranded DNA loops which, in their vector form are not bound to the chromosome, and typically comprise entities for stable or transient expression or the encoded DNA. Other expression vectors can be used in the methods as disclosed herein for example, but are not limited to, plasmids, episomes, bacterial artificial chromosomes, yeast artificial chromosomes, bacteriophages or viral vectors, and such vectors can integrate into the host's genome or replicate autonomously in the particular cell. A vector can be a DNA or RNA vector. Other forms of expression vectors known by those skilled in the art which serve the equivalent functions can also be used, for example self-replicating extrachromosomal vectors or vectors which integrates into a host genome. Preferred vectors are those capable of autonomous replication and/or expression of nucleic acids to which they are linked. Vectors capable of directing the expression of genes to which they are operatively linked are referred to herein as "expression vectors".

The term "viral vectors" refers to the use of viruses, or virus-associated vectors as carriers of a nucleic acid construct into a cell. Constructs may be integrated and packaged into non-replicating, defective viral genomes like Adenovirus, Adeno-associated virus (AAV), or Herpes simplex virus (HSV) or others, including reteroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, e.g. EPV and EBV vectors.

The articles "a" and "an" are used herein to refer to one or to more than one (i.e., at least one) of the grammatical object of the article. By way of example, "an element" means one element or more than one element. Other than in the operating examples, or where otherwise indicated, all numbers expressing quantities of ingredients or reaction conditions used herein should be understood as modified in all instances by the term "about." The term "about" when used in connection with percentages can mean +1%. The present invention is further explained in detail by the following examples, but the scope of the invention should not be limited thereto.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Other features and advantages of the invention will be apparent from the following Detailed Description, the drawings, and the claims.

Treatment Methods of the Invention

One aspect of the present invention relates to the use of peptides described herein and mutants, variants, analogs or derivatives thereof. Specifically, these methods relate to administering any one of the peptides as described herein or their pharmaceutically acceptable modifications in a pharmaceutically acceptable carrier to a subject, e.g., a mammal in need thereof, e.g., a human, i.e., a subject having inflammation or auto-immune tissue destruction or an individual with hyperglycemia or impaired glycemic control, such as an individual with type 2 diabetes, and in need of protecting and/or stimulating expansion of beta cell mass, or an individual diagnosed with cystic fibrosis, or an individual at high risk of developing endotoxemia as a result of burn or acute radiation exposure. Also, we provide treatment of Rheumatoid arthritis, lupus and graft versus host disease, uveitis, eczema, psoriasis, IBD, and new onset type I diabetes.

Clinical descriptions of these diseases are well known. In some aspects the human is first diagnosed as having one or more symptom of the disease before administering one or more of the peptides of the invention. In some embodiments, the human has not previously been administered AAT as a treatment for the symptoms.

For example, we have shown in established preclinical mouse models for human diseases including type II diabetes (db/db), type I diabetes (NOD), rheumatoid arthritis (CAIA) and lethal endotoxemia that, for example, the SP16 peptide significantly improves the symptoms.

We have also provided evidence that, e.g., the SP16 peptide can be safely administered using well-established preclinical safety studies. For example, we have also shown using FastPatch assay that, for example, the SP16 peptide does not impact hERG activity and we also were not able to identify any hits on human receptor panning study (GenSEP Explorer) for the SP16 peptide.

The db/db mice carry a defective leptin receptor, which impairs their ability to regulate appetite and metabolism. The animals become obese at 3-4 weeks of age, and initially show insulin resistance, which is followed by hyperglycemia at about 4-8 weeks of age. Severe hyperglycemia is paralleled by depletion of the insulin-producing b-cells of the pancreatic islets and death by 10 months of age.

Figure 14:
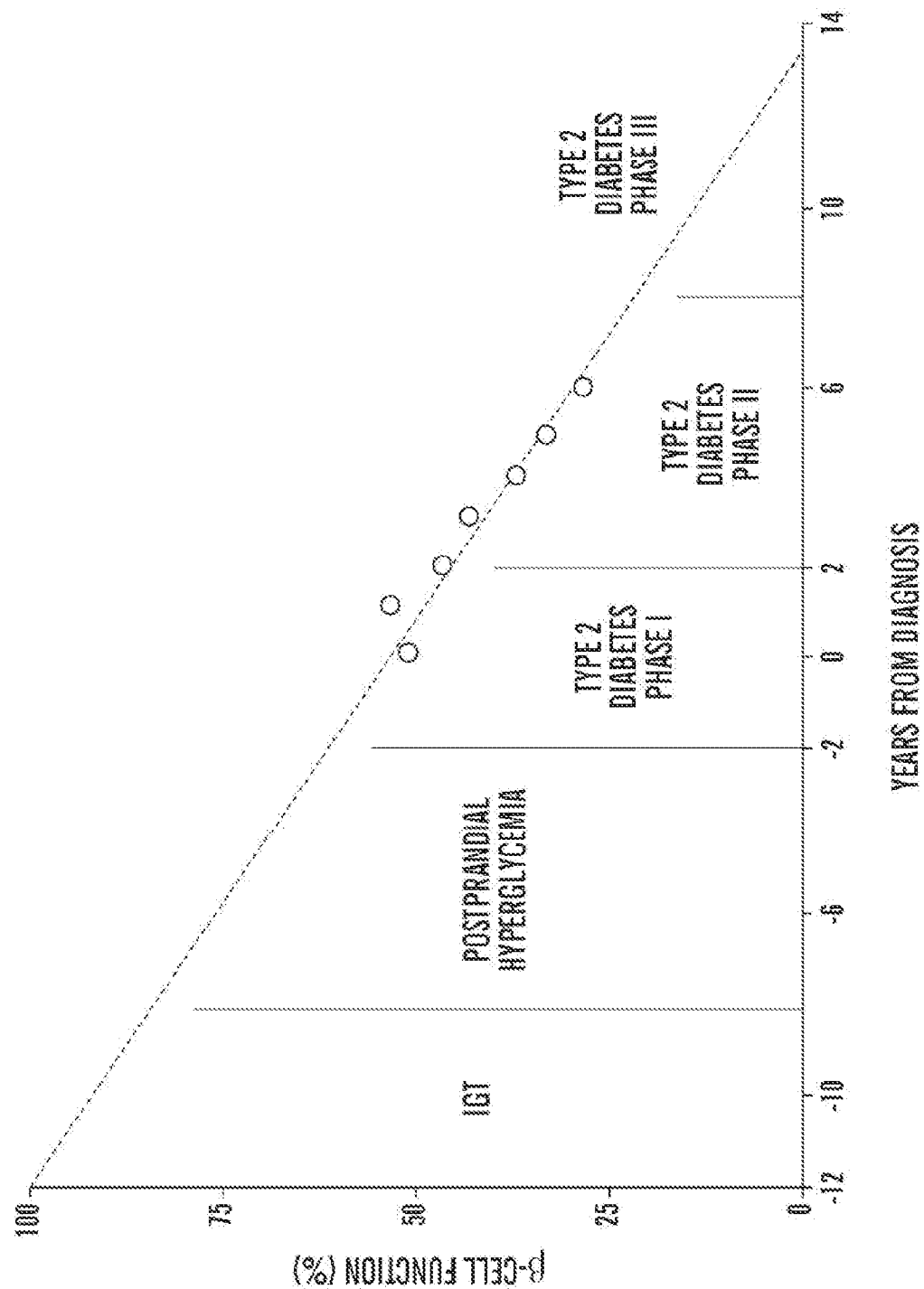
FIG. 14 shows a schematic of the different phases of Type II diabetes.

The db/db animals model the different phases of Type II Diabetes in humans (FIG. 14). We have shown that the peptides of the invention provide benefits at early and late stages of disease. For example, we have shown that SP16 improves glycemic control in the db/db model.

The blood glucose and HbA1c levels showed that SP16 treatment reduces hyperglycemia and improves glycemic control. In this study, five-week old pre-diabetic db/db mice were assigned to groups of 10. The groups received Saline (Vehicle control), 0.6 mg/kg SP16 twice a week or 25 mg/kg Rosiglitazone twice a week. Non-fasted blood glucose levels were determined twice a week using a glucometer. HbA1c levels were determined using the "A1cNow" monitor. Values represent averages for each group. (**) indicates p<0.01 and (*) indicates p<0.05 compared to the Vehicle Control Group (T-test). See, FIG. 8A. It is also known that the target normalization value for human diabetes patients is also true for normal mouse, thus establishing the results from the mouse model directly relevant to human type II diabetes.

Figure 8A:
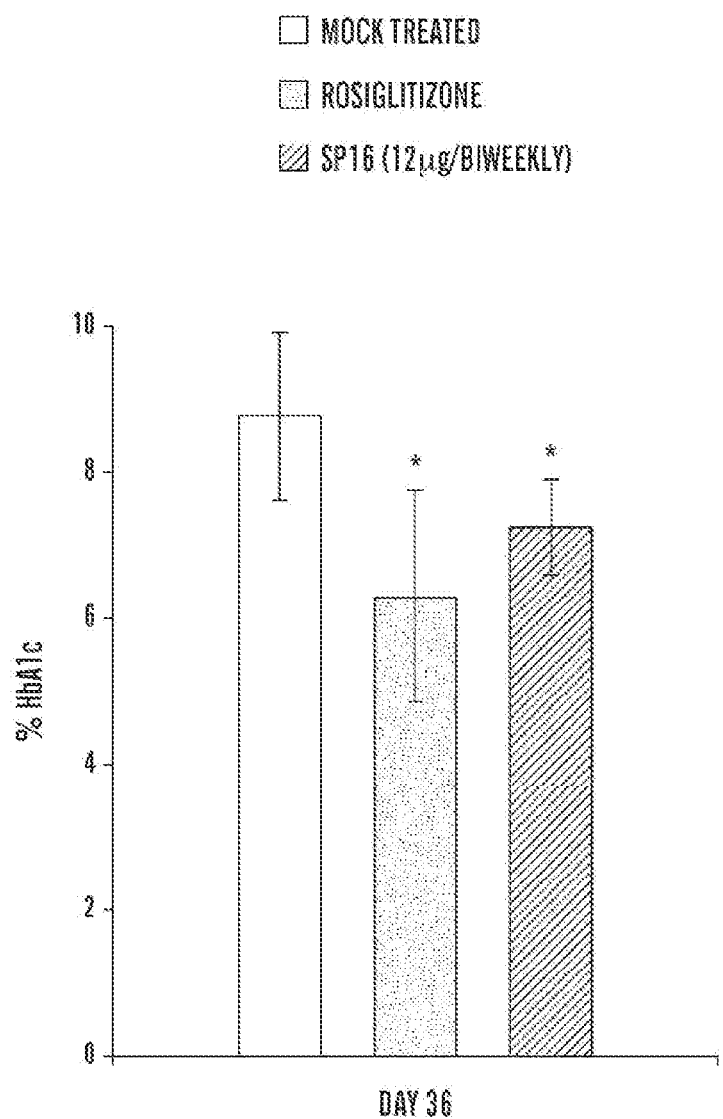
Figure 8B:
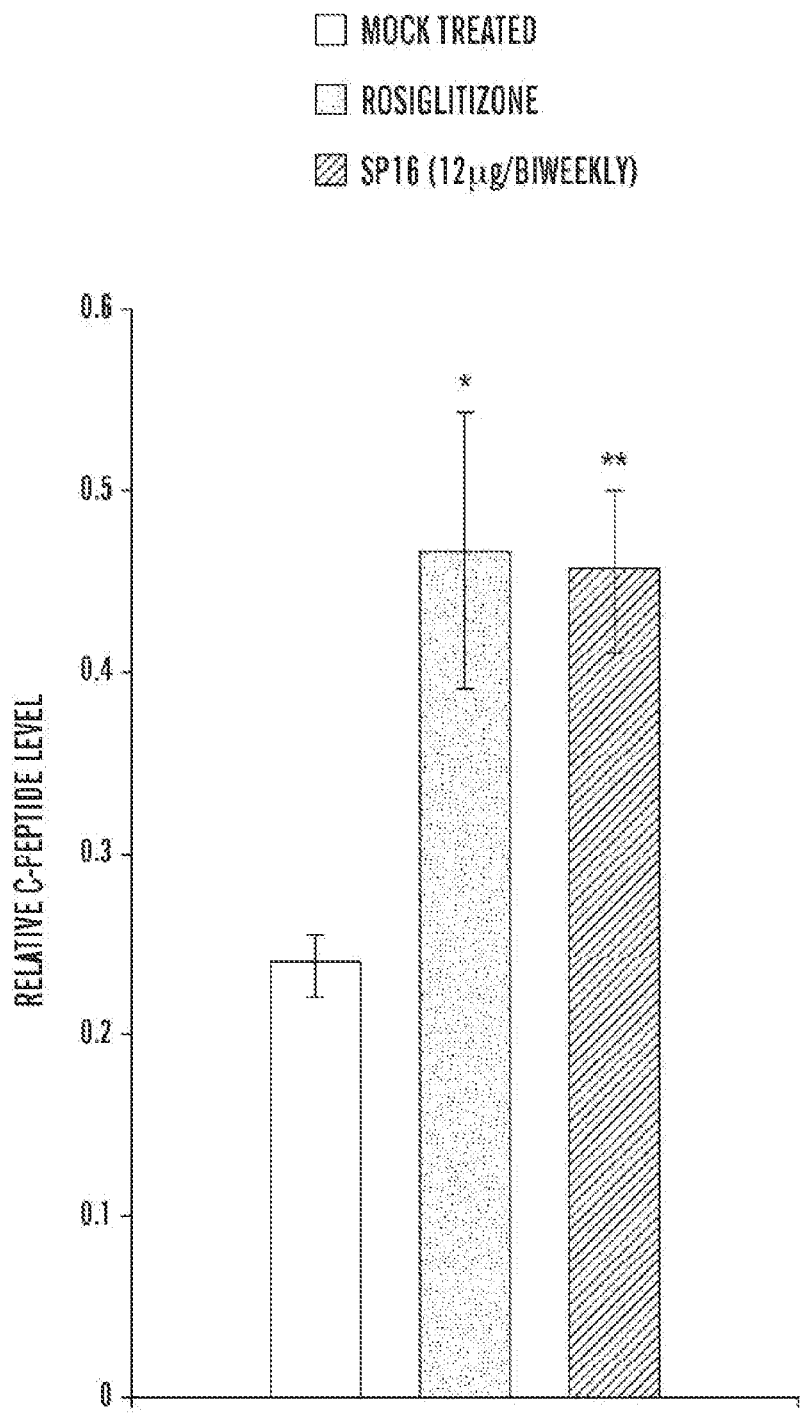
Figure 8D:
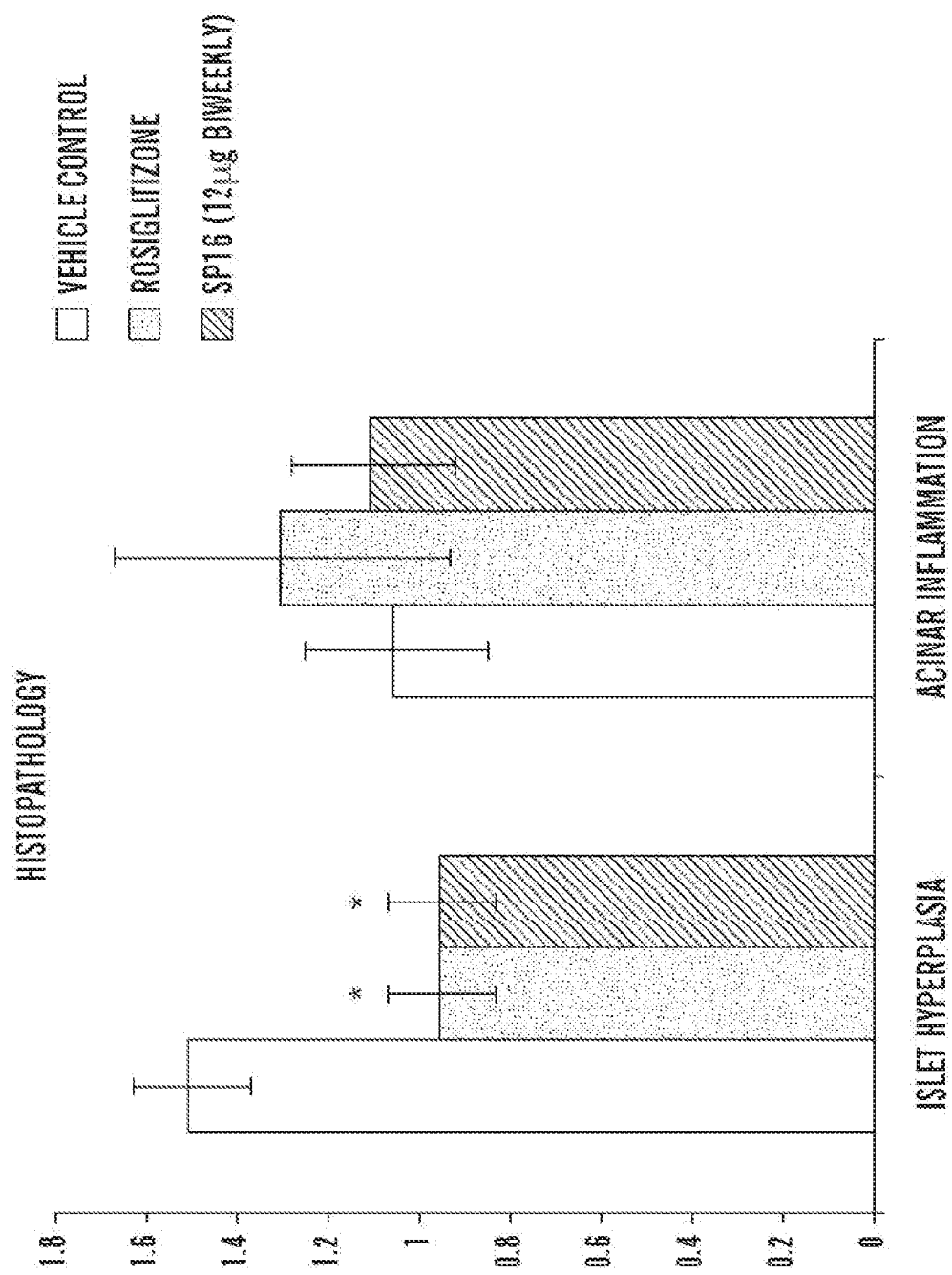

FIGS. 8B and 8D exemplify a graphs summarizing serum C-peptide levels (8B) and islet hyperplasia (8D) in the db/db mouse model of type II diabetes. Increased serum C-peptide levels are consistent with improved β-cell function in the treated groups. Five-week old pre-diabetic db/db mice were assigned to groups of 10. Groups received Saline (Mock), 0.6 mg/kg SP16 or 25 mg/kg Rosiglitazone twice a week. Pooled serum C-peptide levels were determined for each group . . . (*) indicates p<0.05 and (**) p<0.01 compared to the Vehicle control.

Figures 8E, 8F:
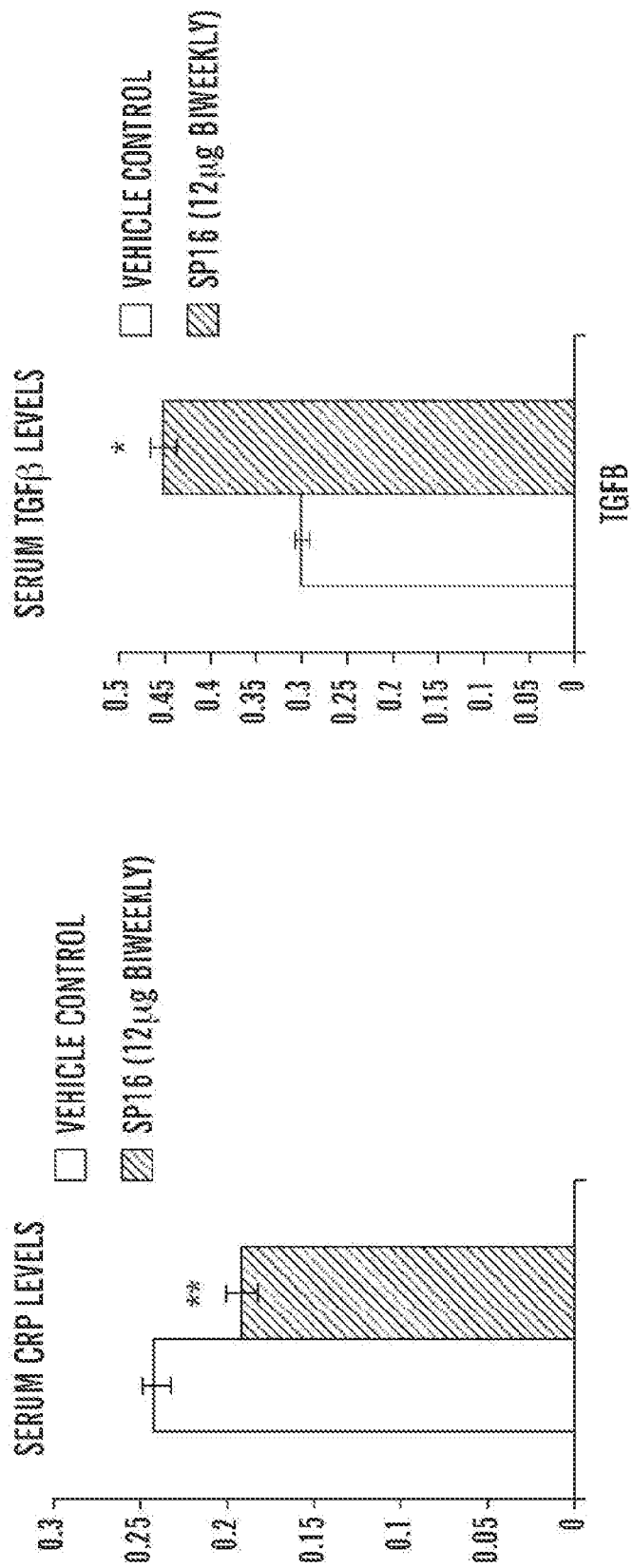

We also showed that the SP16 lowered serum CRP levels when compared to a vehicle control (FIG. 8E). Decreased CRP levels are consistent with reduced inflammation in the SP16 treated group of mice. Similarly, increased TGF-beta levels in SP16 treated mice are consistent with the peptide treatment promoting an anti-inflammatory cytokine profile (FIG. 8F). We assigned eight-week old diabetic db/db mice to 8 groups. Groups received Saline (Mock) or 0.6 mg/kg SP16 biweekly for 12 weeks. Pooled serum CRP and TGF-beta levels were determined for each group. (*) indicates p<0.05 and (**) p<0.01 compared to the Vehicle control group.

The preclinical CAIA model of Rheumatoid Arthritis is a short study where arthritis is induced in Balb/c mice. On Day 0, animals are intravenously injected with a collagen antibody cocktail (MD BioSciences) which initiates autoimmune destruction of the collagen in their joints. On Day 3, an intra-peritoneal injection of LPS is used to exacerbate the autoimmune reaction and inflammation. The readout in this model is paw swelling and histological assessment of joint erosion. Disease typically starts subsiding after 7-10 days.

We demonstrated that SP16 shows efficacy in the preclinical CAIA mouse model. Specifically, we measured cumulative swelling scores for all paws at the peak of disease (Day 7) for groups of 5 animals. Balb/c mice were IV injected with a collagen antibody cocktail (MD BioSciences) on Day 0 and IP injected with LPS on Day 3. Normal Control Animals received no injections and served as disease-free baseline control. Daily SP16 injection of 12 µg/day provided protection equivalent to Dexamethasone and injections of 12 µg once every 3 days reduced the inflammation by almost 50% compared to the treatment with the vehicle control. See e.g., FIG. 9.

Figure 15:
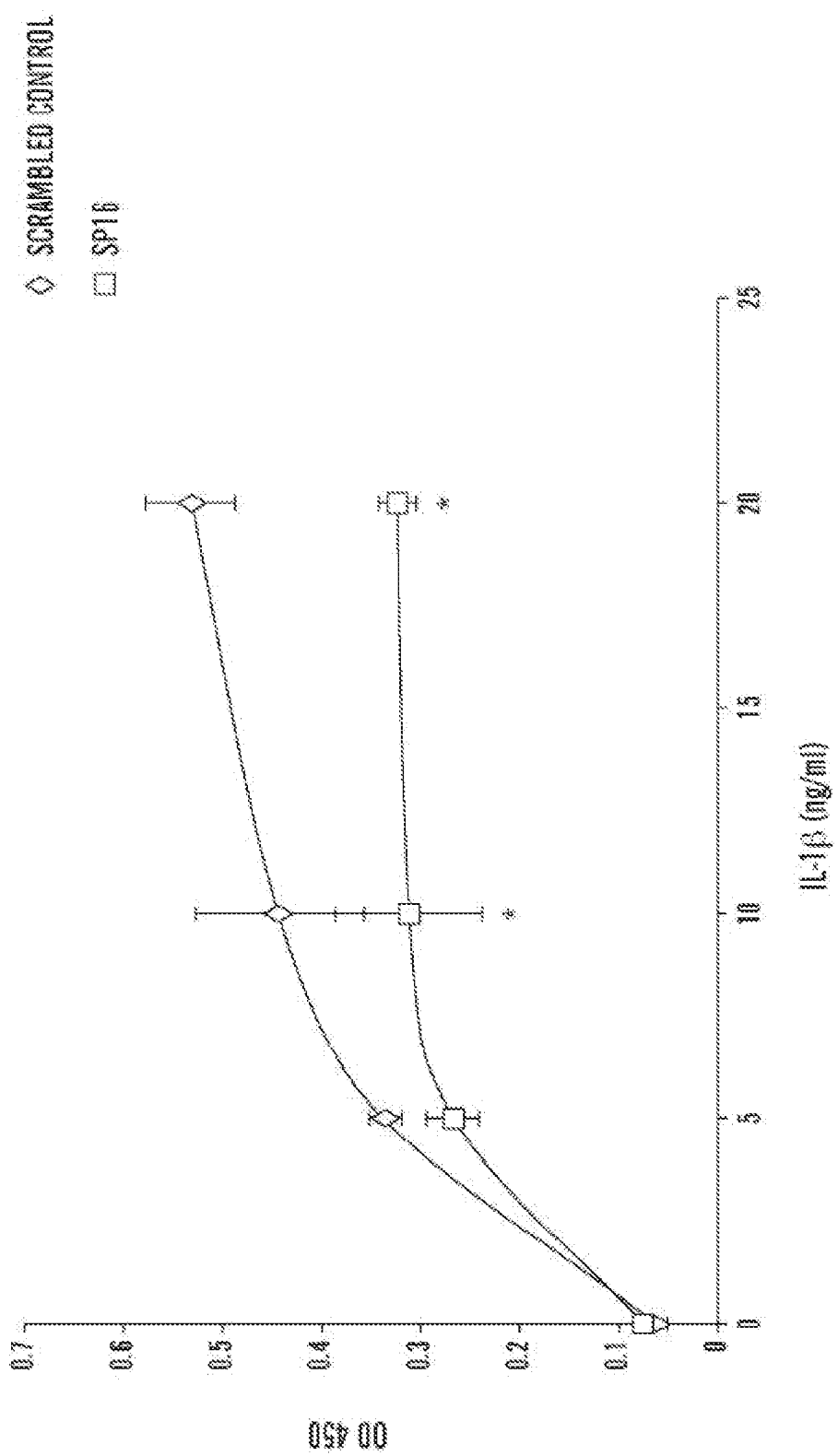
FIG. 15 shows a graph summarizing data from an experiment with primary human synoviocytes. Cells were incubated with 10 uM of the indicated peptides, as well as 0, 5, 10, or 30 ng/ml IL1b, for 48 hours. Upon IL1b stimulation, the cells secrete the metaloprotease MMP1, which is involved in breaking down the cartilage in Arthritis. The assay was done in triplicate and averages with standard deviations are plotted. SP16 lowered MMP1 secretion compared to the scrambled control peptides, at 20 ng/ml IL1b. (*) indicates $p<0.05$ compared to scrambled peptide control.

We also showed that SP16 lowers matrix metalloproteinase-1 (MMP-1) secretion in a cell-based assay mirroring the in results from the vivo CAIA model for rheumatoid arthritis. Cells were incubated with 10 µM of the indicated peptides, as well as 0, 5, 10, or 30 ng/ml IL1β, for 48 hours. Upon IL1β stimulation, the cells secrete the metalloprotease MMP1, which is involved in breaking down the extracellular matrix in arthritis. The assay was done in triplicate and averages with standard deviations are plotted. SP16 lowered MMP1 secretion compared to the scrambled control peptides, at 20 ng/ml IL1β. (*) indicates p<0.05 compared to scrambled peptide control. See, e.g., FIG. 15.

Figure 7:
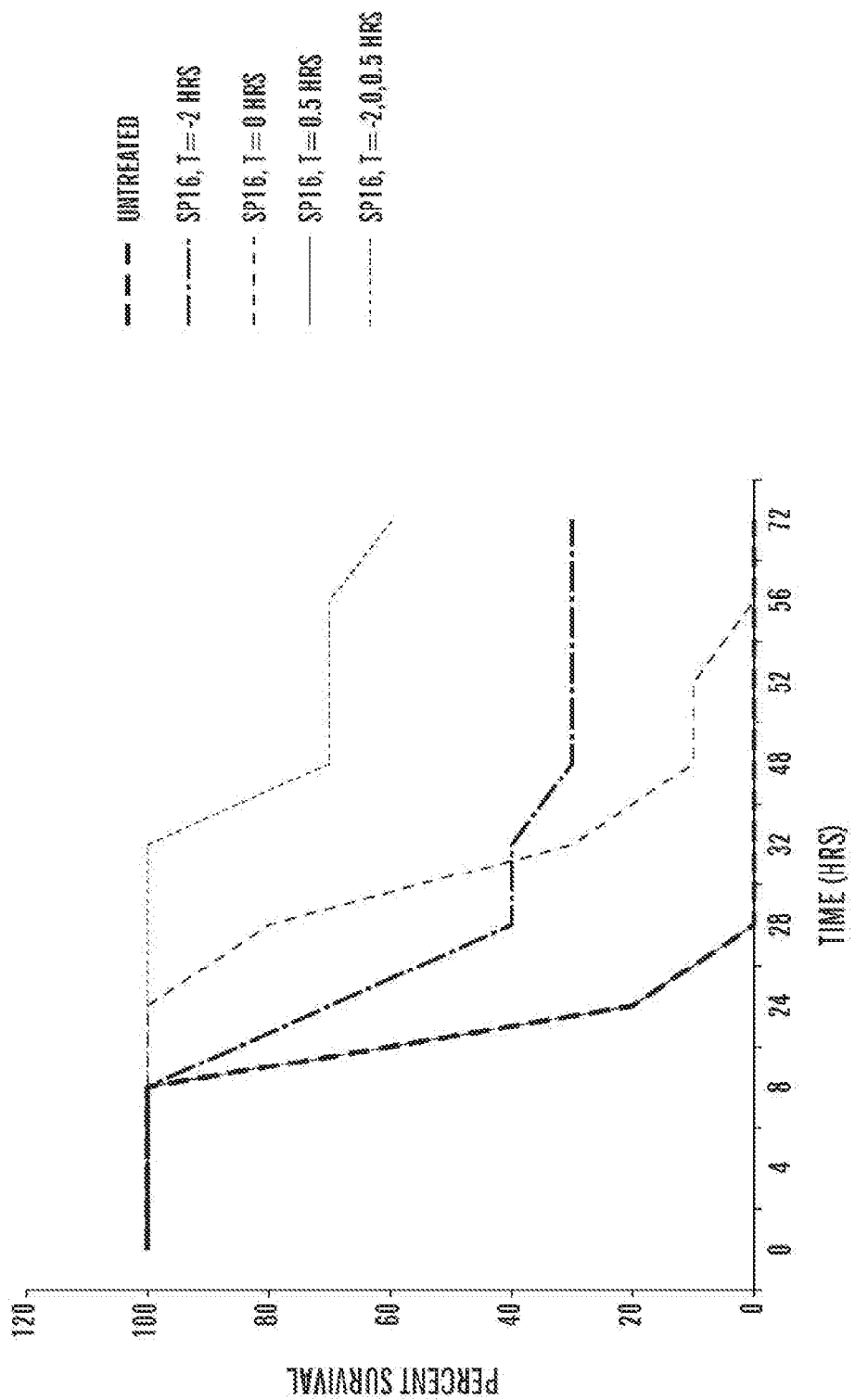
FIG. 7 is a graph summarizing survival during a lethal endotoxemia study in mice. Animals were injected with 0.6 mg/kg SP16 (SEQ ID NO: 1) as indicated: 2 hours before, at the time of, and/or 0.5 hours after induction of Sepsis. Sepsis was induced by injection of 15 mg/kg LPS at T=0. Survival was monitored at the indicated time points. Survival at 72 hours was 60% in the group that received SP16 at T=−2, 0 and 0.5 hours.

We used the lethal endotoxemia model as a predictor for protection against sepsis during acute radiation syndrome. Lipopolysaccharide (LPS) is an endotoxin purified from gram negative bacteria. In animals, LPS elicits a strong immune response as evidenced by increased pro-inflammatory serum cytokine levels and lethality at high doses. In Acute Radiation Syndrome, gram negative bacteria leaking from the GI system contribute to a systemic inflammatory response syndrome and lethality. In the animal model the peptide was administered at time T=−2 hours, T=0 hours or T=0.5 hours. LPS was injected at T=0 hours. We showed that SP16 increases survival in lethal endotoxemia thereby allowing us to extrapolate that the peptide would provide treatment in human burn victims or in human acute radiation syndrome. Groups of 10 animals were injected as indicated, 2 hours before, at the time of, and/or 0.5 hours after induction of lethal endotoxemia. Endotoxemia was induced by injection of 15 mg/kg LPS. Survival was monitored at time points 4, 8, 24, 28, 32, 48, 52, 56 and 72 hours (FIG. 7).

Figure 18:
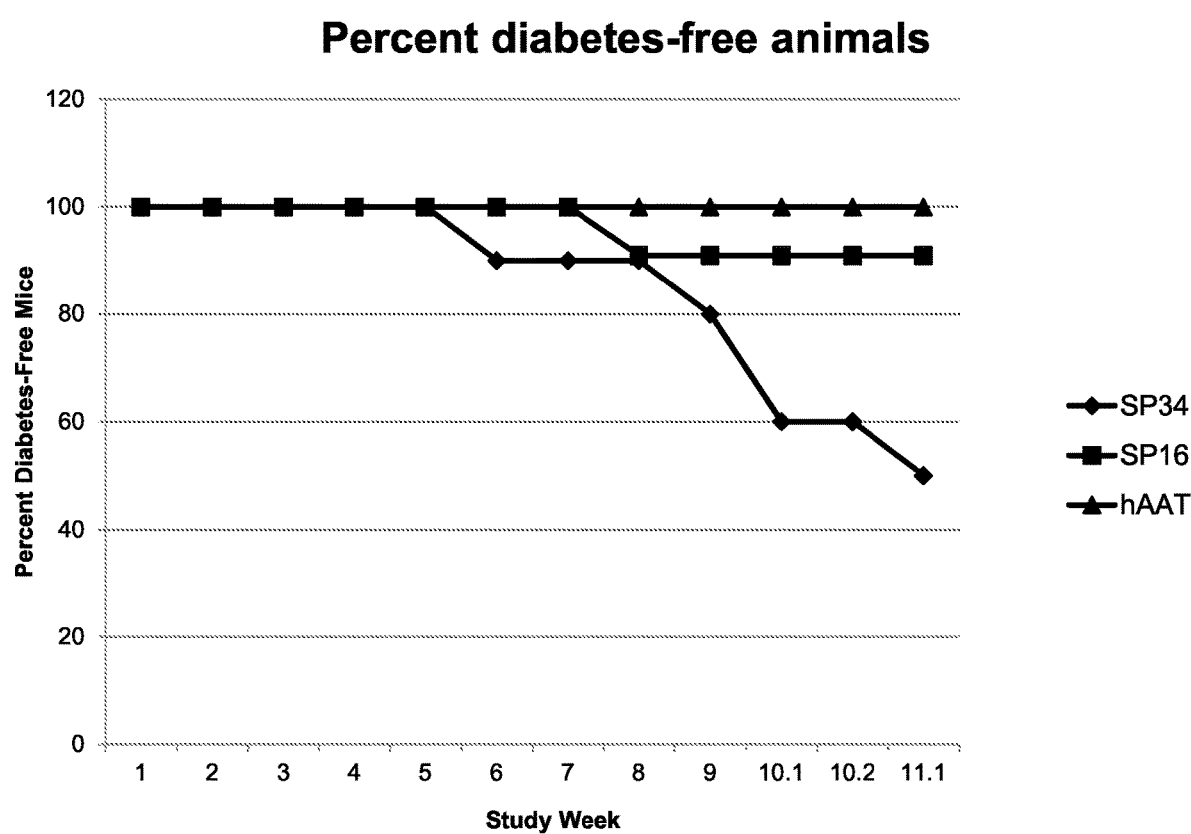
FIG. 18 shows data from a study in NOD mice, a spontaneous autoimmune diabetes model. Groups of 12 animals were injected with SP16, hAAT or scrambled control peptide. Non-fasted blood glucose levels were measured twice a week and animals with two consecutive readings greater than 300 mg/dl were considered diabetic. Both SP16 and hAAT delayed and reduced the incidence of diabetes.

The NOD model of type I diabetes was used to determine the efficacy of SP16 in preventing and/or delaying the onset of symptoms and overt disease. As depicted in FIG. 18, administration of the peptide was demonstrated to prevent and delay the development of type I diabetes in this model.

Therefore, in one aspect we provide methods for treatment of type II diabetes, type I diabetes, rheumatoid arthritis and endotoxemia caused by burns and/or radiation comprising administering to a human subject in need thereof a composition comprising at least one of the peptides of the invention. In some aspects, the peptide comprises SP16.

We have shown that the peptides of the invention, e.g., SP16 are toll like receptor-2 agonists. Accordingly, without wishing to be bound by a theory, the peptides, such as SP16, act as an anti-inflammatory drug by promoting an anti-inflammatory cytokine profile. Also, without wishing to be bound by a theory, the peptides, such as SP16, also can act as immune modulators by inducing expansion of tolerogenic and protective T-regulatory cells (T-regs). Further, without wishing to be bound by a theory, the peptides, such as SP16, also can down-regulate autoimmune responses without inducing general immunological suppression thereby providing a superior treatment for autoimmune diseases compared to most of the currently available treatments which generally suppress the immune system exposing the treated individuals to a risk of infections while treated with the general immunosuppressants.

As the peptides are derived from AAT, and in view of our results in vivo and in vitro models, it is reasonable to expect most of the AAT's therapeutic effects to apply also to the peptides of the invention, such as SP16. Specifically, AAT has been shown to modulate T-cell proliferation and NF-kappa-B activation; impair NK target cell interaction; inhibit serine proteases activation of epithelial cell EGFR/TLR-4 signaling; be involved in TNF-alpha-induced gene expression and apoptosis or endothelial cells; prevent red blood cell haemolysis by E. coli, decrease circulating eosinophil cell count; inhibit neutrophil chemotaxis, NADHP oxidase and ANCA signaling; inhibit monocyte and macrophage cytokine release and regulation of CD14 expression, and inhibit mast cell histamine release; and modulate B-cell proliferation and cytokine production.

Therefore, in some embodiments, we provide methods for modulating T-cell proliferation and NF-kappa-B activation; impairing NK target cell interaction; inhibiting serine proteases activation of epithelial cell EGFR/TLR-4 signaling; modulating TNF-alpha-induced gene expression and apoptosis or endothelial cells; preventing red blood cell haemolysis by E. coli, decreasing circulating eosinophil cell count; inhibiting neutrophil chemotaxis, NADHP oxidase and ANCA signaling; inhibiting monocyte and macrophage cytokine release and regulation of CD14 expression, and inhibiting mast cell histamine release; and modulating B-cell proliferation and cytokine production comprising the step of administering to a human subject a composition comprising at least one of the peptides of the invention. In some aspects, the peptide is SP16, which may comprise one or more modifications typically performed to enhance peptide bioavailability and/or shelf life, such as pegylation and the like.

We also performed a peptide optimization assay using an alanine scan with the TLR-2 assay. Data was obtained using an experiment with an engineered TLR-2 indicator cell line (HEK-BLUE™ mTLR2, Invivogen). Cells were incubated with the 20 µg/ml of the indicated peptides for 24 hours. Upon TLR2 activation, the cells secrete alkaline phosphatase, which can be assayed. The assay was done in triplicate and averages are plotted. Peptide SP34 is a scrambled peptide control (Yellow), and PAM (Pam3CSK4; Red) is a positive control. See, e.g., FIG. 12.

The following table provides the results from an assay for SP16's pharmacokinetic profile.

| PK parameters | SP16, IV (5 mg/kg) |
| --- | --- |
| C0 (µg/m L) | 2.5 |
| AUC to Last (µg-hr/mL) | 0.9 |
| t½ (hr) | 1.9 |
| Total CL (mL/hr) | 140 |
| Total CL (mL/min/kg) | 9.7 |
| Last Time point | 8.0 |
| MRTINF (hr) | 1.1 |
| V (mL) | 374 |
| Vss (mL) | 149 |

In performing the assay, three normal rats were injected intravenously with 5 mg/kg SP16 and the plasma concentration of SP16 established at 8 time points following the injection. For each timepoint, SP16 levels were determined by LC/MS/MS and the values used to calculate the Cmax (2.5 ug/ml) and T1/2 (1.9 hours). The assay was executed by Apredica, Boston, Mass. Accordingly, we determined that SP16 has a half-life of 1.9 hours in normal rats.

The SP16 safety profile also included hERG data. The hERG FastPatch assay showed that SP16 does not inhibit hERG at up to 25 µM doses. This data predicts that SP16 will not have cardiac safety issues in humans. The study was executed by Apredica, Boston, Mass.

| Client ID | Test conc (µM) | IC50 value (µM) | comment |
|---|---|---|---|
| SP16 | 0.008-25 | >25 | No concentration-dependent inhibition observed. |
| Quinidine | 0.01-10 | 1.8 | positive control |

| Customer Id | Mean % Activity | | | | | | Comments |
|---|---|---|---|---|---|---|---|
| | 0 µM | 0.008 µM | 0.04 µM | 0.2 µM | 1 µM | 5 µM | 25 µM | |
| SP16 | 100 | 89 | 95 | 95 | 78 | 88 | 89 | No concentration-dependent inhibition observed |

In addition, we also performed a profile using human receptor palming. The GenSEP Explorer panel contains 111 in vitro assay targets carefully selected to assess drug/chemical biological activities. Assay categories include GPCRs, Voltage-Gated Ion Channels, Ligand-Gated Ion Channels, Neurotransmitter transporters, Nuclear Receptors and Steroids as well as a diverse set of biochemical targets including phosphodiesterases, kinases and other relevant enzymes. The study was executed by Caliper LifeSciences, and the results are summarized in the table below. It appears that SP16 has no effect on 111 human receptors, indicating that SP16 has an excellent human safety profile.

| Receptor Class | Number of Receptors Tested | Percent inhibition |
|---|---|---|
| Neurotransmitter Related | 47 | Insignificant |
| Steroids | 4 | Insignificant |
| Ion Channels | 8 | Insignificant |
| Growth factors & hormones | 2 | Insignificant |
| Second Messengers | 3 | Insignificant |
| Brain/gut peptides | 15 | Insignificant |
| Enzymes | 20 | Insignificant |
| Enzymes, Kinases | 11 | Insignificant |
| Cell-Based, Functional | 1 | Insignificant |

In view of the safety profile of SP16, we can reasonably extrapolate that the other peptide fragments provided herein would also be safe for administering to human.

In one embodiment, the methods of treatment described herein, further comprise selection or diagnosis of a subject having any of the above-described conditions, e.g., one arising from inflammation prior to administering a peptide as disclosed herein or a mutant, variant, analog or derivative thereof, to thereby treat the condition or dysfunction, such as inflammation. Such selection is performed by the skilled practitioner by a number of available methods, for instance, assessment of symptoms which are described herein. For example, one can assess the amount of TNF-alpha in the subject to determine the amount of inflammation present in the subject. In the case of diabetes, one can measure glycemic control using well-defined blood glucose levels. In some aspects of all the embodiments of the invention, the peptides can be administered to individuals with pre-diabetic stage to prevent development of type 2 diabetes. There are a number of tests which can be used to determine if, e.g., a human subject is affected with pre-diabetes. Such tests include, e.g., the A1C test, fasting plasma glucose test (FPG), and the oral glucose tolerance test (OGTT). Pre-diabetic individuals typically score at or above 5.7% to under 6.5% on the A1C test, whereas diabetics score over 6.5% on this test. Pre-diabetic individuals also typically score at or over 100 mg/dl to under 126 mg/dl using the FPG test whereas diabetics score over 126 mg/dl. Pre-diabetic individuals typically score at or over 140 to under 200 mg/dl using the OGTT test whereas diabetic individuals score over 200 mg/dl. Thus, a method of preventing diabetes according to the present invention may comprise administering the peptide to an individual who has first been diagnosed as pre-diabetic, e.g., using any of the above-described methods. In some aspects, the method comprises identifying diabetes type 2 in the subject and then administering the synthetic peptide of the invention to the subject.

In some aspects of all the embodiments, one may use C-reactive protein as a marker for inflammation or treatment efficacy. C-reactive protein (CRP) is used to detect inflammation if there is a high suspicion of tissue injury or infection somewhere in the body. CRP serves as a general marker for infection and inflammation and can be used to evaluate an individual for an acute or chronic inflammatory condition. A high or increasing amount of CRP in the blood suggests the presence of inflammation. In individuals suspected of having a serious bacterial infection, a high CRP suggests the presence of one. In people with chronic inflammatory conditions, high levels of CRP suggest a flare-up or that treatment has not been effective. Normal concentration in healthy human serum is usually lower than 10 mg/L, slightly increasing with aging. Higher levels are found in late pregnant women, mild inflammation and viral infections (10-40 mg/L), active inflammation, bacterial infection (40-200 mg/L), severe bacterial infections and burns (>200 mg/L). In some aspects the term "reference value" refers to the measurements of CRP when CRP is used as a diagnostic test for inflammation.

In some aspects, the subject may carry a diagnosed gene mutation, such as when the subject is diagnosed as having cystic fibrosis (CF). CF is an autosomal, recessive disease caused by mutations in the gene for the protein cystic fibrosis transmembrane conductance regulator (CFTR). In some aspects, the invention provides a method of first identifying a CF causing mutation in the subject and then administering the synthetic peptide of the invention into the subject. Currently 1913 mutations have been reported to the publicly available CF database maintained by Cystic Fibrosis Centre at the Hospital for Sick Children in Toronto, Canada. Often, testing is used to analyze the most common mutations such as ΔF508. The parental history and ethnic origin may provide clues to the kinds of mutations one can screen for in an affected child. Diagnosis of CF can also include detection of salty tasting skin, poor growth and poor weight gain despite a normal food intake, accumulation of thick, sticky mucus, frequent chest infections, and coughing or shortness of breath. Males can be infertile due to congenital absence of the vas deferens. Symptoms often appear in infancy and childhood, such as bowel obstruction due to meconium ileus in newborn babies. As the children grow, they must exercise to release mucus in the alveoli. Ciliated epithelial cells in the patient have a mutated protein that leads to abnormally viscous mucus production In some aspects, the subject is diagnosed with burns and thus at high risk of developing burn-related endotoxemia, and subsequently, the peptides of the invention may be administered to the subject to prevent development of endotoxemia. In some aspects, the burn victim does not have and has not been treated for inflammatory conditions, diabetes, COPD or CF. In some aspects, the subject has been exposed to radiation and has acute radiation injury, and subsequently, the peptides of the present invention may be administered to the subject to prevent development of endotoxemia. In some aspects, the subject has signs or symptoms of endotoxemia and the peptides of the invention may be administered to such a subject as well. After ionizing radiation exposure, if the dose is sufficiently high, gram negative bacteria leak from the gastro-intestinal system and can cause endotoxemia (Sepsis). We have shown that the peptides improve survival during induced lethal endotoxemia in a mouse model. Thus, based on these results we can conclude that the peptides can also be used in humans being at risk of a similar condition, namely endotoxemia or sepsis as a result of burns or acute exposure to radiation.

Successful or effective treatment is evidenced by amelioration of one or more symptoms of the condition or dysfunction as discussed herein. Administering a peptide as disclosed herein or a mutant, variant, analog or derivative thereof in a subject in need thereof is expected to prevent or retard the development of the conditions and physical dysfunctions described herein (e.g., those arising from inflammation or auto-immune tissue destruction or to a condition ameliorated by stimulation of expansion of beta cell mass in an individual with diabetes). The term "prevention" is used to refer to a situation wherein a subject does not yet have the specific condition being prevented, meaning that it has not manifested in any appreciable form. Prevention encompasses prevention or slowing of onset and/or severity of a symptom, (including where the subject already has one or more symptoms of another condition). Prevention is performed generally in a subject who is at risk for development of a condition or physical dysfunction. Such subjects are said to be in need of prevention. For example, reduction in the TNF-alpha levels compared to the levels prior to administering the peptides of the invention, would be evidence of successful treatment. Improvement in glycemic control is another way of showing that the treatment has had an effect. Also, if the A1C test, fasting plasma glucose test (FPG), and the oral glucose tolerance test (OGTT) show that the pre-diabetic test results stay at pre-diabetic test levels, one can conclude that prevention of diabetes in the pre-diabetic subject has been successful. Also, if a burn victim or a subject exposed to acute radiation injury does not develop endotoxemia or the signs and symptoms of endotoxemia are mild the administration of the peptide can be considered as having an effect in prevention.

In one embodiment, the methods of prevention described herein, further comprise selection of such a subject at risk for a condition, e.g., those arising from inflammation or auto-immune tissue destruction or a condition ameliorated by stimulation of expansion of beta cell mass in an individual with diabetes, or subject that has severe burns or has suffered acute radiation injury and is thus susceptible for endotoxemia, or a subject that is a smoker and thus susceptible for COPD, or physical dysfunction as described herein, prior to administering a peptide or a mutant, variant, analog or derivative thereof, in the subject, to thereby prevent the condition or dysfunction. Such selection is performed by the skilled practitioner by a number of available methods. For instance, assessment of risk factors or diagnosis of a disease which is known to cause the condition or dysfunction, or treatment or therapy known to cause the condition or dysfunction. Subjects which have a disease or injury or a relevant family history which is known to contribute to the condition are generally considered to be at increased risk.

As used herein, the terms "treat" or "treatment" or "treating" refers to therapeutic treatment measures, wherein the object is to prevent or slow the development of the disease, such as reducing at least one effect or symptom of a condition, disease or disorder associated with inflammation. Treatment is generally "effective" if one or more symptoms are improved or clinical markers, such as TNF-alpha, CRP, blood glucose and/or HbA1c, levels are within normal values or closer to the normal reference values than abnormal values reflecting inflammation or poor glycemic control, depending on the condition, as that term is defined herein. Alternatively, treatment is "effective" if the progression of a disease is slowed down, exhibition of a symptom or a marker for a disease is reduced. That is, "treatment" includes the improvement of symptoms or markers, slowing of progress or slowing of worsening of at least one symptom that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state. "Treatment" can also mean prolonging survival as compared to expected survival if not receiving treatment. Those in need of treatment include patients with one or more symptom of inflammation, such as symptoms associated with rheumatoid arthritis, COPD or diabetes, including Type 1 and Type 2 diabetes. In some aspects of all the embodiments of the invention, the subject in need of treatment has cystic fibrosis or has been subject to burns or acute radiation and is thus at high risk of developing endotoxemia.

TNF-alpha levels can be assessed, for example, using any number of readily available commercial ELISA kits. A1C test, FPG, and OGTT are commonly used to assess glycemic control in diagnosing and managing diabetes and pre-diabetes.

In some aspects, the invention relates to methods of preventing inflammation by administering the peptides as described to an individual not yet presenting symptoms of inflammation. For example, the peptides can be administered to an individual at high risk of developing diabetes or diagnosed with pre-diabetes, a condition defined by increase blood sugar levels but levels that are not yet considered diabetic, but not yet having diabetes to assist in slowing down the development or preventing the development of diabetes from the pre-diabetic stage.

Before people develop type 2 diabetes, they almost always have "prediabetes"—blood glucose levels that are higher than normal but not yet high enough to be diagnosed as diabetes. Recent research has shown that some long-term damage to the body, especially the heart and circulatory system, may already be occurring during prediabetes. There are a number of tests which can be used to determine if, e.g., a human subject is affected with prediabetes. Such tests include, e.g., the A1C test, fasting plasma glucose test (FPG), and the oral glucose tolerance test (OGTT). Prediabetic individuals typically score at or above 5.7% to under 6.5% on the A1C test, whereas diabetics score over 6.5% on this test. Prediabetic individuals also typically score at or over 100 mg/dl to under 126 mg/dl using the FPG test whereas diabetics score over 126 mg/dl. Prediabetic individuals typically score at or over 140 to under 200 mg/dl using the OGTT test whereas diabetic individuals score over 200 mg/dl. Thus, a method of preventing diabetes according to the present invention may comprise administering the peptide to an individual who has been diagnosed as pre-diabetic, e.g., using any of the above-described methods.

The term "effective amount" as used herein refers to the amount of a pharmaceutical composition comprising one or more peptides as disclosed herein or a mutant, variant, analog or derivative thereof, to decrease at least one or more symptom of the disease or disorder, and relates to a sufficient amount of pharmacological composition to provide the desired effect. The phrase "therapeutically effective amount" as used herein means a sufficient amount of the composition to treat a disorder, at a reasonable benefit/risk ratio applicable to any medical treatment. The term "therapeutically effective amount" therefore refers to an amount of the composition as disclosed herein that is sufficient to effect a therapeutically or prophylactically reduction in a symptom or clinical marker associated with increased levels of inflammation or hyperglycemia when administered to a typical subject who has anemia, anemia of inflammation or type I diabetes. Typically reduction of more than 20% of a disease marker, such as an inflammatory marker, e.g., TNF-alpha, is indicative of effective treatment. In some instances, reduction of more than 50% or more than 75% from the amount of TNF-alpha levels in the individual prior to administering the peptides of the invention is indicative of effective treatment.

A therapeutically or prophylactically significant reduction in a symptom is, e.g. at least about 10%, at least about 20%, at least about 30%, at least about 40%, at least about 50%, at least about 60%, at least about 70%, at least about 80%, at least about 90%, at least about 100%, at least about 125%, at least about 150% or more in a measured parameter as compared to a control or non-treated subject or the state of the subject prior to administering the peptide. Measured or measurable parameters include clinically detectable markers of disease, for example, elevated or depressed levels of a biological marker, such as TNF-alpha, as well as parameters related to a clinically accepted scale of symptoms or markers for inflammation. It will be understood, however, that the total daily usage of the compositions and formulations as disclosed herein will be decided by the attending physician within the scope of sound medical judgment. The exact amount required will vary depending on factors such as the type of disease being treated, gender, age, and weight of the subject.

With reference to the treatment of a subject with inflammation, auto-immune tissue destruction or type I diabetes, the term "therapeutically effective amount" refers to the amount that is safe and sufficient to delay the development of one or more symptom and results in decrease in the amount of an inflammatory marker, e.g., TNF-α or CRP concentrations, or improvement in blood glucose levels in patients compared to the amount of the inflammatory marker or blood glucose levels prior to administering the peptide. The amount can thus improve or cause a decrease in at least one symptom of inflammation, auto-immune tissue destruction or type I diabetes or slow the course of disease progression, such as stabilizing blood glucose levels. The effective amount for the treatment of a disease depends on the type of disease, the species being treated, the age and general condition of the subject, the mode of administration and so forth. Thus, it is not possible to specify the exact "effective amount." However, for any given case, an appropriate "effective amount" can be determined by one of ordinary skill in the art using only routine experimentation. The efficacy of treatment can be judged by an ordinarily skilled practitioner, for example, efficacy can be assessed in known animal models of inflammation (e.g. LPS model), auto-immune tissue destruction (e.g. CAIA model) or diabetes (e.g. db/db mouse model). When using an experimental animal model, efficacy of treatment is evidenced when a reduction in a symptom of inflammation, auto-immune tissue destruction or hyperglycemia is shown versus untreated animals.

As used herein, the terms "administering," and "introducing" are used interchangeably herein and refer to the placement of the therapeutic agents such as one or more peptides as disclosed herein or a mutant, variant, analog or derivative thereof into a subject by a method or route which results in delivering of such agent(s) at a desired site. The compounds can be administered by any appropriate route which results in an effective treatment in the subject.

Figure 16:
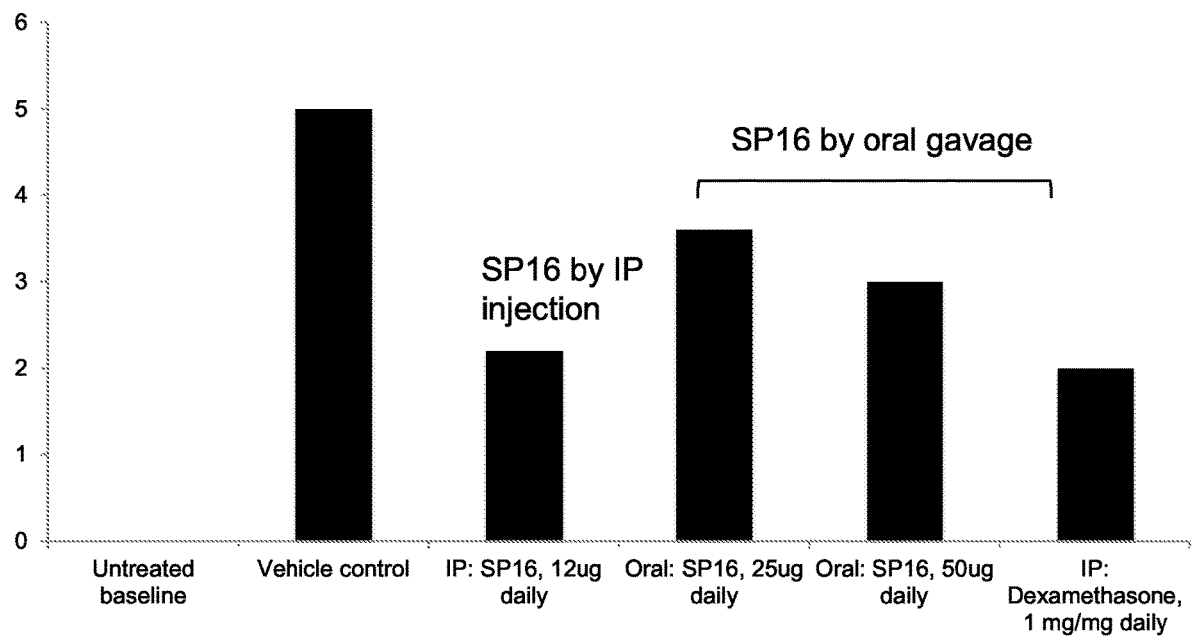
FIG. 16 shows a graph summarizing data from a study in the mouse CAIA Rheumatoid Arthritis model. The graph shows the average cumulative swelling (clinical) scores for all paws at the peak of disease (Day 7) for groups of 5 animals. Balb/c mice were IV injected with a collagen antibody cocktail (MD BioSciences) on Day 0 and IP injected with LPS on Day 3. Normal Control Animals received no injections and served as disease-free baseline control. SP16 was provided daily by intraperitoneal injection (Dose: 12 ug/animal) or by oral gavage (Dose: 25 and 50 ug/animal). Daily SP16 injection provided protection equivalent to daily administration of 1 mg/kg Dexamethasone.

The one or more peptides as disclosed herein or a mutant, variant, analog or derivative thereof may be administered by any route known in the art or described herein, for example, oral, parenteral (e.g., intravenously or intramuscularly), intraperitoneal, rectal, cutaneous, nasal, vaginal, inhalant, skin (patch), or ocular. The one or more peptides as disclosed herein or a mutant, variant, analog or derivative thereof may be administered in any dose or dosing regimen. One can also use pumps, like the ones used for insulin administration. In some embodiments, the one or more peptides can be administered orally. As depicted in FIG. 16, oral administration of SP16 was demonstrated to be efficacious, e.g. compared to intraperitoneal injection of SP16 and dexamethasone.

Dosage

With respect to the therapeutic methods of the invention, it is not intended that the administration of the one or more peptides as disclosed herein or a mutant, variant, analog or derivative thereof and be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat the inflammation-related disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the one or more peptides as disclosed herein or a mutant, variant, analog or derivative thereof may be provided at a dose of 0.0001, 0.01, 0.01 0.1, 1, 5, 10, 25, 50, 100, 500, or 1,000 mg/kg or µg/kg. Effective doses may be extrapolated from dose-response curves derived from in vitro or animal model test bioassays or systems.

Dosages for a particular patient or subject can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the one or more peptides as disclosed herein or a mutant, variant, analog or derivative thereof and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more peptides as disclosed herein or a mutant, variant, analog or derivative thereof are optionally tested in one or more appropriate in vitro and/or in vivo animal models of disease, such as models of inflammation or diabetes, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of one or more peptides as disclosed herein or a mutant, variant, analog or derivative thereof. Administration can be accomplished via single or divided doses.

In determining the effective amount of one or more peptides as disclosed herein or a mutant, variant, analog or derivative thereof to be administered in the treatment or prophylaxis of disease the physician evaluates circulating plasma levels, formulation toxicities, and progression of the disease.

The efficacy and toxicity of the compound can be determined by standard pharmaceutical procedures in cell cultures or experimental animals, e.g., ED50 (the dose is effective in 50% of the population) and LD50 (the dose is lethal to 50% of the population). The dose ratio of toxic to therapeutic effects is the therapeutic index, and it can be expressed as the ratio, LD50/ED50. Pharmaceutical compositions which exhibit large therapeutic indices are preferred.

These compounds may be administered to humans and other animals for therapy by any suitable route of administration that works for small peptides, including orally, nasally, as by, for example, a spray, rectally, intravaginally, parenterally, intracisternally and topically, as by powders, ointments or drops, including buccally and sublingually.

Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the subject.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

Formulation of Pharmaceutical Compositions—"Pharmaceutically Acceptable Carriers"

The administration of one or more peptides as disclosed herein or a mutant, variant, analog or derivative thereof may be by any suitable means that results in a concentration of the protein that treats the disorder. The compound may be contained in any appropriate amount in any suitable carrier substance, and is generally present in an amount of 1-95% by weight of the total weight of the composition. The composition may be provided in a dosage form that is suitable for the oral, parenteral (e.g., intravenously or intramuscularly), intraperitoneal, rectal, cutaneous, nasal, vaginal, inhalant, skin (patch), or ocular administration route. Thus, the composition may be in the form of, e.g., tablets, capsules, pills, powders, granulates, suspensions, emulsions, solutions, gels including hydrogels, pastes, ointments, creams, plasters, drenches, osmotic delivery devices, suppositories, enemas, injectables, implants, sprays, or aerosols. The pharmaceutical compositions may be formulated according to conventional pharmaceutical practice (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York, incorporated, herein, by reference in its entirety).

Pharmaceutical compositions according to the invention may be formulated to release the active compound immediately upon administration or at any predetermined time or time period after administration. The latter types of compositions are generally known as controlled release formulations, which include (i) formulations that create substantially constant concentrations of the agent(s) of the invention within the body over an extended period of time; (ii) formulations that after a predetermined lag time create substantially constant concentrations of the agent(s) of the invention within the body over an extended period of time; (iii) formulations that sustain the agent(s) action during a predetermined time period by maintaining a relatively constant, effective level of the agent(s) in the body with concomitant minimization of undesirable side effects associated with fluctuations in the plasma level of the agent(s) (sawtooth kinetic pattern); (iv) formulations that localize action of agent(s), e.g., spatial placement of a controlled release composition adjacent to or in the diseased tissue or organ; (v) formulations that achieve convenience of dosing, e.g., administering the composition once per week or once every two weeks; and (vi) formulations that target the action of the agent(s) by using carriers or chemical derivatives to deliver the therapeutic to a particular target cell type. Administration of the protein in the form of a controlled release formulation is especially preferred for compounds having a narrow absorption window in the gastrointestinal tract or a relatively short biological half-life.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the protein is formulated with appropriate excipients into a pharmaceutical composition that, upon administration, releases the protein in a controlled manner. Examples include single or multiple unit tablet or capsule compositions, oil solutions, suspensions, emulsions, microcapsules, molecular complexes, microspheres, nanoparticles, patches, and liposomes.

As used herein, the phrases "parenteral administration" and "administered parenterally" as used herein mean modes of administration other than enteral and topical administration, usually by injection, and includes, without limitation, intravenous, intramuscular, intraarterial, intrathecal, intracapsular, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. The phrases "systemic administration," "administered systemically", "peripheral administration" and "administered peripherally" as used herein mean the administration therapeutic compositions other than directly into a tumor such that it enters the animal's system and, thus, is subject to metabolism and other like processes.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent or encapsulating material, involved in maintaining the activity of or carrying or transporting the subject agents from one organ, or portion of the body, to another organ, or portion of the body. In addition to being "pharmaceutically acceptable" as that term is defined herein, each carrier must also be "acceptable" in the sense of being compatible with the other ingredients of the formulation. The pharmaceutical formulation comprising the one or more peptides as disclosed herein or a mutant, variant, analog or derivative thereof in combination with one or more pharmaceutically acceptable ingredients. The carrier can be in the form of a solid, semi-solid or liquid diluent, cream or a capsule. These pharmaceutical preparations are a further object of the invention. Usually the amount of active compounds is between 0.1-95% by weight of the preparation, preferably between 0.2-20% by weight in preparations for parenteral use and preferably between 1 and 50% by weight in preparations for oral administration. For the clinical use of the methods of the present invention, targeted delivery composition of the invention is formulated into pharmaceutical compositions or pharmaceutical formulations for parenteral administration, e.g., intravenous; mucosal, e.g., intranasal; enteral, e.g., oral; topical, e.g., transdermal; ocular, e.g., via corneal scarification or other mode of administration. The pharmaceutical composition contains a compound of the invention in combination with one or more pharmaceutically acceptable ingredients. The carrier can be in the form of a solid, semi-solid or liquid diluent, cream or a capsule.

The term "pharmaceutically acceptable carriers" is intended to include all solvents, diluents, or other liquid vehicle, dispersion or suspension aids, surface active agents, isotonic agents, thickening or emulsifying agents, preservatives, solid binders, lubricants and the like, as suited to the particular dosage form desired. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its functional derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

The term "pharmaceutical composition" is used herein refer to compositions or formulations that usually comprise an excipient, such as a pharmaceutically acceptable carrier that is conventional in the art and that is suitable for administration to mammals, and preferably humans or human cells. Such compositions can be specifically formulated for administration via one or more of a number of routes, including but not limited to, oral, ocular, parenteral, intravenous, intraarterial, subcutaneous, intranasal, sublingual, intraspinal, intracerebroventricular, and the like. In addition, compositions for topical (e.g., oral mucosa, respiratory mucosa) and/or oral administration can form solutions, suspensions, tablets, pills, capsules, sustained-release formulations, oral rinses, or powders, as known in the art are described herein. The compositions also can include stabilizers and preservatives. For examples of carriers, stabilizers and adjuvants, University of the Sciences in Philadelphia (2005) Remington: The Science and Practice of Pharmacy with Facts and Comparisons, 21st Ed.

In certain embodiments, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals such as sodium, lithium, potassium, calcium, magnesium and the like, as well as nontoxic ammonium, quaternary ammonium, and amine cations including, but not limited to ammonium, tetramethylanunonium, tetraethyl ammonium, methyl amine, dimethyl amine, trimethylamine, triethylamine, ethylamine, and the like (see, e.g., Berge S. M., et al. (1977) J. Pharm. Sci. 66, 1, which is incorporated herein by reference).

The term "pharmaceutically acceptable esters" refers to the relatively nontoxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters.

As used herein, "pharmaceutically acceptable salts or prodrugs" are salts or prodrugs that are, within the scope of sound medical judgment, suitable for use in contact with the tissues of subject without undue toxicity, irritation, allergic response, and the like, commensurate with a reasonable benefit/risk ratio, and effective for their intended use.

The term "prodrug" refers to compounds that are rapidly transformed in vivo to yield the functionally active one or more peptides as disclosed herein or a mutant, variant, analog or derivative thereof. A thorough discussion is provided in T. Higachi and V. Stella, "Pro-drugs as Novel Delivery Systems," Vol. 14 of the A. C. S. Symposium Series, and in Bioreversible Carriers in: Drug Design, ed. Edward B. Roche, American Pharmaceutical Association and Pergamon Press, 1987, both of which are hereby incorporated by reference. As used herein, a prodrug is a compound that, upon in vivo administration, is metabolized or otherwise converted to the biologically, pharmaceutically or therapeutically active form of the compound. A prodrug of the one or more peptides as disclosed herein or a mutant, variant, analog or derivative thereof can be designed to alter the metabolic stability or the transport characteristics of one or more peptides as disclosed herein or a mutant, variant, analog or derivative thereof, to mask side effects or toxicity, to improve the flavor of a compound or to alter other characteristics or properties of a compound. By virtue of knowledge of pharmacodynamic processes and drug metabolism in vivo, once a pharmaceutically active form of the one or more peptides as disclosed herein or a mutant, variant, analog or derivative thereof, those of skill in the pharmaceutical art generally can design prodrugs of the compound (see, e.g., Nogrady (1985) Medicinal Chemistry A Biochemical Approach, Oxford University Press, N.Y., pages 388-392). Conventional procedures for the selection and preparation of suitable prodrugs are described, for example, in "Design of Prodrugs," ed. H. Bundgaard, Elsevier, 1985. Suitable examples of prodrugs include methyl, ethyl and glycerol esters of the corresponding acid.

Parenteral Compositions

The pharmaceutical composition may be administered parenterally by injection, infusion, or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation.

Compositions for parenteral use may be provided in unit dosage forms (e.g., in single-dose ampoules), or in vials containing several doses and in which a suitable preservative may be added (see below). The composition may be in form of a solution, a suspension, an emulsion, an infusion device, or a delivery device for implantation, or it may be presented as a dry powder to be reconstituted with water or another suitable vehicle before use. Apart from the active agent(s), the composition may include suitable parenterally acceptable carriers and/or excipients. The active agent(s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing agents.

As indicated above, the pharmaceutical compositions according to the invention may be in a form suitable for sterile injection. To prepare such a composition, the suitable active agent(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

Pharmaceutical compositions of this invention suitable for parenteral administration comprise one or more peptides as disclosed herein or a mutant, variant, analog or derivative thereof in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions comprising one or more peptides as disclosed herein or a mutant, variant, analog or derivative thereof include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug, such as one or more peptides as disclosed herein or a mutant, variant, analog or derivative thereof in liposomes or microemulsions which are compatible with body tissue.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Controlled Release Parenteral Compositions

Controlled release parenteral compositions may be in form of aqueous suspensions, microspheres, microcapsules, magnetic microspheres, oil solutions, oil suspensions, or emulsions. The composition may also be incorporated in biocompatible carriers, liposomes, nanoparticles, implants, or infusion devices.

Materials for use in the preparation of microspheres and/or microcapsules are, e.g., biodegradable/bioerodible polymers such as polygalactia poly-(isobutyl cyanoacrylate), poly(2-hydroxyethyl-L-glutamnine), poly(lactic acid), polyglycolic acid, and mixtures thereof. Biocompatible carriers that may be used when formulating a controlled release parenteral formulation are carbohydrates (e.g., dextrans), proteins (e.g., albumin), lipoproteins, or antibodies. Materials for use in implants can be nonbiodegradable (e.g., polydimethyl siloxane) or biodegradable (e.g., poly(caprolactone), poly(lactic acid), poly(glycolic acid) or poly(ortho esters)) or combinations thereof.

Solid Dosage Forms for Oral Use

Formulations for oral use include tablets containing the active ingredient(s) in a mixture with non-toxic pharmaceutically acceptable excipients, and such formulations are known to the skilled artisan (e.g., U.S. Pat. Nos. 5,817,307; 5,824,300; 5,830,456; 5,846,526; 5,882,640; 5,910,304; 6,036,949; 6,036,949; and 6,372,218 hereby incorporated by reference). These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and anti-adhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the protein in a predetermined pattern (e.g., in order to achieve a controlled release formulation) or it may be adapted not to release the agent(s) until after passage of the stomach (enteric coating). The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or an enteric coating (e.g., based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose). Furthermore, a time delay material such as, e.g., glyceryl monostearate or glyceryl distearate, may be employed.

The solid tablet compositions may include a coating adapted to protect the composition from unwanted chemical changes, (e.g., chemical degradation prior to the release of the active substances). The coating may be applied on the solid dosage form in a similar manner as that described in Encyclopedia of Pharmaceutical Technology, supra.

The compositions of the invention may be mixed together in the tablet, or may be partitioned. In one example, a first agent is contained on the inside of the tablet, and a second agent is on the outside, such that a substantial portion of the second agent is released prior to the release of the first agent.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate, or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus, or spray drying equipment.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients. In one aspect, a solution of resolvin and/or protectin or precursor or analog thereof can be administered as eye drops for ocular neovascularization or ear drops to treat otitis.

Oral administration of peptides has been shown to work for other protein or peptide drugs as well. For example, oral administration of an anti-CD3 antibody has been shown to work in treatment of, for example, diabetes (Ishikawa et al. Diabetes. 2007 August; 56(8):2103-9. Epub 2007 Apr. 24), and autoimmune encephalomyelitis (Ochi et al. Nat Med. 2006 June; 12(6):627-35. Epub 2006 May 21). Without wishing to be bound by a theory, we suggest that this is possible via the gut associated lymphoid tissue (GALT). Accordingly, in some aspects of all the embodiments of the invention, the formulation of the peptides is oral formulation, and the methods are performed by administering the peptides orally.

Liquid dosage forms for oral administration of the compounds of the invention include pharmaceutically acceptable emulsions, microemulsions, solutions, suspensions, syrups and elixirs.

In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration of one or more peptides as disclosed herein or a mutant, variant, analog or derivative thereof include powders, sprays, ointments, pastes, creams, lotions, gels, solutions, patches and inhalants. The active compound may be mixed under sterile conditions with a pharmaceutically acceptable carrier, and with any preservatives, buffers, or propellants, which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of the compounds (resolvins and/or protectins and/or precursors or analogues thereof) of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel. In another aspect, biodegradable or absorbable polymers can provide extended, often localized, release of polypeptide agents. The potential benefits of an increased half-life or extended release for a therapeutic agent are clear. A potential benefit of localized release is the ability to achieve much higher localized dosages or concentrations, for greater lengths of time, relative to broader systemic administration, with the potential to also avoid possible undesirable side effects that may occur with systemic administration.

Bioabsorbable polymeric matrix suitable for delivery of the one or more peptides as disclosed herein or a mutant, variant, analog or derivative thereof can be selected from a variety of synthetic bioabsorbable polymers, which are described extensively in the literature. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephthalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317, 5,618,563, among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

Gene Therapy

One or more peptides as disclosed herein or a mutant, variant, analog or derivative thereof can be effectively used in treatment by gene therapy. See, generally, for example, U.S. Pat. No. 5,399,346, which is incorporated herein by reference. The general principle is to introduce the polynucleotide into a target cell in a patient.

Entry into the cell is facilitated by suitable techniques known in the art such as providing the polynucleotide in the form of a suitable vector, or encapsulation of the polynucleotide in a liposome.

A desired mode of gene therapy is to provide the polynucleotide in such a way that it will replicate inside the cell, enhancing and prolonging the desired effect. Thus, the polynucleotide is operably linked to a suitable promoter, such as the natural promoter of the corresponding gene, a heterologous promoter that is intrinsically active in liver, neuronal, bone, muscle, skin, joint, or cartilage cells, or a heterologous promoter that can be induced by a suitable agent.

Expression vectors compatible with eukaryotic cells, preferably those compatible with vertebrate cells, can be used to produce recombinant constructs for the expression of one or more peptides as disclosed herein or a mutant, variant, analog or derivative thereof, including fusion proteins with one or more peptides as disclosed herein or a mutant, variant, analog or derivative thereof. Eukaryotic cell expression vectors are well known in the art and are available from several commercial sources. Typically, such vectors are provided containing convenient restriction sites for insertion of the desired DNA segment. These vectors can be viral vectors such as adenovirus, adeno-associated virus, pox virus such as an orthopox (vaccinia and attenuated vaccinia), avipox, lentivirus, murine moloney leukemia virus, etc. Alternatively, plasmid expression vectors can be used.

Viral vector systems which can be utilized in the present invention include, but are not limited to, (a) adenovirus vectors; (b) retrovirus vectors; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. In a preferred embodiment, the vector is an adenovirus. Replication-defective viruses can also be advantageous.

The vector may or may not be incorporated into the cells genome. The constructs may include viral sequences for transfection, if desired. Alternatively, the construct may be incorporated into vectors capable of episomal replication, e.g. EPV and EBV vectors.

By "operably linked" is meant that a nucleic acid molecule and one or more regulatory sequences (e.g., a promoter) are connected in such a way as to permit expression and/or secretion of the product (e.g., a protein) of the nucleic acid molecule when the appropriate molecules (e.g., transcriptional activator proteins) are bound to the regulatory sequences. Stated another way, the term "operatively linked" as used herein refers to the functional relationship of the nucleic acid sequences with regulatory sequences of nucleotides, such as promoters, enhancers, transcriptional and translational stop sites, and other signal sequences. For example, operative linkage of nucleic acid sequences, typically DNA, to a regulatory sequence or promoter region refers to the physical and functional relationship between the DNA and the regulatory sequence or promoter such that the transcription of such DNA is initiated from the regulatory sequence or promoter, by an RNA polymerase that specifically recognizes, binds and transcribes the DNA. In order to optimize expression and/or in vitro transcription, it may be necessary to modify the regulatory sequence for the expression of the nucleic acid or DNA in the cell type for which it is expressed. The desirability of, or need of, such modification may be empirically determined. An operatively linked polynucleotide which is to be expressed typically includes an appropriate start signal (e.g., ATG) and maintains the correct reading frame to permit expression of the polynucleotide sequence under the control of the expression control sequence, and production of the desired polypeptide encoded by the polynucleotide sequence.

As used herein, the terms "promoter" or "promoter region" or "promoter element" have been defined herein, refers to a segment of a nucleic acid sequence, typically but not limited to DNA or RNA or analogues thereof, that controls the transcription of the nucleic acid sequence to which it is operatively linked. The promoter region includes specific sequences that are sufficient for RNA polymerase recognition, binding and transcription initiation. This portion of the promoter region is referred to as the promoter. In addition, the promoter region includes sequences which modulate this recognition, binding and transcription initiation activity of RNA polymerase. These sequences may be ds-acting or may be responsive to trans-acting factors. Promoters, depending upon the nature of the regulation may be constitutive or regulated.

The term "regulatory sequences" is used interchangeably with "regulatory elements" herein refers element to a segment of nucleic acid, typically but not limited to DNA or RNA or analogues thereof, that modulates the transcription of the nucleic acid sequence to which it is operatively linked, and thus act as transcriptional modulators. Regulatory sequences modulate the expression of gene and/or nucleic acid sequence to which they are operatively linked. Regulatory sequence often comprise "regulatory elements" which are nucleic acid sequences that are transcription binding domains and are recognized by the nucleic acid-binding domains of transcriptional proteins and/or transcription factors, repressors or enhancers etc. Typical regulatory sequences include, but are not limited to, transcriptional promoters, inducible promoters and transcriptional elements, an optional operate sequence to control transcription, a sequence encoding suitable mRNA ribosomal binding sites, and sequences to control the termination of transcription and/or translation. Included in the term "regulatory elements" are nucleic acid sequences such as initiation signals, enhancers, and promoters, which induce or control transcription of protein coding sequences with which they are operatively linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring form of a protein. In some instances the promoter sequence is recognized by the synthetic machinery of the cell, or introduced synthetic machinery, required for initiating transcription of a specific gene.

Regulatory sequences can be a single regulatory sequence or multiple regulatory sequences, or modified regulatory sequences or fragments thereof. Modified regulatory sequences are regulatory sequences where the nucleic acid sequence has been changed or modified by some means, for example, but not limited to, mutation, methylation etc.

Regulatory sequences useful in the methods as disclosed herein are promoter elements which are sufficient to render promoter-dependent gene expression controllable for cell type-specific, tissue-specific or inducible by external signals or agents (e g enhancers or repressors); such elements may be located in the 5' or 3' regions of the native gene, or within an intron.

As used herein, the term "tissue-specific promoter" means a nucleic acid sequence that serves as a promoter, i.e., regulates expression of a selected nucleic acid sequence operably linked to the promoter, and which selectively affects expression of the selected nucleic acid sequence in specific cells of a tissue.

In some embodiments, it can be advantageous to direct expression of one or more peptides as disclosed herein or a mutant, variant, analog or derivative thereof in a tissue- or cell-specific manner. Muscle-specific expression can be achieved, for example, using the skeletal muscle MKC promoter (as disclosed in U.S. Patent Application WO2007/100722, which is incorporated herein by reference), or other muscle-specific promoters, such as α-myosin heavy chain, myosin light chain-2 (which is specific for skeletal muscle (Shani et al., Nature, 314; 283-86, 1985), gonadotrophic releasing hormone gene control region which is active in the hypothalamus (Mason et al, Science, 234; 1372-78, 1986), and smooth muscle promoter SM22a, which are all commonly known in the art.

The term "constitutively active promoter" refers to a promoter of a gene which is expressed at all times within a given cell. Exemplary promoters for use in mammalian cells include cytomegalovirus (CMV), and for use in prokaryotic cells include the bacteriophage T7 and T3 promoters, and the like. The term "inducible promoter" refers to a promoter of a gene which can be expressed in response to a given signal, for example addition or reduction of an agent. Non-limiting examples of an inducible promoter are "tet-on" and "tet-off" promoters, or promoters that are regulated in a specific tissue type.

In a specific embodiment, viral vectors that contain nucleic acid sequences encoding the one or more peptides as disclosed herein or a mutant, variant, analog or derivative thereof are used. For example, a retroviral vector can be used (see Miller et al., Meth. Enzymol. 217:581-599 (1993)). These retroviral vectors contain the components necessary for the correct packaging of the viral genome and integration into the host cell DNA. More detail about retroviral vectors can be found in Boesen et al., Biotherapy 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

The production of a recombinant retroviral vector carrying a gene of interest is typically achieved in two stages. First, sequence encoding one or more peptides as disclosed herein or a mutant, variant, analog or derivative thereof can be inserted into a retroviral vector which contains the sequences necessary for the efficient expression of the metabolic regulators (including promoter and/or enhancer elements which can be provided by the viral long terminal repeats (LTRs) or by an internal promoter/enhancer and relevant splicing signals), sequences required for the efficient packaging of the viral RNA into infectious virions (e.g., a packaging signal (Psi), a tRNA primer binding site (−PBS), a 3' regulatory sequence required for reverse transcription (+PBS)), and a viral LTRs). The LTRs contain sequences required for the association of viral genomic RNA, reverse transcriptase and integrase functions, and sequences involved in directing the expression of the genomic RNA to be packaged in viral particles.

Following the construction of the recombinant retroviral vector, the vector DNA is introduced into a packaging cell line. Packaging cell lines provide viral proteins required in trans for the packaging of viral genomic RNA into viral particles having the desired host range (e.g., the viral-encoded core (gag), polymerase (pol) and envelope (env) proteins). The host range is controlled, in part, by the type of envelope gene product expressed on the surface of the viral particle. Packaging cell lines can express ecotrophic, amphotropic or xenotropic envelope gene products. Alternatively, the packaging cell line can lack sequences encoding a viral envelope (env) protein. In this case, the packaging cell line can package the viral genome into particles which lack a membrane-associated protein (e.g., an env protein). To produce viral particles containing a membrane-associated protein which permits entry of the virus into a cell, the packaging cell line containing the retroviral sequences can be transfected with sequences encoding a membrane-associated protein (e.g., the G protein of vesicular stomatitis virus (VSV)). The transfected packaging cell can then produce viral particles which contain the membrane-associated protein expressed by the transfected packaging cell line; these viral particles which contain viral genomic RNA derived from one virus encapsidated by the envelope proteins of another virus are said to be pseudotyped virus particles.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Another preferred viral vector is a pox virus such as a vaccinia virus, for example an attenuated vaccinia such as Modified Virus Ankara (MVA) or NYVAC, an avipox such as fowl pox or canary pox. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In another embodiment, lentiviral vectors are used, such as the HIV based vectors described in U.S. Pat. Nos. 6,143,520; 5,665,557; and 5,981,276, which are herein incorporated by reference. Use of Adeno-associated virus (AAV) vectors is also contemplated (Walsh et al., Proc. Soc. Exp. Biol. Med. 204:289-300 (1993); and U.S. Pat. No. 5,436,146, which are incorporated herein by reference).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

U.S. Pat. No. 5,676,954 (which is herein incorporated by reference) reports on the injection of genetic material, complexed with cationic liposome carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provides methods for delivering DNA-cationic lipid complexes to mammals. Such cationic lipid complexes or nanoparticles can also be used to deliver protein.

A gene or nucleic acid sequence can be introduced into a target cell by any suitable method. For example, one or more peptides as disclosed herein or a mutant, variant, analog or derivative thereof constructs can be introduced into a cell by transfection (e.g., calcium phosphate or DEAE-dextran mediated transfection), lipofection, electroporation, microinjection (e.g., by direct injection of naked DNA), biolistics, infection with a viral vector containing a muscle related transgene, cell fusion, chromosome-mediated gene transfer, microcell-mediated gene transfer, nuclear transfer, and the like. A nucleic acid encoding one or more peptides as disclosed herein or a mutant, variant, analog or derivative thereof can be introduced into cells by electroporation (see, e.g., Wong and Neumann, Biochem. Biophys. Res. Commun. 107:584-87 (1982)) and biolistics (e.g., a gene gun; Johnston and Tang, Methods Cell Biol. 43 Pt A:353-65 (1994); Fynan et al., Proc. Natl. Acad. Sci. USA 90:11478-82 (1993)).

In certain embodiments, a gene or nucleic acid sequence encoding one or more peptides as disclosed herein or a mutant, variant, analog or derivative thereof can be introduced into target cells by transfection or lipofection. Suitable agents for transfection or lipofection include, for example, calcium phosphate, DEAE dextran, lipofectin, lipfectamine, DIMRIE C, Superfect, and Effectin (Qiagen), unifectin, maxifectin, DOTMA, DOGS (Transfectam; dioctadecylamidoglycylspermine), DOPE (1,2-dioleoyl-sn-glycero-3-phosphoethanolamine), DOTAP (1,2-dioleoyl-3-trimethylammonium propane), DDAB (dimethyl dioctadecylammonium bromide), DHDEAB (N,N-di-n-hexadecyl-N,N-dihydroxyethyl ammonium bromide), HDEAB (N-n-hexadecyl-N,N-dihydroxyethylammonium bromide), polybrene, poly(ethylenimine) (PEI), and the like. (See, e.g., Banerjee et al., Med. Chem. 42:4292-99 (1999); Godbey et al., Gene Ther. 6:1380-88 (1999); Kichler et al., Gene Ther. 5:855-60 (1998); Birchaa et al., J. Pharm. 183:195-207 (1999), incorporated herein by reference in their entireties).

Methods known in the art for the therapeutic delivery of agents such as proteins and/or nucleic acids can be used for the delivery of a polypeptide or nucleic acid encoding one or more peptides as disclosed herein or a mutant, variant, analog or derivative thereof, e.g., cellular transfection, gene therapy, direct administration with a delivery vehicle or pharmaceutically acceptable carrier, indirect delivery by providing recombinant cells comprising a nucleic acid encoding a targeting fusion polypeptide of the invention.

Various delivery systems are known and can be used to directly administer therapeutic polypeptides such as the one or more peptides as disclosed herein or a mutant, variant, analog or derivative thereof and/or a nucleic acid encoding one or more peptides as disclosed herein or a mutant, variant, analog or derivative thereof, e.g., encapsulation in liposomes, microparticles, microcapsules, recombinant cells capable of expressing the compound, and receptor-mediated endocytosis (see, e.g., Wu and Wu, 1987, J. Biol. Chem. 262:4429-4432). Methods of introduction can be enteral or parenteral and include but are not limited to intradermal, intramuscular, intraperitoneal, intravenous, subcutaneous, pulmonary, intranasal, intraocular, epidural, and oral routes. The agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105).

Thus, a wide variety of gene transfer/gene therapy vectors and constructs are known in the art. These vectors are readily adapted for use in the methods of the present invention. By the appropriate manipulation using recombinant DNA/molecular biology techniques to insert an operatively linked polypeptide encoding nucleic acid segment into the selected expression/delivery vector, many equivalent vectors for the practice of the methods described herein can be generated.

Other Embodiments

From the foregoing description, it will be apparent that variations and modifications may be made to the invention described herein to adopt it to various usages and conditions. Such embodiments are also within the scope of the following claims.

The disclosure also contemplates an article of manufacture, which is a labeled container for providing the one or more peptides as disclosed herein or a mutant, variant, analog or derivative thereof. An article of manufacture comprises packaging material and a pharmaceutical agent of the one or more peptides as disclosed herein or a mutant, variant, analog or derivative thereof, contained within the packaging material.

The pharmaceutical agent in an article of manufacture is any of the compositions of the present invention suitable for providing the one or more peptides as disclosed herein or a mutant, variant, analog or derivative thereof and formulated into a pharmaceutically acceptable form as described herein according to the disclosed indications. Thus, the composition can comprise the one or more peptides as disclosed herein or a mutant, variant, analog or derivative thereof or a DNA molecule which is capable of expressing such a peptide.

The article of manufacture contains an amount of pharmaceutical agent sufficient for use in treating a condition indicated herein, either in unit or multiple dosages. The packaging material comprises a label which indicates the use of the pharmaceutical agent contained therein.

The label can further include instructions for use and related information as may be required for marketing. The packaging material can include container(s) for storage of the pharmaceutical agent.

As used herein, the term packaging material refers to a material such as glass, plastic, paper, foil, and the like capable of holding within fixed means a pharmaceutical agent. Thus, for example, the packaging material can be plastic or glass vials, laminated envelopes and the like containers used to contain a pharmaceutical composition including the pharmaceutical agent.

In preferred embodiments, the packaging material includes a label that is a tangible expression describing the contents of the article of manufacture and the use of the pharmaceutical agent contained therein.

EXAMPLES

Example 1. Testing of Anti-Inflammatory Potential in a Mouse Sepsis Model

The ability of peptide drugs was tested to for their potential for the reduction of inflammatory cytokines following treatment with purified bacterial lipopolysaccharide (LPS)—a major component of bacterial cell wall of Gram-negative bacteria. A model of inflammation was used wherein mice were injected with LPS, which induced a transient immune response and a surge of serum inflammatory cytokines. The immune response peaks after 90 minutes and subsides after 24 hours. The levels of key serum inflammatory markers were compared between mice treated and untreated with LPS 90 minutes after injection.

We designed 18 different peptides based on the hAAT sequence (Accession #AAB59371), and had these synthesized using conventional FMOC chemistry. To assess in vivo anti-inflammatory and therapeutic potential, the peptides were tested in a mouse lipopolysaccharide (LPS) challenge model with serum TNFα levels as readout. Using dexamethasone as reference, groups of 3 animals were IP injected with 0.2 mg/kg peptide 2 hours prior to an LPS challenge, and serum TNFα levels determined 30 min after the LPS challenge, by ELISA. The best performing peptide reduced serum TNFα levels equivalent to those achieved with 1 mg/kg dexamethasone. Next, shortened versions of this peptide were synthesized, tested in the mouse LPS challenge model, and a 17 amino acid peptide, SP16, emerged as a lead development candidate for further characterization. Next, SP16 was tested in a lethal endotoxemia model, which models endotoxemia following acute radiation exposure, where Gram negative bacteria leaking from the gastrointestinal system can cause lethal endotoxemia. In this experiment, peptide treatment improved survival (FIG. 7). In vitro, SP16 lowers LPS-induced NFκB activation in THP1 cells, consistent with the in vivo anti-inflammatory effect.

Mice were injected with 0.5, 0.1, 0.02 and 0.004 mg of each peptide. Mice were also treated with dexamethasone as a positive control and vehicle as a negative control. Two hours later each mouse was injected with LPS. Samples were taken 90 minutes after LPS injection.

Figure 4:
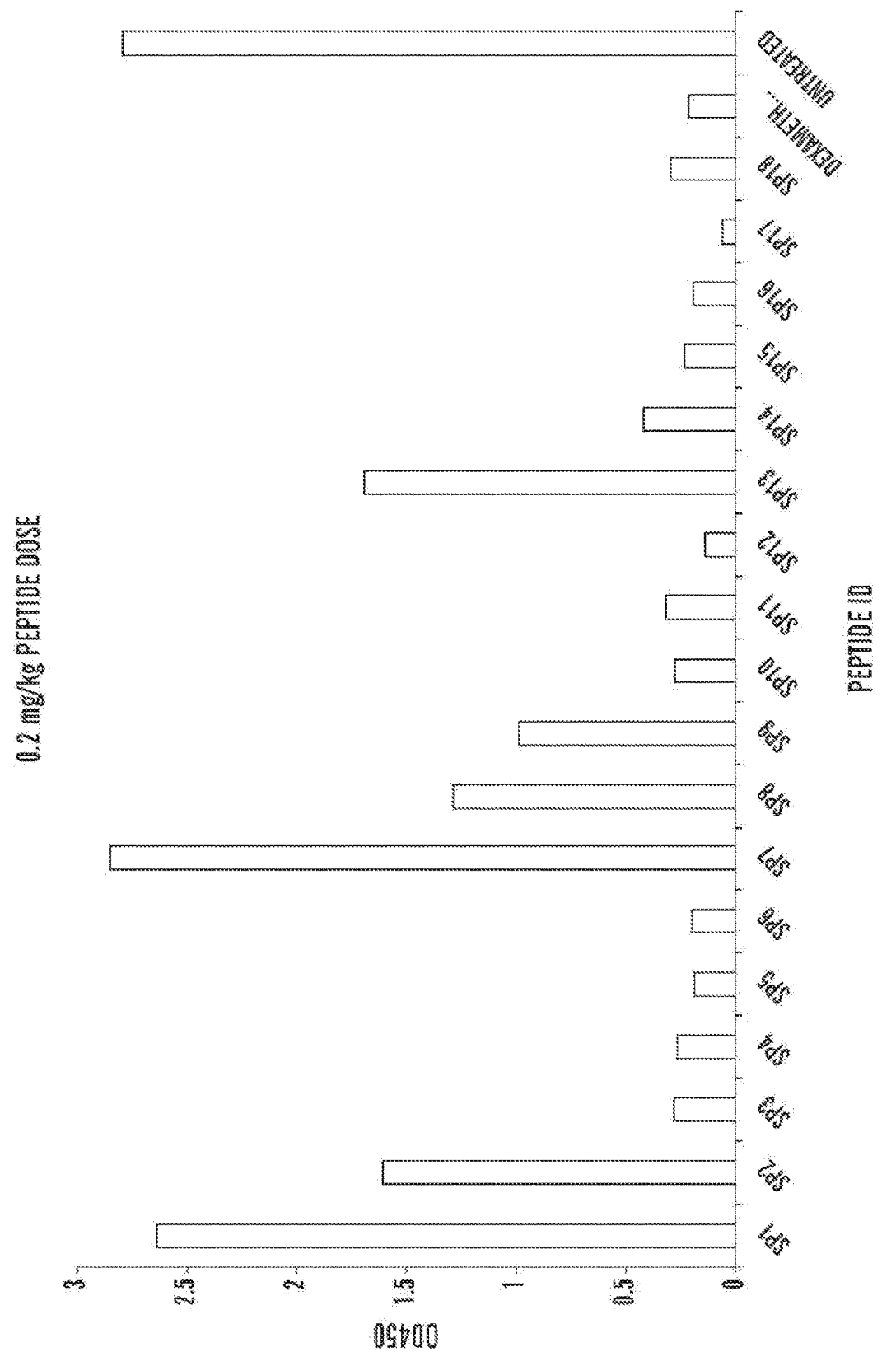
FIG. 4 is a bar graph showing TNF-α levels in blood of mice injected with 0.004 mg of various peptides.

Results are shown in FIGS. 3 and 4. FIG. 3 shows TNF-α levels from blood in mice injected with each amount of each peptide. FIG. 4 shows only the results for mice injected with 0.004 mg of each peptide.

The results shows that the peptides described herein are effective in decreasing TNF-α levels and thus are effective in reducing inflammation in mammalian subjects.

Example 2. Alanine Screened Peptides in Sepsis Mouse Model

To evaluate the effect of different amino acids in the SP16 peptide for the immunomodulating effect, we created an alanine screen. The different peptides in the alanine screen are shown in Table B. FIG. 10 shows that both the N- and C-terminally alanine-substituted peptides, where the 3 most terminal amino acids had been replaced with alanine, lost most of their ability to reduce TNF-alpha levels. The peptides wherein the substitution occurred within amino acids 4-14 of SP16, appeared to maintain and rather improve their capacity to reduce TNF-alpha levels compared to the control Dexamethasone. The LPS mouse model is an established model for sepsis in humans and thus we conclude that peptides wherein the amino acids 1-3 and 15-17 are present, can be effectively used in humans to treat or prevent sepsis in conditions, such as burns or acute radiation, which expose humans to a high risk of developing endotoxemia.

Example 3. Testing of Anti-Inflammatory Potential in a Collagen Antibody Induced Arthritis (CAIA) Model of Rheumatoid Arthritis The ability of peptide drugs was tested to for their potential to reduce inflammation and paw edema in a mouse arthritis model: the CAIA model. Balb/c mice were injected with a collagen antibody cocktail on Day 0 and received an LPS boost on Day 3. Following the LPS boost, the paw swelling was scored for each paw. For the results shown in FIG. 5, animals were dosed with 0.2 mg/kg of the peptide set forth in SEQ ID NO:1 (also referred to as SP16), daily. In FIG. 6, Balb/c mice were intravenously injected with a collagen antibody cocktail (MD BioSciences) on Day 0 and intraperitoneally injected with LPS on Day 3. Paw swelling was determined on Days 0, 3, 4, 5, 6 and 7, and the graph shows cumulative scores for all paws of each experimental group of 5 animals. Untreated control did not receive the CAIA cocktail or LPS. The mock group received both the antibody cocktail and LPS boost. Dexamethasone was administered daily at 1 mg/kg. The peptide set forth in SEQ ID NO:1 was dissolved in water and administered intraperitoneally, at 0.6 mg/kg daily, or a one-time dose of 0.6 mg/kg on day 3.

Figure 9:
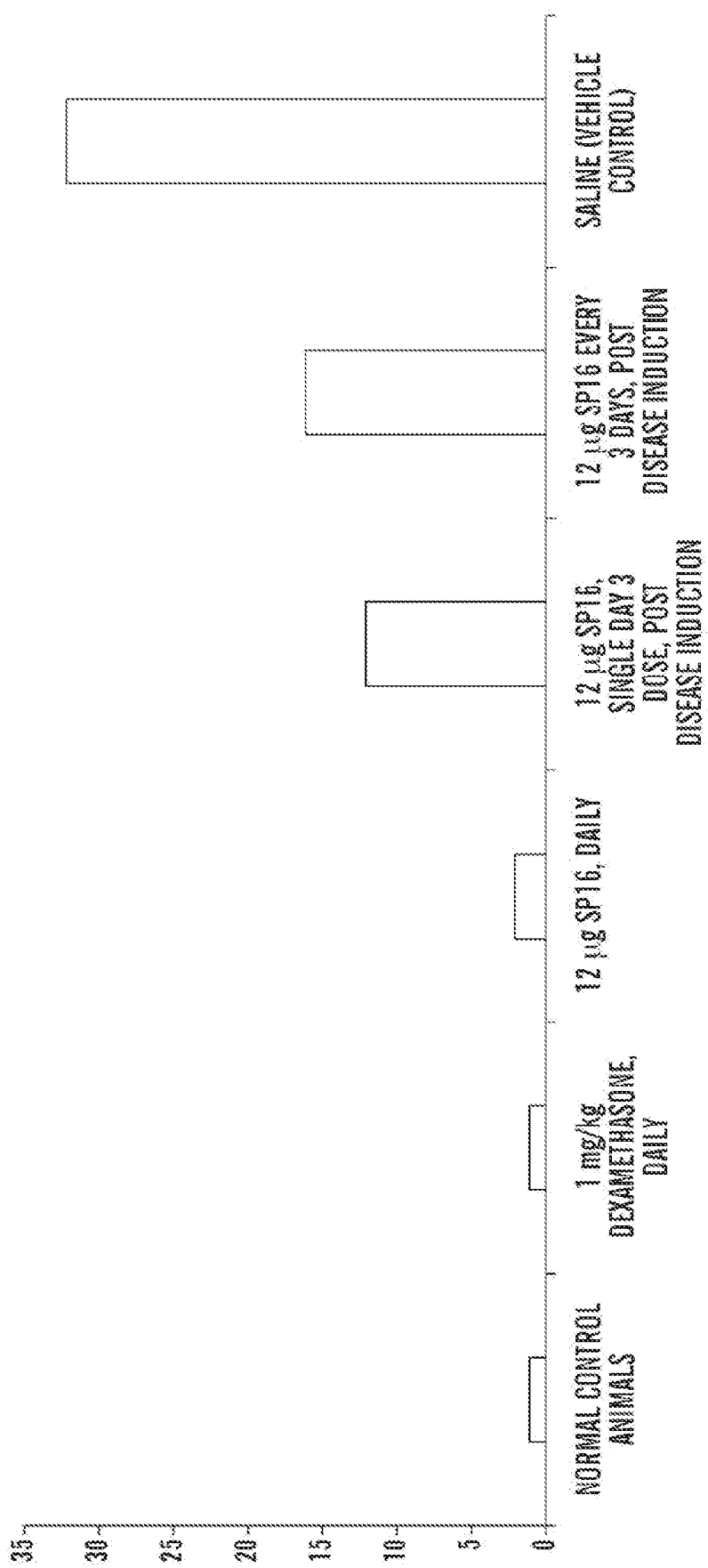
FIG. 9 is a graph summarizing data from a study in the mouse CAIA Rheumatoid Arthritis model. The graph shows cumulative swelling scores for all paws at the peak of disease (Day 7) for groups of 5 animals. Balb/c mice were IV injected with a collagen antibody cocktail (MD BioSciences) on Day 0 and IP injected with LPS on Day 3. Normal Control Animals received no injections and served as disease-free baseline control. Daily SP16 injection provided protection equivalent to Dexamethasone.

FIG. 9 shows efficacy of SP16 in the preclinical CAIA mouse model of RA. Graph summarizes data from a study in the mouse CAIA RA model. The graph shows cumulative swelling scores for all paws at the peak of disease (Day 7) for groups of 5 animals. Balb/c mice were injected intravenously with a collagen antibody cocktail (MD Biosciences) on Day 0 and injected intraperitoneally with LPS on Day 3. Normal control animals received no injections and served as disease-free baseline control. We show that daily SP16 injection provided protection equivalent to Dexamethasone.

Figure 5:
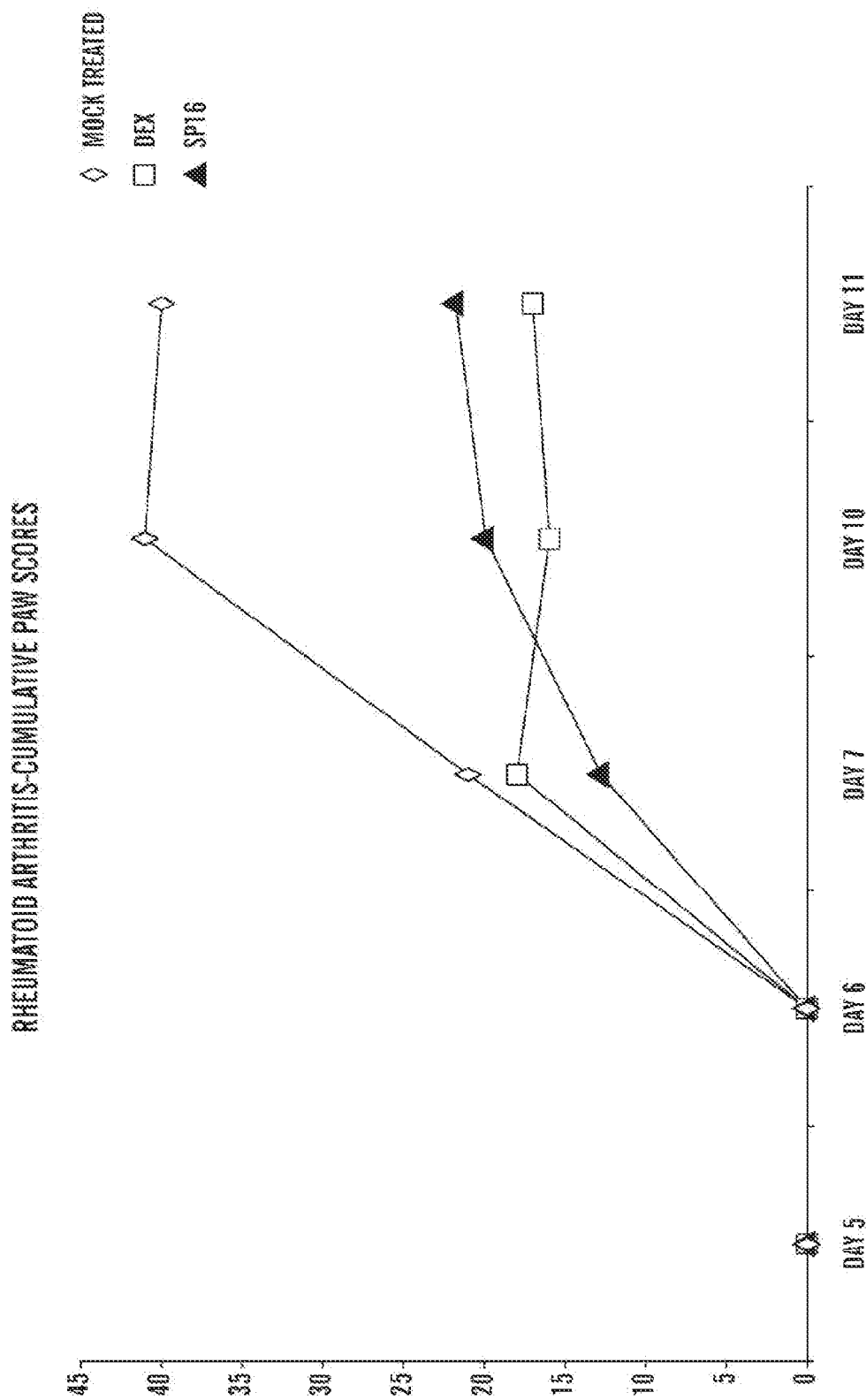
FIG. 5 is a line graph showing cumulative paw scores for mock treated, dexamethasone treated and peptide (SEQ ID NO: 1, also referred to as SP16) in a collagen antibody induced arthritis (CAIA) rat model.
Figure 6:
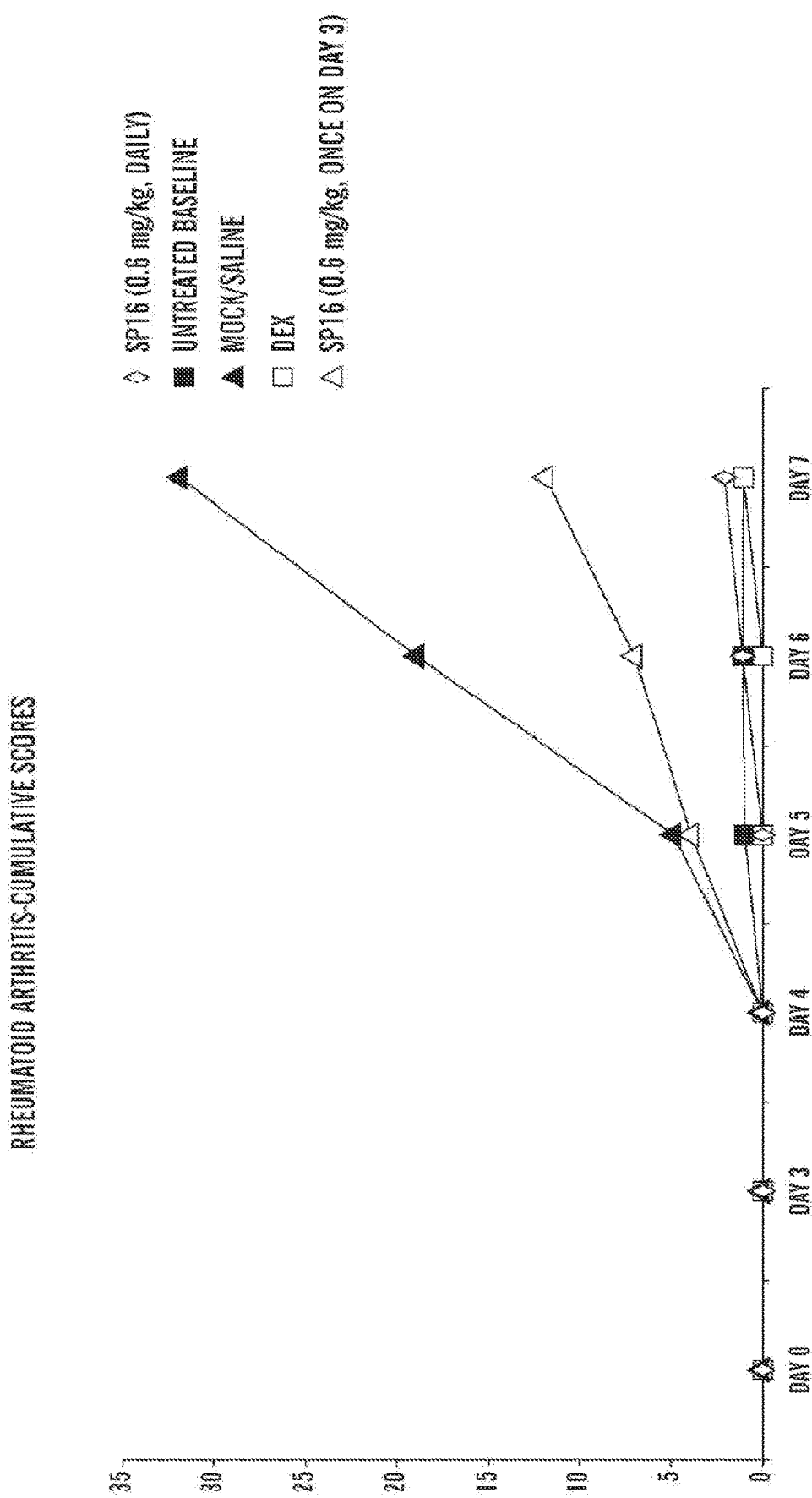
FIG. 6 is a line graph showing cumulative paw scores for mock treated, dexamethasone treated and peptide (SEQ ID NO: 1, also referred to as SP16) in a collagen antibody induced arthritis (CAIA) rat model.

As shown in FIGS. 5, 6, and 9 the peptide: VKFNKPFVFLMIEQNTK (SEQ ID NO:1) is an effective anti-inflammatory and/or immune-modulating agent in the sepsis model.

Example 4. SP16 Improves Glycemic Control in the db/db Model Type II Diabetes

Encouraged by the sepsis and RA data, we hypothesized whether SP16 would protect db/db mice, a type II diabetes (T2DM) model, from gluco- and lipotoxicity induced β-cell loss and reduce insulin resistance (25, 39). To test this hypothesis, a study was designed and executed in db/db animals. We started a study in the db/db model of T2DM because it is easier to manage (due to timing and synchronized onset of overt diabetes) and thus more cost effective than a study in NOD mice.

In the db/db model, SP16 treatment resulted in lowered non-fasted blood glucose and HbA1c levels, increased C-peptide levels and improved glucose tolerance (FIG. 8). Non-fasted blood glucose and glucose tolerance were improved over the vehicle control group, although the Rosiglitazone group showed better values than the SP16 group. Together, these data show that SP16 treatment improved glycemic control in an established type II diabetes model.

These data, together with the Sepsis and RA results, show that SP16 possesses the anti-inflammatory and immune-modulating properties of the parent protein hAAT, thus providing a much more cost-effective way of treatment as the size of the newly discovered peptide fragment is significantly smaller than that of hAAT.

Example 5. SP16 Peptide is a Toll Like Receptor-2 Agonist

Toll-like receptor 2 (TLR-2) plays a role in the immune system and it is a member of the Toll-like receptor (TLR) family which plays a fundamental role in pathogen recognition and activation of innate immunity. TLR-2 gene is expressed most abundantly in peripheral blood leukocytes, and has been shown to mediate host response to Gram-positive bacteria and yeast via stimulation of NF-kappaB.

Our data from engineered cell lines show that SP16 activates the TLR-2 signaling pathway, but not TLR-4 signaling. This is interesting because another immune modulating peptide, DiaPep277, which shares no sequence similarity with SP16, has a similar TLR activation profile. Without wishing to be bound by a theory, based on these observations, we suggest that SP16 acts through the TLR2 receptor, and possible the T-cell receptor, to drive cytokine secretion to a Th2 anti-inflammatory cytokine profile (IL-4 and IL-10). In autoimmune diseases, SP16 is predicted to induce expansion of regulatory T-cell populations and thereby shift the inflammatory response towards a regulatory response.

Figure 11:
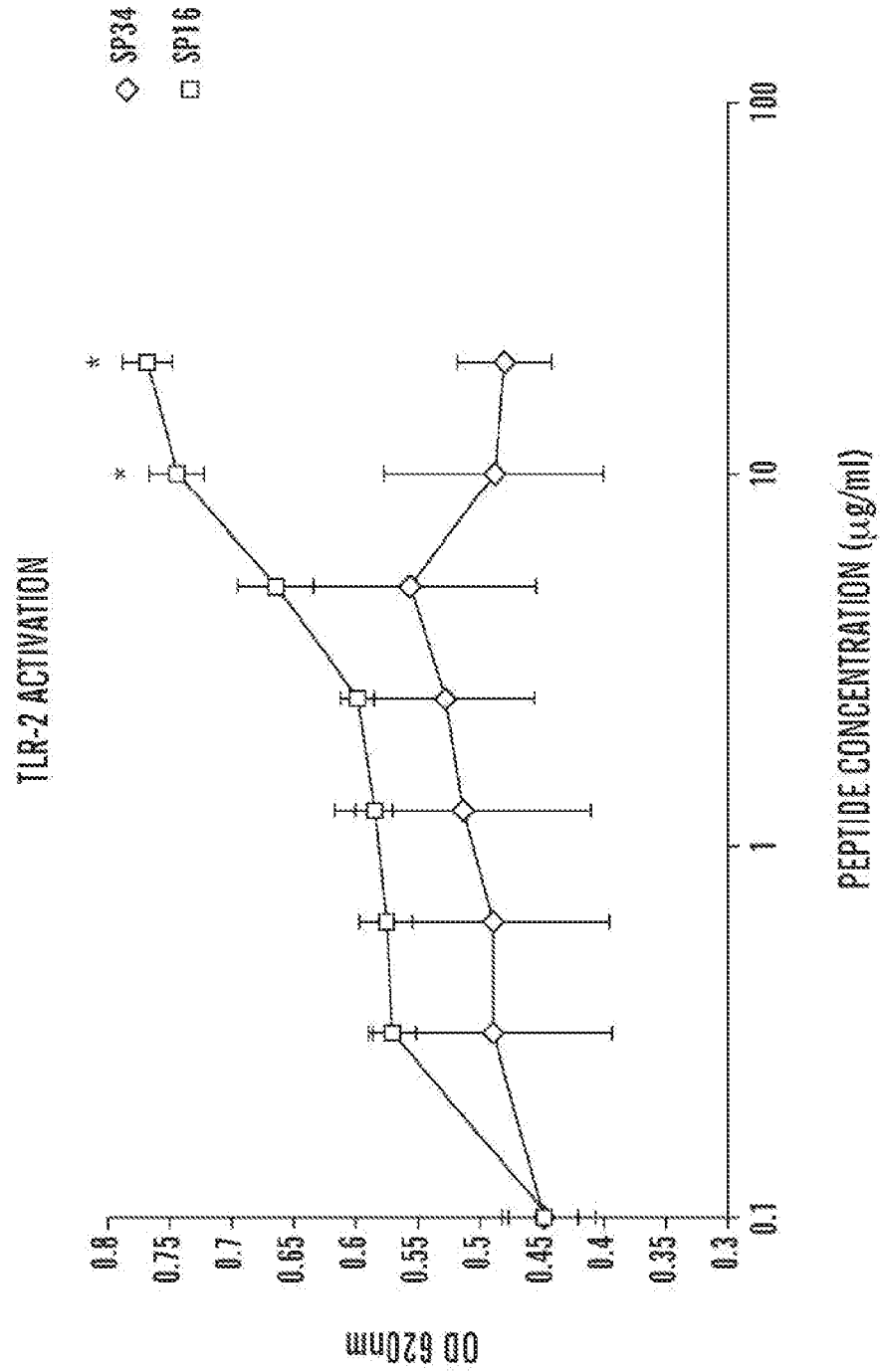
FIG. 11 shows that SP16 is a TLR2 agonist. Graph summarizing representative data from assays with an engineered TLR-2 indicator cell line (HEK-Blue™ mTLR2, Invivogen). Cells were incubated with the indicated concentrations of peptide for 24 hours. Upon TLR2 activation, the cells secrete alkaline phosphatase which can be assayed. The assay was done in triplicate and averages with standard deviations are plotted. SP16 exhibited TLR-2 ligand properties, inducing TLR-2 signaling in a dose dependent manner. The SP34 scrambled control peptide showed no TLR2 induction. *$p<0.05$, compared to scrambled control (SP34).

Specifically, FIG. 11 shows that SP16 is a TLR2 agonist. Graph summarizing data from an experiment with an engineered TLR-2 indicator cell line (HEK-BLUE™ mTLR2, Invivogen). Cells were incubated with the indicated concentrations of peptide for 24 hours. Upon TLR2 activation, the cells secrete alkaline phosphatase which can be assayed. The assay was done in triplicate and averages with standard deviations are plotted. SP16 exhibited TLR-2 ligand properties, inducing TLR-2 signaling in a dose dependent manner. The a scrambled control peptide (SP34) showed no TLR2 induction. *$p<0.05$, compared with scrambled control (SP34).

Figure 12:
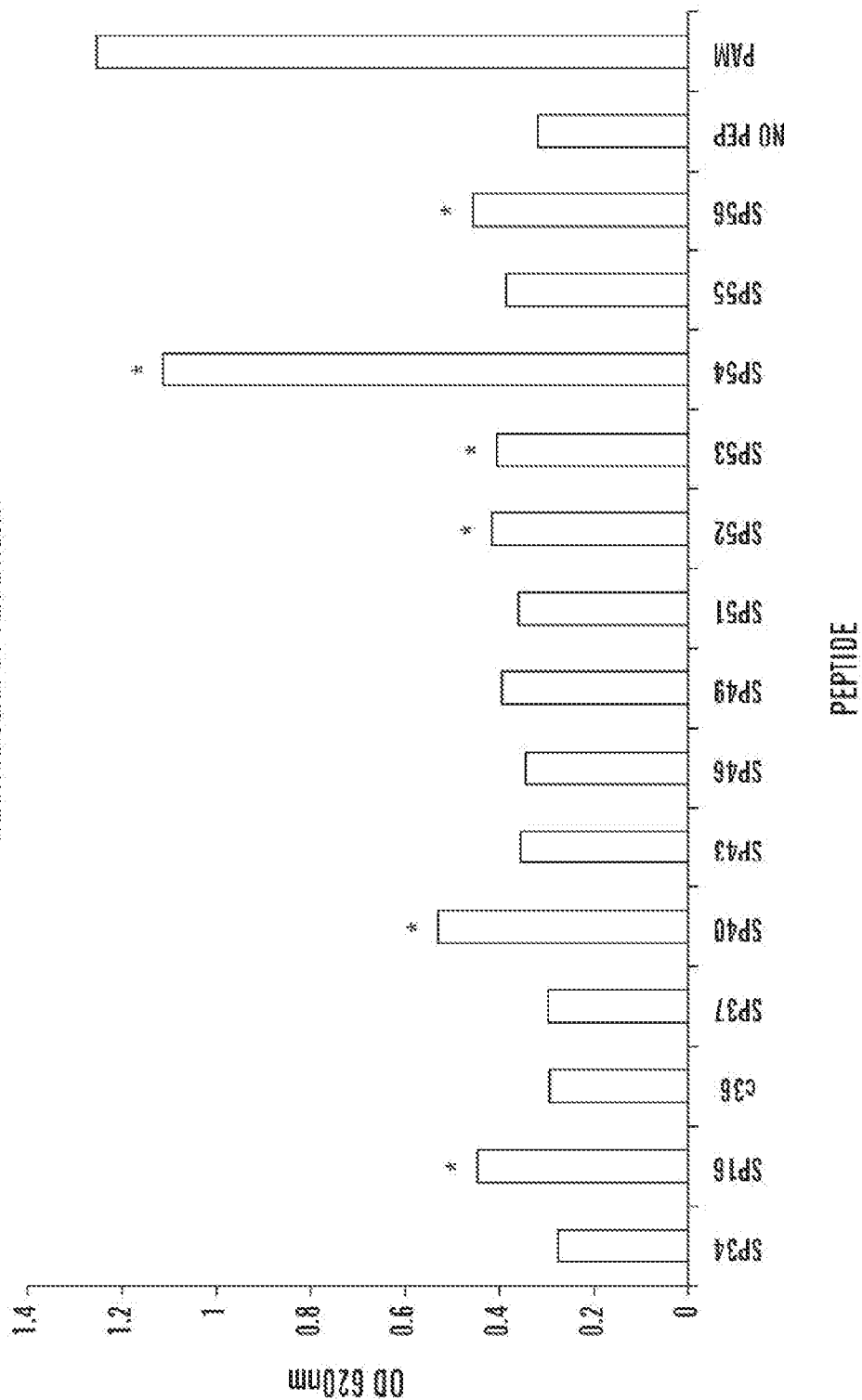
FIG. 12 shows structure activity relationship analysis for SP16. Graph summarizing data from an experiment where an engineered TLR-2 indicator cell line (HEK-Blue™ mTLR2, Invivogen) was used to test the impact of substituting amino acid residues of the SP16 peptide with alanine ("alanine scan"). Cells were incubated with 20 μg/ml of the indicated peptides for 24 hours. Upon TLR2 activation, the cells secrete alkaline phosphatase which can be assayed. The assay was done in triplicate and averages are plotted. Peptide sequences are shown in the following figure. *$p<0.05$, compared with scrambled control (SP34).

FIG. 12 shows structure activity relationship analysis for SP16. Graph summarizing data from an experiment where an engineered TLR-2 indicator cell line (HEK-Blue™ mTLR2, Invivogen) was used to test the impact of substituting amino acid residues of the SP16 peptide with alanine ("alanine scan"). Cells were incubated with 20 μg/ml of the indicated peptides for 24 hours. Upon TLR2 activation, the cells secrete alkaline phosphatase which can be assayed. The assay was done in triplicate and averages are plotted. Peptide sequences are shown in the following figure. *$p<0.05$, compared with scrambled control (SP34).

FIG. 13 shows structure activity relationship analysis for SP16. Table showing the amino acid sequences of peptides that were tested using a TLR-2 indicator cell line (See data in FIG. 12). The right side of the table summarizes the peptides' impact on TLR-2 signaling (* indicates low, ***** indicates high, N/A had no impact on signaling).

The data suggest the first three residues contribute to inducing TLR-2 signaling. If residues 1-3 are substituted with alanines (SP37), the mutant peptide has no impact on TLR2. However, when substituted individually (SP52-SP54), the peptides retain the ability to stimulate TLR-2.

Surprisingly, substitution of the phenyl alanine residue at position 3 with a smaller alanine residue enhances the ability to stimulate TLR-2 signaling compared to SP16.

Example 6. Oral Administration

FIG. 16 shows a graph summarizing data from a study in the mouse CAIA Rheumatoid Arthritis model. The graph shows the average cumulative swelling (clinical) scores for all paws at the peak of disease (Day 7) for groups of 5 animals. Balb/c mice were IV injected with a collagen antibody cocktail (MD BioSciences) on Day 0 and IP injected with LPS on Day 3. Normal Control Animals received no injections and served as disease-free baseline control. SP16 was provided daily by intraperitoneal injection (Dose: 12 ug/animal) or by oral gavage (Dose: 25 or 50 ug/animal). Daily SP16 injection provided protection equivalent to daily administration of 1 mg/kg Dexamethasone.

Example 7. In Vitro Data

Figure 17:
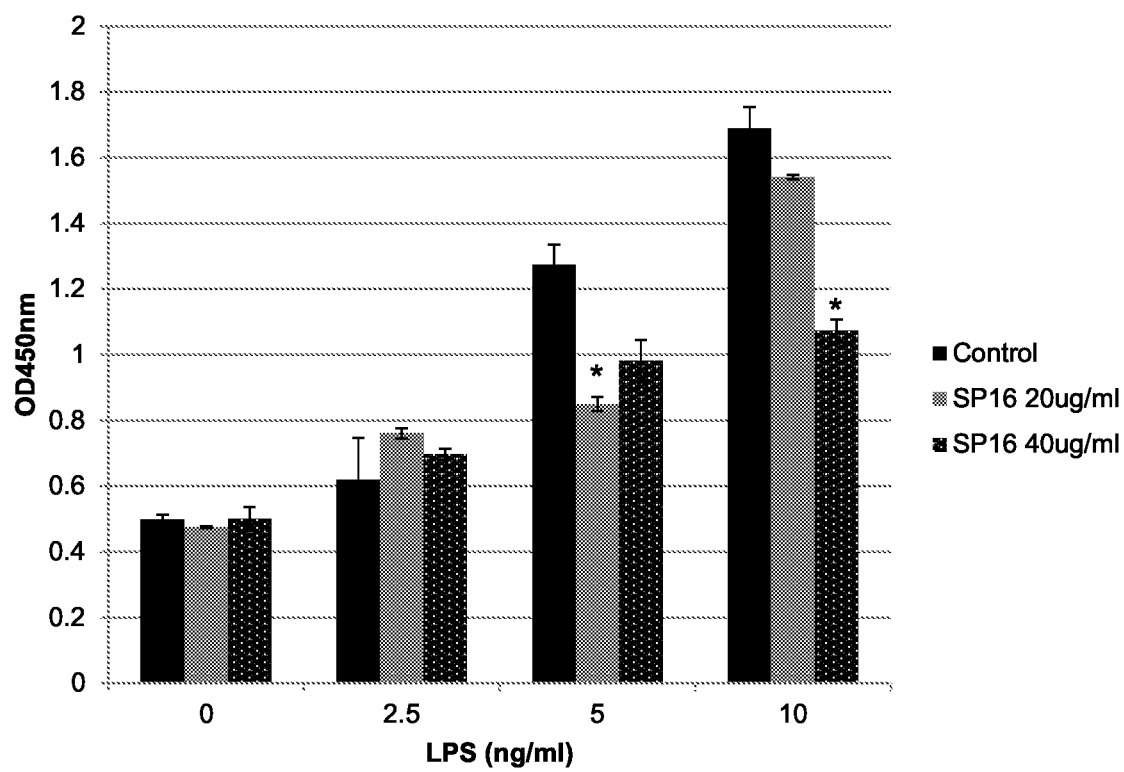
FIG. 17 depicts a graph with data from an experiment with mouse RAW (macrophage) cells. Cells were incubated with 20 or 40 ug/ml of SP16 peptide, as well as 0, 2.5, 5 or 10 ng/ml LPS, for 24 hours. Upon LPS stimulation, the cells secrete the inflammatory cytokine IL-6, which was measured by ELISA. The assay was done in triplicate and averages with standard deviations are plotted. SP16 lowered LPS-induced IL-6 secretion consistent with its anti-inflammatory function. (*) Indicates $p<0.05$ compared to scrambled peptide control.

FIG. 17 depicts a graph with data from an experiment with mouse RAW (macrophage) cells. Cells were incubated with 20 or 40 ug/ml of SP16 peptide, as well as 0, 2.5, 5 or 10 ng/ml LPS, for 24 hours. Upon LPS stimulation, the cells secrete the inflammatory cytokine IL-6, which was measured by ELISA. The assay was done in triplicate and averages with standard deviations are plotted. SP16 lowered LPS-induced IL-6 secretion consistent with its anti-inflammatory function. (*) indicates $p<0.05$ compared to scrambled peptide control.

Example 8. Treatment of NOD Model of Diabetes

NOD (non-obese diabetic) mice spontaneously develop overt, insulin-dependent type I diabetes. The NOD model is recommended by the FDA for preclinical testing of therapeutic agents for type I diabetes. Disease onset typically occurs at 12-14 weeks of age, with peri-insulitis detectable from about 4 weeks of age and developing into severe insulitis at 10 weeks of age. The autoimmune destruction of β-cells is thought to arise from dysregulation of multiple tolerance pathways, leading to islet infiltration with monocytes, predominantly $CD4^+$ and $CD8^+$ T cells, and insulitis, with subsequent hypoinsulinemia and hyperglycemia. Administration of the SP16 peptide can delay and/or prevent development of type I diabetes in NOD mice similar to hAAT treatment (FIG. 18).

We claim:

1. A method of decreasing serum TNF-α levels in a human subject comprising administering to the subject a composition comprising a peptide wherein the peptide comprises the amino acid sequence
X1-Z1-F-N-X2-P-F-X3-Z2-X4-Z3-X5 (SEQ ID NO: 3), wherein
X1 is V or L;
X2 is K or R;
X3 is V, L or M;
X4 is M, I or V;
X5 is K or Q;
Z1 is any amino acid;
Z2 is a sequence of any two amino acids; and
Z3 is a sequence of any five amino acids; and wherein the peptide is 21 or fewer amino acids in length.

2. The method of claim 1, wherein the subject is administered the composition in an amount that results in at least 50% reduction of the TNF-α levels compared to the TNF-α levels in the subject prior to administering the peptide.

3. The method of claim 2, wherein reduction of the TNF-α levels is at least 75%.

4. The method of claim 1, wherein the peptide comprises the amino acid sequence of any one of:

```
                            (SEQ ID NO: 1)
VKFNKPFVFLMIEQNTK;

(SEQ ID NO: 16)
VKFNKPFVFLMIAAATK;

(SEQ ID NO: 29)
IPPEVKFNKPFVFLMIEQNTK;

(SEQ ID NO:44)
VRFNRPFLMIIVPTDTQ; or (SEQ ID NO:31)
TRTIVRFNRPFLMIIVPTDTQ;
```
and is 21 or fewer amino acids in length.

5. The method of claim 4, wherein the peptide consists of the amino acid sequence of any one of:

```
                            (SEQ ID NO: 1)
VKFNKPFVFLMIEQNTK;

(SEQ ID NO: 16)
VKFNKPFVFLMIAAATK; or (SEQ ID NO:44)
VRFNRPFLMIIVPTDTQ.
```

6. The method of claim 5, wherein the peptide consists of the amino acid sequence of VKFNKPFVFLMIEQNTK (SEQ ID NO: 1).

7. The method of claim 1, wherein the decreasing serum TNF-α levels in the human subject treats sepsis.

8. The method of claim 7, wherein the sepsis is associated with a burn or acute radiation.

9. The method of claim 1, wherein the peptide is fused to at least one second peptide or protein.

10. The method of claim 9, wherein the at least one second peptide or protein is an epitope tag, a half-life extender, or both.

11. The method of claim 1, wherein the peptide comprises one or more D-amino acids.

12. The method of claim 1, wherein the composition further comprises one or more pharmaceutically acceptable carriers.

13. The method of claim 1, wherein the composition is administered orally.

14. The method of claim 1, wherein the composition is administered by subcutaneous, intravenous, intramuscular, or intraperitoneal injection.

15. The method of claim 1, wherein the composition is administered nasally, rectally, intravaginally, parenterally, intracisternally or topically.

* * * * *